US010590419B2

(12) United States Patent
Morrisey

(10) Patent No.: US 10,590,419 B2
(45) Date of Patent: Mar. 17, 2020

(54) MICRORNA INDUCTION OF CARDIAC REGENERATION

(71) Applicant: THE TRUSTEES OF THE UNIVERSITY OF PENNSYLVANIA, Philadelphia, PA (US)

(72) Inventor: Edward E. Morrisey, Newtown Square, PA (US)

(73) Assignee: THE TRUSTEES OF THE UNIVERSITY OF PENNSYLVANIA, Philadelphia, PA (US)

(*) Notice: Subject to any disclaimer, the term of this patent is extended or adjusted under 35 U.S.C. 154(b) by 60 days.

(21) Appl. No.: 15/311,765

(22) PCT Filed: May 15, 2015

(86) PCT No.: PCT/US2015/030990
§ 371 (c)(1),
(2) Date: Nov. 16, 2016

(87) PCT Pub. No.: WO2015/175889
PCT Pub. Date: Nov. 19, 2015

(65) Prior Publication Data
US 2017/0096671 A1 Apr. 6, 2017

Related U.S. Application Data

(60) Provisional application No. 61/994,250, filed on May 16, 2014.

(51) Int. Cl.
C12N 15/113 (2010.01)
C12N 5/077 (2010.01)
A61K 31/19 (2006.01)
A61K 31/7105 (2006.01)
A61K 48/00 (2006.01)
C12N 5/0775 (2010.01)
C12N 15/86 (2006.01)

(52) U.S. Cl.
CPC .......... C12N 15/1137 (2013.01); A61K 31/19 (2013.01); A61K 31/7105 (2013.01); A61K 48/0058 (2013.01); A61K 48/0075 (2013.01); C12N 5/0657 (2013.01); C12N 5/0662 (2013.01); C12N 15/113 (2013.01); C12N 15/86 (2013.01); A01K 2227/105 (2013.01); A01K 2267/0375 (2013.01); C12N 2310/141 (2013.01); C12N 2320/32 (2013.01); C12N 2320/35 (2013.01); C12N 2501/65 (2013.01); C12N 2510/00 (2013.01); C12N 2740/15043 (2013.01)

(58) Field of Classification Search
CPC combination set(s) only.
See application file for complete search history.

(56) References Cited

U.S. PATENT DOCUMENTS

| 4,873,316 A | 10/1989 | Meade et al. |
| 6,756,196 B2 | 6/2004 | Berlin et al. |
| 2007/0269889 A1 | 11/2007 | Leake et al. |
| 2009/0246875 A1 | 10/2009 | Yamanaka et al. |
| 2010/0062534 A1 | 3/2010 | Hochedlinger et al. |
| 2013/0035374 A1 | 2/2013 | Morrisey et al. |
| 2016/0040161 A1* | 2/2016 | Packard ............ A61K 48/0025 514/44 A |

FOREIGN PATENT DOCUMENTS

| EP | 264166 | 8/2006 |
| WO | WO/2009/091659 | 7/2009 |
| WO | WO 2012/006577 A2 | 1/2012 |
| WO | WO 2013/093870 A1 | 6/2013 |

OTHER PUBLICATIONS

Giacca, M. (2015) RNA Mimics as Therapeutics for Cardiac Regeneration: A Paradigm Shift. Molecular Therapy, V.23(6): 984-6. (Year: 2015).*
Tian, et al. (2015) A microRNA-Hippo pathway that promotes cardiomyocyte proliferation and cardiac regeneration in mice. Science Translational Medicine, V.7(279):279ra38. (Year: 2015).*
Scott, et al. (2008) Aiming for the Heart: Targeted Delivery of Drugs to Diseased Cardiac Tissue. Expert Opinion on Drug Delivery, V.5(4):459-70. (Year: 2008).*
Cook, et al. (2009). Intracerebroventricular Administration of Drugs. Pharmacotherapy, V.29(7):832-45. (Year: 2009).*
Berridge, M.J. (2012) Cell Signalling Biology; doi:10.1042/csb0001009.*
Helnich, Eva-Marie, and Stefanie Dimmeler. "MicroRNAs and stem cells control of pluripotency, reprogramming, and lineage commitment." Circulation research 110.7 (2012): 1014-1022.
Lin et al, "Mir-302 reprograms human skin cancer cells into a pluripotent ES-cell like state" (2008b) RNA 14: 2115-2124.
Takahashi et al., "Induction of pluripotent stem cells from mouse embryonic and adult fibroblast cultures by defined factors" Cell 126:663-76, 2006.
Suh et al., "Human embryonic stem cells express a unique set of microRNAs", 2004 (Dev. Biol. 270:488-498.
Drummond et al., (2005) "Clinical development of histone deacetylase inhibitors as anticancer agents", Annu Rev Pharmacol Toxicol 45: 495-528.
Calame et al., "Transcriptional controlling elements in the immunoglobulin and T cell receptor loci", (1988) Adv. Immunol. 43:235-275.

(Continued)

Primary Examiner — Jennifer Pitrak McDonald
(74) Attorney, Agent, or Firm — Mark S. Cohen; Pearl Cohen Zedek Latzer Baratz LLP

(57) ABSTRACT

The invention relates to compostions and methods for promoting cellular proliferation and de-differentiation of cells into stem cells to foster tissue regeneration. Specifically, the invention relates to transiently administering a microRNA (miR) or its mimic for promoting cardiomyocyte proliferation and cardiac regeneration.

13 Claims, 30 Drawing Sheets

Specification includes a Sequence Listing.

(56) References Cited

OTHER PUBLICATIONS

Banerji et al., "A lymphocyte-specific cellular enhancer is located downstream of the joining region in immunoglobulin heavy chain genes", (1983) Cell 33:729-740.
Queen et al., "Immunoglobulin gene transcription is activated by downstream sequence elements", (1983) Cell 33:741-748.
Edlund et al., "Cell-specific expression of the rat insulin gene: evidence for role of two distinct 5' flanking elements", (1985) Science 230:912-916.
Kessel et al., "Murine developmental control genes", (1990) Science 249:374-379.
Huangfu et al., "Induction of pluripotent stem cells by defined factors is greatly improved by small-molecule compounds", Nat Biotechnol. 2008a; 26:795-797.
Rosa et al., "The miR-430/427/302 family controls mesendodermal fate specification via species-specific target selection", Dev Cell. 2009; 16:517-527.
Pinkert et al., "An albumin enhancer located 10 kb upstream functions along with its promoter to direct efficient, liver-specific expression in transgenic mice", (1987) Genes Dev. 1:268-277.
Winoto and Baltimore, "A novel, inducible and T cell-specific enhancer located at the 3' end of the T cell receptor alpha locus", (1989) EMBO J. 8:729-733.
Byrne and Ruddle, "Multiplex gene regulation: a two-tiered approach to transgene regulation in transgenic mice", (1989) Proc. Natl. Acad. Sci. USA 86:5473-5477.
Camper and Tilghman, "Postnatal repression of the alpha-fetoprotein gene is enhancer independent", (1989) Genes Dev. 3:537-546.
Blelloch et al., "Generation of induced pluripotent stem cells in the absence of drug selection", Cell Stem Cell. 2007; 1:245-247.
Shu W, et al., "Wnt7b regulates mesenchymal proliferation and vascular development in the lung", Development. 2002; 129:4831-4842.
Cohen ED, et al. "Wnt signaling regulates smooth muscle precursor development in the mouse lung via a tenascin C/PDGFR pathway", J Clin Invest. 2009; 119:2538-2549.
Trivedi CM,et al., "Transgenic overexpression of Hdac3 in the heart produces increased postnatal cardiac myocyte proliferation but does not induce hypertrophy". J Biol Chem. 2008; 283:26484-26489.
Card DA, et al., "Oct4/Sox2-regulated miR-302 targets cyclin D1 in human embryonic stem cells", Mol Cell Biol. 2008; 28:6426-6438.
Lengner CJ, et al., "Oct4 expression is not required for mouse somatic stem cell self-renewal", Cell Stem Cell. 2007; 1:403-415.
Sommer CA, et al., "Induced pluripotent stem cell generation using a single lentiviral stem cell cassette", Stem Cells. 2009; 27:543-549.
Friedrich G, et al., "Promoter traps in embryonic stem cells: a genetic screen to identify and mutate developmental genes in mice", Genes Dev. 1991; 5:1513-1523.
Ana Eulalio et al: "Functional screening identifies miRNAs inducing cardiac regeneration", Nature, vol. 492, No. 7429, Dec. 5, 2012 (Dec. 5, 2012), pp. 376-381, ISSN: 0028-0836, DOI: 10.1038/nature11739.
Y. Tian et al: "A microRNA-Hippo pathway that promotes cardiomyocyte proliferation and cardiac regeneration in mice", Science Translational Medicine, vol. 7, No. 279,Mar. 18, 2015 (Mar. 18, 2015), pp. 279ra38-279ra38, ISSN: 1946-6234, DOI: 1 0.1126/scitranslmed.301 0841.
J. Chen et al: "mir-17-92 Cluster is Required for and Sufficient to Induce Cardiomyocyte Proliferation in Postnatal and Adult Hearts", Circulation Research., vol. 112, No. 12, Apr. 10, 2013 (Apr. 10, 2013), pp. 1557-1566, US ISSN: 0009-7330, DOI: 10.1161/CIRCRESAHA.112.300658.
Barroso Del-Jesus A et al: "Embryonic Stem Cell-Specific miR302-367 Cluster: Human Gene Structure and Functional Characterization of Its Core Promoter", Molecular and Cellular Biology, American Society for Microbiology, Washington, US, vol. 28, No. 21,Nov. 1, 2008 (Nov. 1, 2008), pp. 6609-6619, ISSN: 0270-7306, DOI: 10.1128/MCB.00398-08 [retrieved on Aug. 25, 2008].

\* cited by examiner

A

B

Myh6$^{mercremer}$:
R26R-miR302-367$^{Tg/+}$

C

A

B

A

1. Negative regulation cell proliferation: Cdkn 1a (P21)
2. Positive regulation of apoptosis: Casp2, Bach1
3. Hippo signaling cascades: Stk4(Mst1)
4. Endocytosis: Rab11b, Grb2l2, LdlR

B

C

D

3'  UGUGAGUUUGUACCUUCGUGAAU    miR-302d
3'  GGUGACUUUGUACCUUCGUGAAC    miR-302c
3'  GAUGAUUUUGUACCUUCGUGAAU    miR-302b
3'  AGUGGUUUUGUACCUUCGUGAAU    miR-302a
                     ||||||
5' ...UCAUGUCUGUUAGCCAGCACUUC... Mst1 3'UTR
5' ...UCAUGUCUGUUAGCCAAAGCUUC... Mst1 3'UTR-mut 3'  AGUGGUUUUGUACCU---UCGUGAAU  miR-302a
     | : | : : | | | | |     | | | | | |
5' ...UUAGUACAGUAUGGAAAGAGCACUUA.. Lats2 3'UTR
5' ...UUAGUACAGUAUGGAAAGAAAGCUUA.. Lats2 3'UTR-mut1

3'  AGUGGUUUUGUACCUUCGUGAAU    miR-302a
       | :  | |     | | | | | | |
5' ...UGUGUUGUAUCUGAUAGCACUUG... Lats2 3'UTR
5' ...UGUGUUGUAUCUGAUAAGCUUG... Lats2 3'UTR-mut2

3'  AGUGGUUUU----GUACCU-UCGUGAAU  miR-302a
     | : : | : | |     : | |  |  : | | | | | |
5'...AUAUUAGAAUUUCUAUCUAGGGCACUUA..Mob1b 3'UTR
5'...AUAUUAGAAUUUCUAUCUAGGGCCCUUA..Mob1b 3'UTR-mut

☐ Myh6$^{mercremer}$
▨ Myh6$^{mercremer}$:R26R-miR302-367$^{Tg/+}$ - Day 10
■ Myh6$^{mercremer}$:R26R-miR302-367$^{Tg/+}$ - Day 21

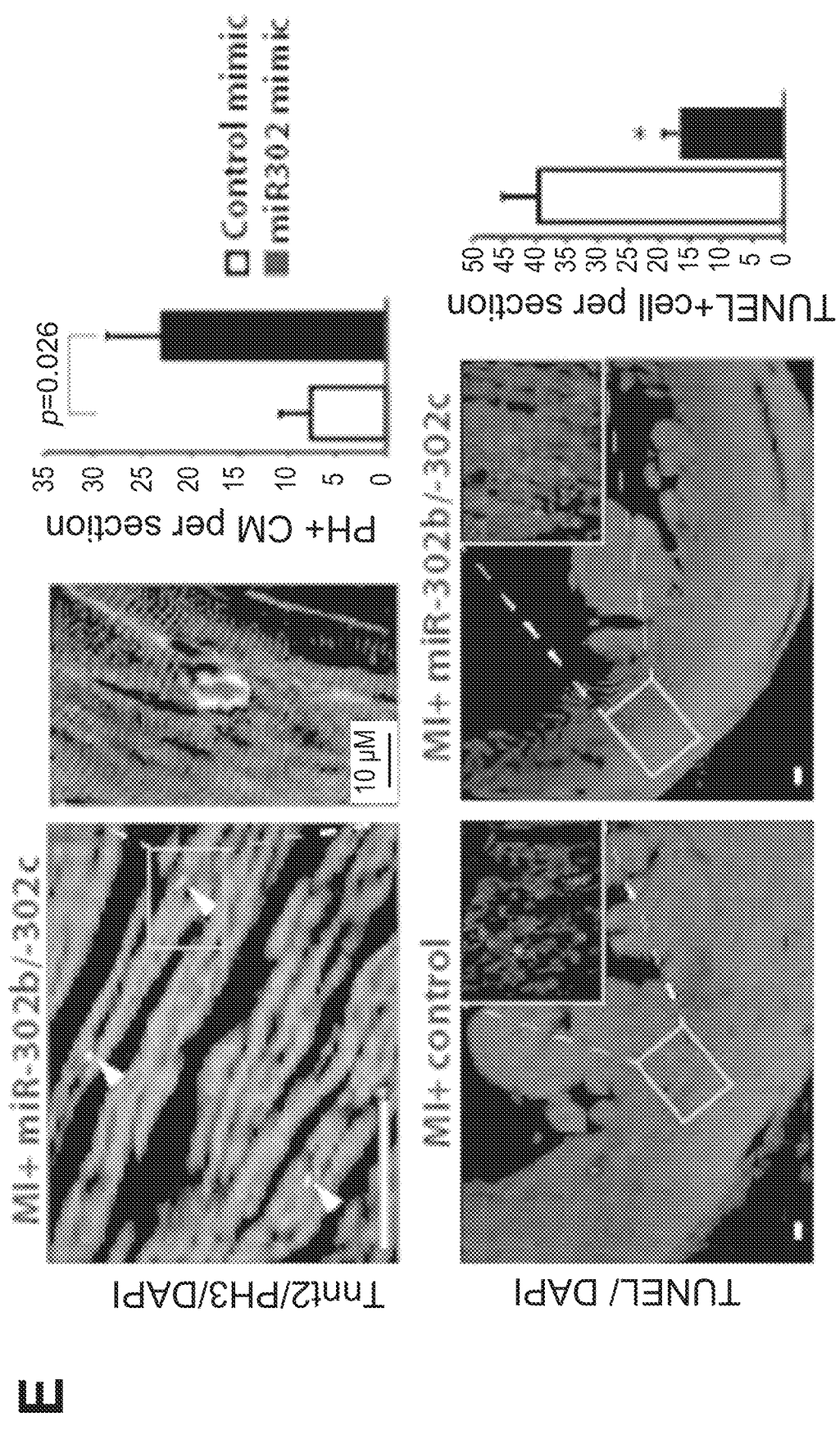

G

H

SEQUENCE LISTING

```
<160> NUMBER OF SEQ ID NOS: 87

<210> SEQ ID NO 1
<211> LENGTH: 23
<212> TYPE: RNA
<213> ORGANISM: Homo sapiens

<400> SEQUENCE: 1
uaagugcuuc cauguuuuag uag                                               23

<210> SEQ ID NO 2
<211> LENGTH: 23
<212> TYPE: RNA
<213> ORGANISM: Homo sapiens

<400> SEQUENCE: 2
acuuuaacau ggaagugcuu ucu                                               23

<210> SEQ ID NO 3
<211> LENGTH: 23
<212> TYPE: RNA
<213> ORGANISM: Homo sapiens

<400> SEQUENCE: 3
uaagugcuuc cauguuucag ugg                                               23

<210> SEQ ID NO 4
<211> LENGTH: 22
<212> TYPE: RNA
<213> ORGANISM: Homo sapiens
```

-continued

```
<400> SEQUENCE: 4
uuuaacaugg ggguaccugc ug                                          22

<210> SEQ ID NO 5
<211> LENGTH: 23
<212> TYPE: RNA
<213> ORGANISM: Homo sapiens

<400> SEQUENCE: 5
uaagugguuc cauguuuugg uga                                         23

<210> SEQ ID NO 6
<211> LENGTH: 22
<212> TYPE: RNA
<213> ORGANISM: Homo sapiens

<400> SEQUENCE: 6
uaaacgugga uguacuugcu uu                                          22

<210> SEQ ID NO 7
<211> LENGTH: 23
<212> TYPE: RNA
<213> ORGANISM: Homo sapiens

<400> SEQUENCE: 7
uaagugcuuc cauguuugag ugu                                         23

<210> SEQ ID NO 8
<211> LENGTH: 22
<212> TYPE: RNA
<213> ORGANISM: Homo sapiens

<400> SEQUENCE: 8
aauugcacuu uagcaauggu ga                                          22

<210> SEQ ID NO 9
<211> LENGTH: 22
<212> TYPE: RNA
<213> ORGANISM: Homo sapiens

<400> SEQUENCE: 9
acuguugcua auaugcaacu cu                                          22

<210> SEQ ID NO 10
<211> LENGTH: 24
<212> TYPE: DNA
<213> ORGANISM: Mus musculus

<400> SEQUENCE: 10
cacaaggaga gacataagat gggc                                        24

<210> SEQ ID NO 11
<211> LENGTH: 23
<212> TYPE: DNA
<213> ORGANISM: Mus musculus

<400> SEQUENCE: 11
cactttagca atggtgatgg acc                                         23

<210> SEQ ID NO 12
<211> LENGTH: 21
<212> TYPE: DNA
<213> ORGANISM: Mus musculus
```

<400> SEQUENCE: 12
aaagtcgctc tgagttgtta t          21

<210> SEQ ID NO 13
<211> LENGTH: 20
<212> TYPE: DNA
<213> ORGANISM: Mus musculus

<400> SEQUENCE: 13
tccctattgg cgttactatg          20

<210> SEQ ID NO 14
<211> LENGTH: 21
<212> TYPE: DNA
<213> ORGANISM: Mus musculus

<400> SEQUENCE: 14
cgttttctga gcatacctgg a          21

<210> SEQ ID NO 15
<211> LENGTH: 20
<212> TYPE: DNA
<213> ORGANISM: Mus musculus

<400> SEQUENCE: 15
attctcccac cgtcagtacg          20

<210> SEQ ID NO 16
<211> LENGTH: 21
<212> TYPE: DNA
<213> ORGANISM: Mus musculus

<400> SEQUENCE: 16
cgttttctga gcatacctgg a          21

<210> SEQ ID NO 17
<211> LENGTH: 20
<212> TYPE: DNA
<213> ORGANISM: Mus musculus

<400> SEQUENCE: 17
attctcccac cgtcagtacg          20

<210> SEQ ID NO 18
<211> LENGTH: 23
<212> TYPE: DNA
<213> ORGANISM: Artificial Sequence
<220> FEATURE:
<223> OTHER INFORMATION: Q-PCR Ccnd1 forward primer

<400> SEQUENCE: 18
gatgtgaggg aagaggtgaa ggt          23

<210> SEQ ID NO 19
<211> LENGTH: 24
<212> TYPE: DNA
<213> ORGANISM: Artificial Sequence
<220> FEATURE:
<223> OTHER INFORMATION: Q-PCR Ccnd1 reverse primer

<400> SEQUENCE: 19
caatgagaat ctggttctga acgt          24

```
<210> SEQ ID NO 20
<211> LENGTH: 19
<212> TYPE: DNA
<213> ORGANISM: Artificial Sequence
<220> FEATURE:
<223> OTHER INFORMATION: Q-PCR Nkx2.5 forward primer

<400> SEQUENCE: 20
tgacccagcc aaagaccct                                                19

<210> SEQ ID NO 21
<211> LENGTH: 19
<212> TYPE: DNA
<213> ORGANISM: Artificial Sequence
<220> FEATURE:
<223> OTHER INFORMATION: Q-PCR Nkx2.5 reverse primer

<400> SEQUENCE: 21
ccatccgtct cggctttgt                                                19

<210> SEQ ID NO 22
<211> LENGTH: 21
<212> TYPE: DNA
<213> ORGANISM: Artificial Sequence
<220> FEATURE:
<223> OTHER INFORMATION: Q-PCR Gata4 forward primer

<400> SEQUENCE: 22
ccgggctgtc atctcactat g                                             21

<210> SEQ ID NO 23
<211> LENGTH: 22
<212> TYPE: DNA
<213> ORGANISM: Artificial Sequence
<220> FEATURE:
<223> OTHER INFORMATION: Q-PCR Gata4 reverse primer

<400> SEQUENCE: 23
ttcagagcag acagcactgg at                                            22

<210> SEQ ID NO 24
<211> LENGTH: 23
<212> TYPE: DNA
<213> ORGANISM: Artificial Sequence
<220> FEATURE:
<223> OTHER INFORMATION: Q-PCR Myh6 forward primer

<400> SEQUENCE: 24
ccacttctcc ttggtccact atg                                           23

<210> SEQ ID NO 25
<211> LENGTH: 20
<212> TYPE: DNA
<213> ORGANISM: Artificial Sequence
<220> FEATURE:
<223> OTHER INFORMATION: Q-PCR Myh6 reverse primer

<400> SEQUENCE: 25
acaaacccac caccgtctca                                               20

<210> SEQ ID NO 26
<211> LENGTH: 20
<212> TYPE: DNA
<213> ORGANISM: Artificial Sequence
<220> FEATURE:
<223> OTHER INFORMATION: Q-PCR Myh7 forward primer
```

<400> SEQUENCE: 26
tacctcatgg ggctgaactc         20

<210> SEQ ID NO 27
<211> LENGTH: 20
<212> TYPE: DNA
<213> ORGANISM: Artificial Sequence
<220> FEATURE:
<223> OTHER INFORMATION: Q-PCR Myh7 reverse primer

<400> SEQUENCE: 27
cccttggtga cgtactcgtt         20

<210> SEQ ID NO 28
<211> LENGTH: 23
<212> TYPE: DNA
<213> ORGANISM: Artificial Sequence
<220> FEATURE:
<223> OTHER INFORMATION: Q-PCR Mob1b forward primer

<400> SEQUENCE: 28
ctgtgatcca gcttcaggag gaa         23

<210> SEQ ID NO 29
<211> LENGTH: 20
<212> TYPE: DNA
<213> ORGANISM: Artificial Sequence
<220> FEATURE:
<223> OTHER INFORMATION: Q-PCR Mob1b reverse primer

<400> SEQUENCE: 29
tgccaactct cgtctgtcaa         20

<210> SEQ ID NO 30
<211> LENGTH: 24
<212> TYPE: DNA
<213> ORGANISM: Artificial Sequence
<220> FEATURE:
<223> OTHER INFORMATION: Q-PCR Lats2 forward primer

<400> SEQUENCE: 30
taagggtcct gcttcctgtg ttct         24

<210> SEQ ID NO 31
<211> LENGTH: 24
<212> TYPE: DNA
<213> ORGANISM: Artificial Sequence
<220> FEATURE:
<223> OTHER INFORMATION: Q-PCR Lats2 reverse primer

<400> SEQUENCE: 31
acctctcatg tgaaagaggc ccaa         24

<210> SEQ ID NO 32
<211> LENGTH: 24
<212> TYPE: DNA
<213> ORGANISM: Artificial Sequence
<220> FEATURE:
<223> OTHER INFORMATION: Q-PCR Mst1 forward primer

<400> SEQUENCE: 32
cagggcctgc ataacatttg ctgt         24

```
<210> SEQ ID NO 33
<211> LENGTH: 24
<212> TYPE: DNA
<213> ORGANISM: Artificial Sequence
<220> FEATURE:
<223> OTHER INFORMATION: Q-PCR Mst1 reverse primer

<400> SEQUENCE: 33
ttccttgtct ggcaaagccc aaag                                           24

<210> SEQ ID NO 34
<211> LENGTH: 22
<212> TYPE: DNA
<213> ORGANISM: Artificial Sequence
<220> FEATURE:
<223> OTHER INFORMATION: Q-PCR Bcl2 forward primer

<400> SEQUENCE: 34
gtggatgact gagtacctga ac                                             22

<210> SEQ ID NO 35
<211> LENGTH: 21
<212> TYPE: DNA
<213> ORGANISM: Artificial Sequence
<220> FEATURE:
<223> OTHER INFORMATION: Q-PCR Bcl2 reverse primer

<400> SEQUENCE: 35
gagacagcca ggagaaatca a                                              21

<210> SEQ ID NO 36
<211> LENGTH: 18
<212> TYPE: DNA
<213> ORGANISM: Artificial Sequence
<220> FEATURE:
<223> OTHER INFORMATION: Q-PCR Brca2 forward primer

<400> SEQUENCE: 36
atttgaacgg cccagcat                                                  18

<210> SEQ ID NO 37
<211> LENGTH: 22
<212> TYPE: DNA
<213> ORGANISM: Artificial Sequence
<220> FEATURE:
<223> OTHER INFORMATION: Q-PCR Brca2 reverse primer

<400> SEQUENCE: 37
ggctggtaaa cctggagtaa ag                                             22

<210> SEQ ID NO 38
<211> LENGTH: 22
<212> TYPE: DNA
<213> ORGANISM: Artificial Sequence
<220> FEATURE:
<223> OTHER INFORMATION: Q-PCR RacGap1 forward primer

<400> SEQUENCE: 38
cagatccagt gacaatgttc ca                                             22

<210> SEQ ID NO 39
<211> LENGTH: 22
<212> TYPE: DNA
<213> ORGANISM: Artificial Sequence
<220> FEATURE:
<223> OTHER INFORMATION: Q-PCR RacGap1 reverse primer
```

```
<400> SEQUENCE: 39
tccaccatca tgaactgatt cc                                          22

<210> SEQ ID NO 40
<211> LENGTH: 21
<212> TYPE: DNA
<213> ORGANISM: Artificial Sequence
<220> FEATURE:
<223> OTHER INFORMATION: Q-PCR Nusap1 forward primer

<400> SEQUENCE: 40
gaggaggaag aagcacaaga c                                           21

<210> SEQ ID NO 41
<211> LENGTH: 26
<212> TYPE: DNA
<213> ORGANISM: Artificial Sequence
<220> FEATURE:
<223> OTHER INFORMATION: Q-PCR Nusap1 reverse primer

<400> SEQUENCE: 41
ctactatcag ttcctttcat ctccaa                                      26

<210> SEQ ID NO 42
<211> LENGTH: 21
<212> TYPE: DNA
<213> ORGANISM: Artificial Sequence
<220> FEATURE:
<223> OTHER INFORMATION: Q-PCR Myh10 forward primer

<400> SEQUENCE: 42
ggaattcgag aggcagaaca a                                           21

<210> SEQ ID NO 43
<211> LENGTH: 20
<212> TYPE: DNA
<213> ORGANISM: Artificial Sequence
<220> FEATURE:
<223> OTHER INFORMATION: Q-PCR Myh10 reverse primer

<400> SEQUENCE: 43
aaggctcgct tggatttctc                                             20

<210> SEQ ID NO 44
<211> LENGTH: 24
<212> TYPE: DNA
<213> ORGANISM: Artificial Sequence
<220> FEATURE:
<223> OTHER INFORMATION: Q-PCR Cks2 forward primer

<400> SEQUENCE: 44
cagagtctag gatgggttca ttac                                        24

<210> SEQ ID NO 45
<211> LENGTH: 19
<212> TYPE: DNA
<213> ORGANISM: Artificial Sequence
<220> FEATURE:
<223> OTHER INFORMATION: Q-PCR Cks2 reverse primer

<400> SEQUENCE: 45
tcccagctgc acttcattt                                              19
```

```
<210> SEQ ID NO 46
<211> LENGTH: 20
<212> TYPE: DNA
<213> ORGANISM: Artificial Sequence
<220> FEATURE:
<223> OTHER INFORMATION: Q-PCR Dapk1 forward primer

<400> SEQUENCE: 46
gctgaacatg gagctgactt                                                   20

<210> SEQ ID NO 47
<211> LENGTH: 22
<212> TYPE: DNA
<213> ORGANISM: Artificial Sequence
<220> FEATURE:
<223> OTHER INFORMATION: Q-PCR Dapk1 reverse primer

<400> SEQUENCE: 47
caaggagggt cttgatgact tc                                                22

<210> SEQ ID NO 48
<211> LENGTH: 22
<212> TYPE: DNA
<213> ORGANISM: Artificial Sequence
<220> FEATURE:
<223> OTHER INFORMATION: Q-PCR Stk17B forward primer

<400> SEQUENCE: 48
aatctgcatg aggtctacga aa                                                22

<210> SEQ ID NO 49
<211> LENGTH: 21
<212> TYPE: DNA
<213> ORGANISM: Artificial Sequence
<220> FEATURE:
<223> OTHER INFORMATION: Q-PCR Stk17B reverse primer

<400> SEQUENCE: 49
tcggctaact caggtaaaca c                                                 21

<210> SEQ ID NO 50
<211> LENGTH: 22
<212> TYPE: DNA
<213> ORGANISM: Artificial Sequence
<220> FEATURE:
<223> OTHER INFORMATION: Q-PCR c-Kit forward primer

<400> SEQUENCE: 50
ctagccagag acatcaggaa tg                                                22

<210> SEQ ID NO 51
<211> LENGTH: 22
<212> TYPE: DNA
<213> ORGANISM: Artificial Sequence
<220> FEATURE:
<223> OTHER INFORMATION: Q-PCR c-Kit reverse primer

<400> SEQUENCE: 51
ctcccagagg aaaatcccat ag                                                22

<210> SEQ ID NO 52
<211> LENGTH: 21
<212> TYPE: DNA
<213> ORGANISM: Artificial Sequence
<220> FEATURE:
<223> OTHER INFORMATION: Q-PCR Nppa forward primer
```

<400> SEQUENCE: 52
gggtaggatt gacaggattg g                                              21

<210> SEQ ID NO 53
<211> LENGTH: 21
<212> TYPE: DNA
<213> ORGANISM: Artificial Sequence
<220> FEATURE:
<223> OTHER INFORMATION: Q-PCR Nppa reverse primer

<400> SEQUENCE: 53
ctccttggct gttatcttcg g                                              21

<210> SEQ ID NO 54
<211> LENGTH: 21
<212> TYPE: DNA
<213> ORGANISM: Artificial Sequence
<220> FEATURE:
<223> OTHER INFORMATION: Q-PCR PparA forward primer

<400> SEQUENCE: 54
agggggactg catagtttgt c                                              21

<210> SEQ ID NO 55
<211> LENGTH: 20
<212> TYPE: DNA
<213> ORGANISM: Artificial Sequence
<220> FEATURE:
<223> OTHER INFORMATION: Q-PCR PparA reverse primer

<400> SEQUENCE: 55
ttctcggcca tacacaaggt                                                20

<210> SEQ ID NO 56
<211> LENGTH: 20
<212> TYPE: DNA
<213> ORGANISM: Artificial Sequence
<220> FEATURE:
<223> OTHER INFORMATION: Q-PCR PparD forward primer

<400> SEQUENCE: 56
atctctgtct ctccctgccc                                                20

<210> SEQ ID NO 57
<211> LENGTH: 20
<212> TYPE: DNA
<213> ORGANISM: Artificial Sequence
<220> FEATURE:
<223> OTHER INFORMATION: Q-PCR PparD reverse primer

<400> SEQUENCE: 57
ctgtggctgt tccatgactg                                                20

<210> SEQ ID NO 58
<211> LENGTH: 20
<212> TYPE: DNA
<213> ORGANISM: Artificial Sequence
<220> FEATURE:
<223> OTHER INFORMATION: Q-PCR Acox1 forward primer

<400> SEQUENCE: 58
gaaatatgcc caggtgaagc                                                20

<210> SEQ ID NO 59
<211> LENGTH: 21
<212> TYPE: DNA
<213> ORGANISM: Artificial Sequence
<220> FEATURE:
<223> OTHER INFORMATION: Q-PCR Acox1 reverseprimer

<400> SEQUENCE: 59
cagactctga gctgcacttc c                                              21

<210> SEQ ID NO 60
<211> LENGTH: 20
<212> TYPE: DNA
<213> ORGANISM: Artificial Sequence
<220> FEATURE:
<223> OTHER INFORMATION: Q-PCR Pdk4 forward primer

<400> SEQUENCE: 60
tgaacacgct tcacccacta                                                20

<210> SEQ ID NO 61
<211> LENGTH: 20
<212> TYPE: DNA
<213> ORGANISM: Artificial Sequence
<220> FEATURE:
<223> OTHER INFORMATION: Q-PCR Pdk4 reverse primer

<400> SEQUENCE: 61
caggcaggat gtcaatctcc                                                20

<210> SEQ ID NO 62
<211> LENGTH: 21
<212> TYPE: DNA
<213> ORGANISM: Artificial Sequence
<220> FEATURE:
<223> OTHER INFORMATION: Q-PCR Larp7 E12-13 forward primer

<400> SEQUENCE: 62
ggatcatgag cagaggtact g                                              21

<210> SEQ ID NO 63
<211> LENGTH: 21
<212> TYPE: DNA
<213> ORGANISM: Artificial Sequence
<220> FEATURE:
<223> OTHER INFORMATION: Q-PCR Larp7 E12-13 reverse primer

<400> SEQUENCE: 63
gactggcttg ctgagtctta g                                              21

<210> SEQ ID NO 64
<211> LENGTH: 21
<212> TYPE: DNA
<213> ORGANISM: Artificial Sequence
<220> FEATURE:
<223> OTHER INFORMATION: Q-PCR Larp7 E8-9 forward primer

<400> SEQUENCE: 64
tctcaaaggt gaagaggaag c                                              21

<210> SEQ ID NO 65
<211> LENGTH: 21
<212> TYPE: DNA
<213> ORGANISM: Artificial Sequence
<220> FEATURE:
<223> OTHER INFORMATION: Q-PCR Larp7 E8-9 reverse primer

```
<400> SEQUENCE: 65
tcttggacag cactctcaat g                                              21

<210> SEQ ID NO 66
<211> LENGTH: 21
<212> TYPE: DNA
<213> ORGANISM: Artificial Sequence
<220> FEATURE:
<223> OTHER INFORMATION: Q-PCR Larp7 E89-10 forward primer

<400> SEQUENCE: 66
attgagagtg ctgtccaaga c                                              21

<210> SEQ ID NO 67
<211> LENGTH: 20
<212> TYPE: DNA
<213> ORGANISM: Artificial Sequence
<220> FEATURE:
<223> OTHER INFORMATION: Q-PCR Larp7 E89-10 reverse primer

<400> SEQUENCE: 67
tctccgctca caatcttcac                                                20

<210> SEQ ID NO 68
<211> LENGTH: 20
<212> TYPE: DNA
<213> ORGANISM: Artificial Sequence
<220> FEATURE:
<223> OTHER INFORMATION: Q-PCR GAPDH forward primer

<400> SEQUENCE: 68
tgcaccacca actgcttagc                                                20

<210> SEQ ID NO 69
<211> LENGTH: 21
<212> TYPE: DNA
<213> ORGANISM: Artificial Sequence
<220> FEATURE:
<223> OTHER INFORMATION: Q-PCR GAPDH reverse primer

<400> SEQUENCE: 69
ggcatggact gtggtcatga g                                              21

<210> SEQ ID NO 70
<211> LENGTH: 28
<212> TYPE: DNA
<213> ORGANISM: Artificial Sequence
<220> FEATURE:
<223> OTHER INFORMATION: Lats2 XhoI fwd primer

<400> SEQUENCE: 70
cctcgaggtt ctggtaaatg ggcaacag                                       28

<210> SEQ ID NO 71
<211> LENGTH: 28
<212> TYPE: DNA
<213> ORGANISM: Artificial Sequence
<220> FEATURE:
<223> OTHER INFORMATION: Lats2 EcoRI rev primer

<400> SEQUENCE: 71
ggaattcctt tacatttgcc tcccgaag                                       28
```

```
<210> SEQ ID NO 72
<211> LENGTH: 24
<212> TYPE: DNA
<213> ORGANISM: Artificial Sequence
<220> FEATURE:
<223> OTHER INFORMATION: Mst1 XhoI fwd primer

<400> SEQUENCE: 72
ccgctcgagc aacaccagcc cagc                                              24

<210> SEQ ID NO 73
<211> LENGTH: 29
<212> TYPE: DNA
<213> ORGANISM: Artificial Sequence
<220> FEATURE:
<223> OTHER INFORMATION: Mst1 BamHI rev primer

<400> SEQUENCE: 73
cgcggatccc ctagcagcca tttatcatc                                         29

<210> SEQ ID NO 74
<211> LENGTH: 29
<212> TYPE: DNA
<213> ORGANISM: Artificial Sequence
<220> FEATURE:
<223> OTHER INFORMATION: Mob1b XhoI fwd primer

<400> SEQUENCE: 74
ccgctcgaga ggttttgggg cttgcttgg                                         29

<210> SEQ ID NO 75
<211> LENGTH: 32
<212> TYPE: DNA
<213> ORGANISM: Artificial Sequence
<220> FEATURE:
<223> OTHER INFORMATION: Mob1b EcoRI rev primer

<400> SEQUENCE: 75
ccggaattcg gagtcaggat gcttcaaact gc                                     32

<210> SEQ ID NO 76
<211> LENGTH: 23
<212> TYPE: RNA
<213> ORGANISM: Artificial Sequence
<220> FEATURE:
<223> OTHER INFORMATION: miR-302d primer

<400> SEQUENCE: 76
uaagugcuuc cauguuugag ugu                                               23

<210> SEQ ID NO 77
<211> LENGTH: 23
<212> TYPE: RNA
<213> ORGANISM: Mus musculus

<400> SEQUENCE: 77
caagugcuuc cauguuucag ugg                                               23

<210> SEQ ID NO 78
<211> LENGTH: 23
<212> TYPE: RNA
<213> ORGANISM: Mus musculus

<400> SEQUENCE: 78
uaagugcuuc cauguuuuag uag                                               23
```

```
<210> SEQ ID NO 79
<211> LENGTH: 23
<212> TYPE: RNA
<213> ORGANISM: Mus musculus

<400> SEQUENCE: 79
uaagugcuuc cauguuuugg uga                                              23

<210> SEQ ID NO 80
<211> LENGTH: 23
<212> TYPE: RNA
<213> ORGANISM: Mus musculus

<400> SEQUENCE: 80
ucaugucugu uagccagcac uuc                                              23

<210> SEQ ID NO 81
<211> LENGTH: 23
<212> TYPE: RNA
<213> ORGANISM: Mus musculus

<400> SEQUENCE: 81
ucaugucugu uagccaaagc uuc                                              23

<210> SEQ ID NO 82
<211> LENGTH: 26
<212> TYPE: RNA
<213> ORGANISM: Mus musculus

<400> SEQUENCE: 82
uuaguacagu auggaaagag cacuua                                           26

<210> SEQ ID NO 83
<211> LENGTH: 26
<212> TYPE: RNA
<213> ORGANISM: Mus musculus

<400> SEQUENCE: 83
uuaguacagu auggaaagaa agcuua                                           26

<210> SEQ ID NO 84
<211> LENGTH: 23
<212> TYPE: RNA
<213> ORGANISM: Mus musculus

<400> SEQUENCE: 84 uguuuguau cugauaaagc uug                                               23

<210> SEQ ID NO 85
<211> LENGTH: 28
<212> TYPE: RNA
<213> ORGANISM: Mus musculus

<400> SEQUENCE: 85
auauuagaau uucuaucuag ggcacuua                                         28

<210> SEQ ID NO 86
<211> LENGTH: 23
<212> TYPE: RNA
<213> ORGANISM: Mus musculus

<400> SEQUENCE: 86 uguuuguau cugauagcac uug                                               23
```

```
<210> SEQ ID NO 87
<211> LENGTH: 28
<212> TYPE: RNA
<213> ORGANISM: Mus musculus

<400> SEQUENCE: 87
auauuagaau uucuaucuag ggcccuua                                          28
```

MICRORNA INDUCTION OF CARDIAC REGENERATION

CROSS-REFERENCE TO RELATED APPLICATIONS

This application is a National Phase Application of PCT International Application No. PCT/US15/30990, International Filing Date May 15, 2015, claiming priority of Provisional Patent Application(s) No(s). 61/994,250, filed May 16, 2014, which are hereby incorporated by reference.

GOVERNMENT INTEREST

This invention was made with government support under Grant Numbers HL100405 and HL110942, awarded by the National Institutes of Health. The government has certain rights in the invention

FIELD OF THE INVENTION

The invention relates to compostions and methods for promoting cellular proliferation and de-differentiation of cells into stem cells to foster tissue regeneration. Specifically, the invention relates to transiently administering a microRNA (miR) or its mimic for promoting cardiomyocyte proliferation and cardiac regeneration.

BACKGROUND OF THE INVENTION

Historically, the adult mammalian heart has been considered a terminally differentiated organ with limited capacity to regenerate after injury. In contrast, recent evidence has shown that the neonatal heart can regenerate through increased cardiomyocyte proliferation. This ability to regenerate in response to injury ends by seven days after birth in mice, corresponding to the exit of cardiomyocytes from the cell cycle. Although there is some evidence for a very low level of postnatal cardiomyocyte proliferation which can be increased after injury, it is insufficient to replenish lost cardiomyocytes after injury and re-establish proper heart function. One important hurdle for cardiomyocytes to overcome in reentering the cell cycle is the rigidity of the sarcomere structure, which must be disassembled for cytokinesis to occur. Such disassembly may require signals for cardiomyocyte de-differentiation, which is accompanied by multiple cellular changes including reactivation of gene expression programs restricted to the embryonic state. Thus, approaches that reactivate or increase postnatal cardiomyocyte proliferation could have a positive affect on cardiac repair and regeneration but their persistence would need to be carefully tuned to avoid cardiomyocyte dysfunction associated with a highly proliferative, de-differentiated state.

MicroRNAs (miRs) can have potent affects on gene expression and can alter cell phenotype by coordinately targeting multiple components in important cellular pathways. Several miR cluster or families are expressed in early development and play important roles in maintaining tissue specific progenitor identity. One such cluster, miR302-367, is expressed during early embryogenesis in embryonic stem cells and in the developing lung endoderm where it promotes a de-differentiated phenotype characterized by high levels of cell proliferation.

Accordingly, a need exists to understand the mechanisms of miR302-367, and thereby develop improved miRNA-based compositions and methods.

SUMMARY OF THE INVENTION

In one aspect, provided herein are methods for promoting cellular proliferation and de-differentiation of cells into stem cells for cardiac tissue regeneration, the methods comprising: transiently contacting said cells with a composition comprising a microRNA (miR) 302-367 cluster or a miR 302-367 cluster mimic. In an exemplary embodiment, the transient contact is sufficient to transiently activate cardiomyocyte proliferation, but not to reactivate the cell cycle of postnatal cardiomyocytes.

In another aspect, provided herein are methods for promoting cardiac repair and regeneration in a subject, the methods comprising: transiently administering to said subject a composition comprising a microRNA (miR) 302-367 cluster or a miR 302-367 cluster mimic.

In another aspect, provided herein are methods for promoting cardiomyocyte proliferation in a subject, the methods comprising: transiently administering to said subject a composition comprising a microRNA (miR) 302-367 cluster or a miR 302-367 cluster mimic.

In another aspect, provided herein are methods for treating a cardiac disease or disorder in a subject, the methods comprising: transiently administering to said subject a composition comprising a microRNA (miR) 302-367 cluster or a miR 302-367 cluster mimic.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will be better understood from a reading of the following detailed description taken in conjunction with the drawings.

High-magnification reveals PH3+ cardiomyocytes. LA, left atrium. Data are means±SEM (n=3). P values determined by Student's t test.

Figure 3:
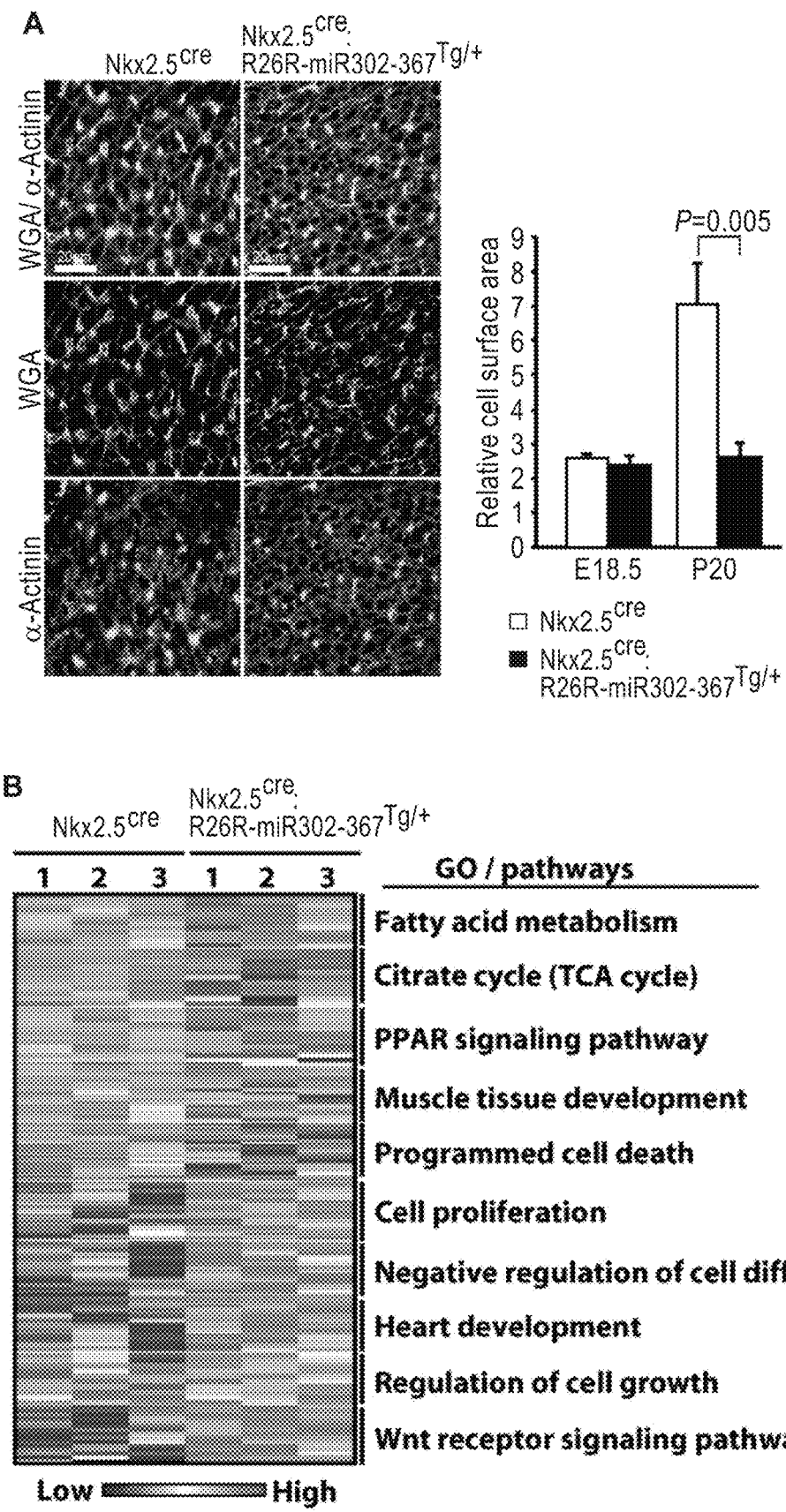
Figure 3:
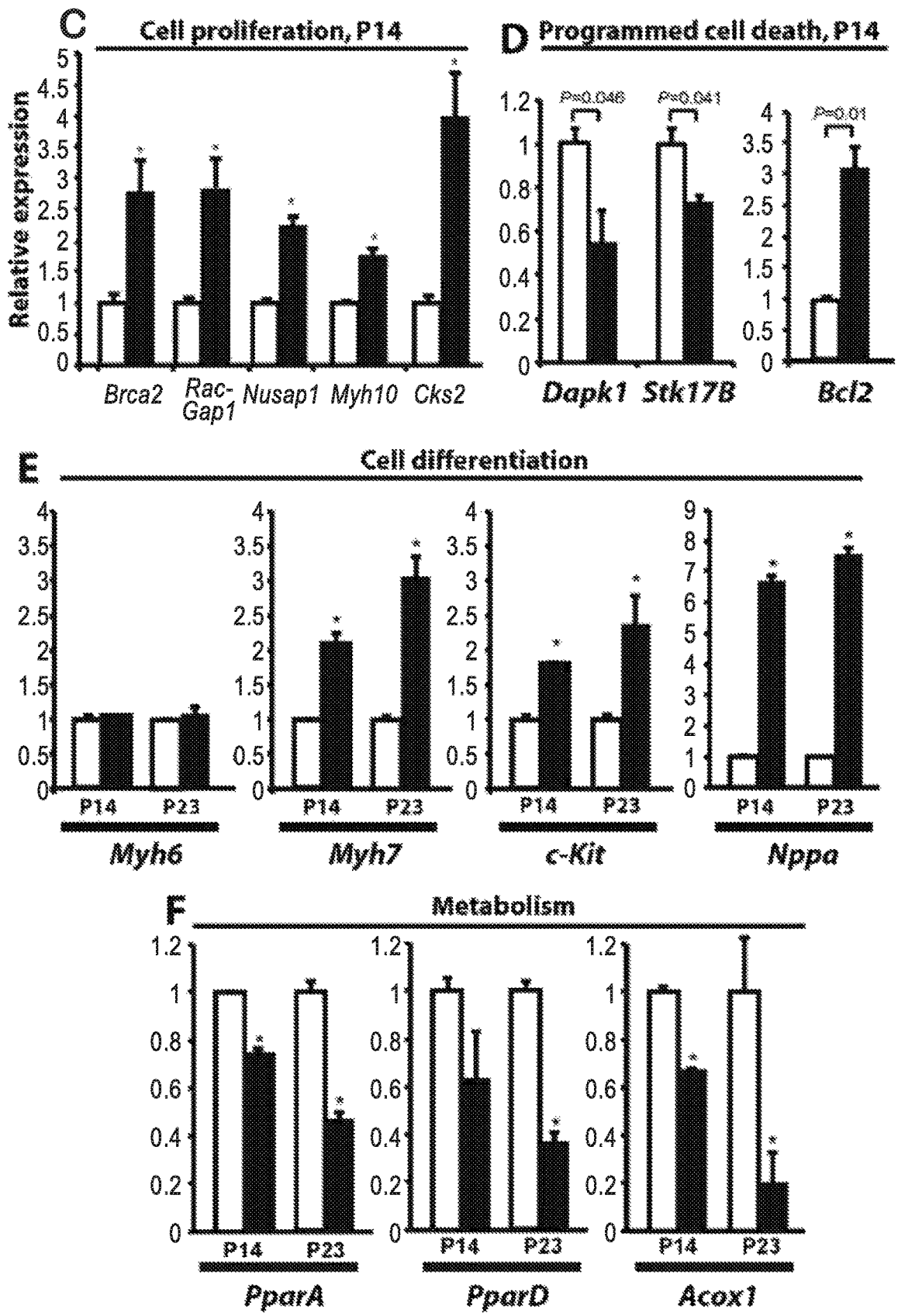

FIG. 3. miR302-367 over-expression leads to increased cell proliferation as well as altered differentiation and metabolism in cardiomyocytes. (A) Wheat germ agglutinin and α-actinin staining of hearts at P20. Cell surface area was quantified at E18.5 and P20. Quantitative analyses represent counting of five fields from three independent samples per group. (B) Heatmap and pathways profile of microarray analysis of Nkx2.5$^{cre}$ and Nkx2.5$^{cre}$:R26R-miR302-367$^{Tg/+}$ mutant hearts at P14. (C and D) Gene expression changes related to cell proliferation (C) and programmed cell death (D) at P14. (E and F) Gene expression changes related to differentiation (E) and fatty acid metabolism (F) at P14 and P23. Data are means±SEM (n=3 per group). *P<0.05 versus Nkx2.5$^{cre}$ control animals (Student's t test).

Figure 4:
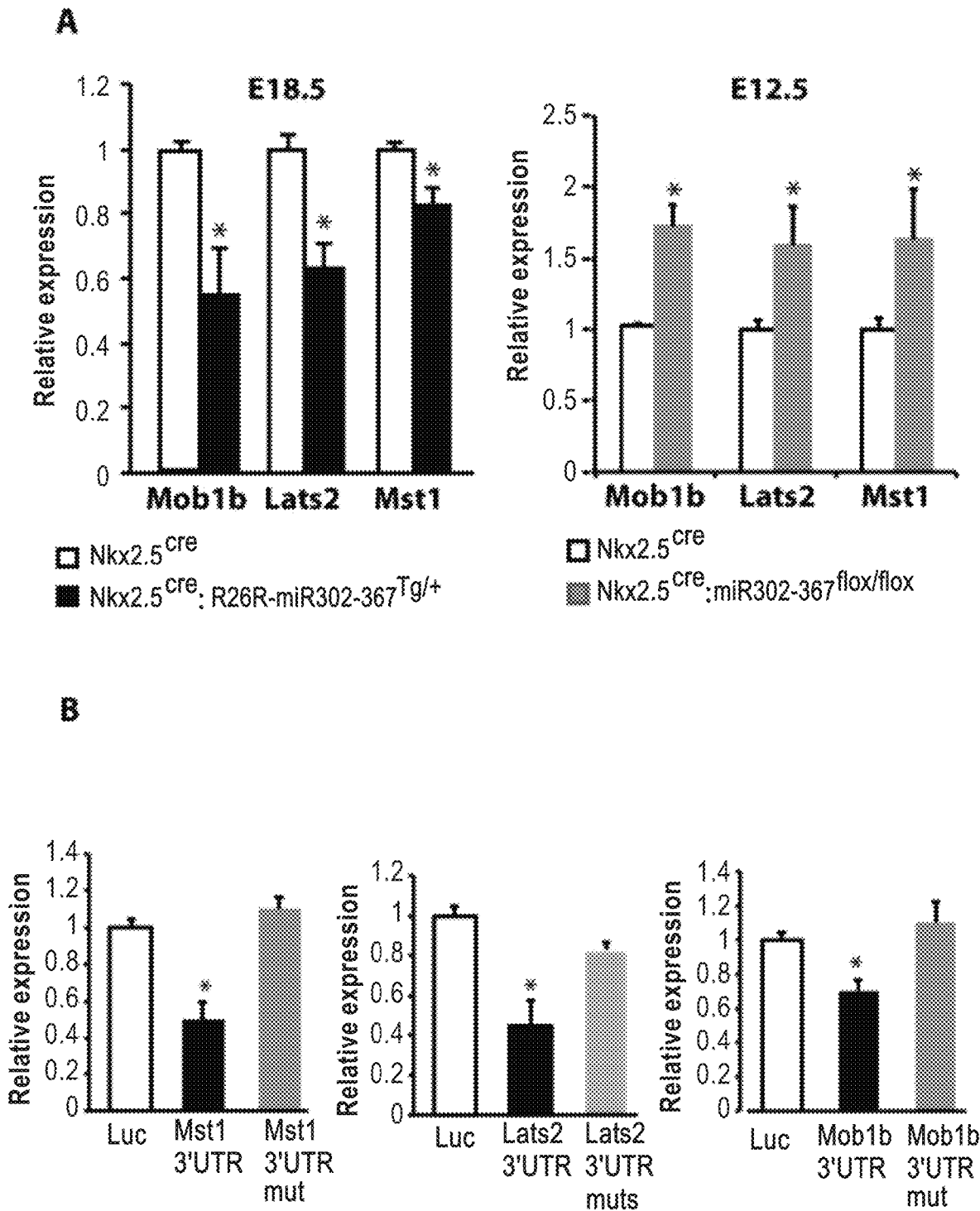
Figure 4:
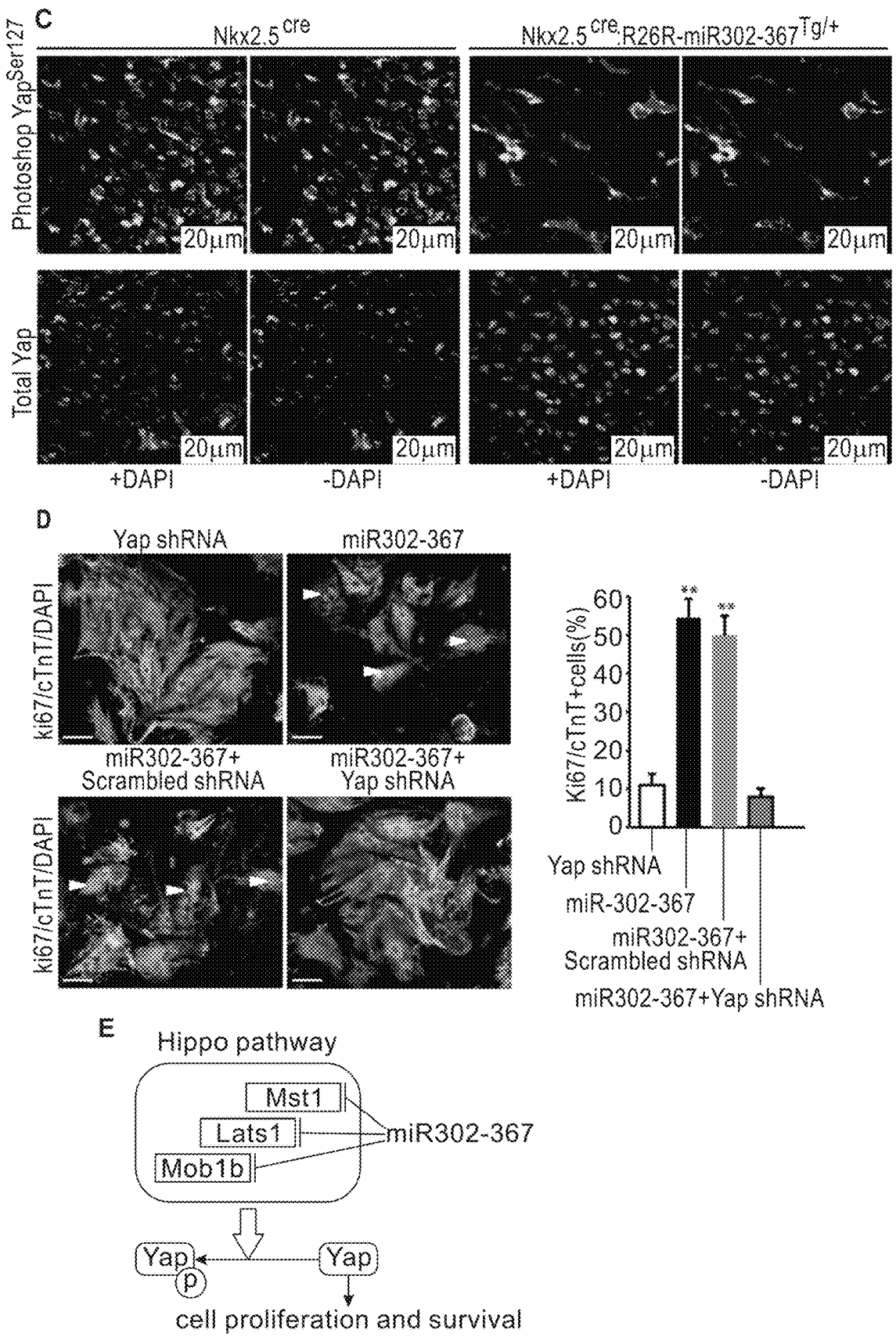

FIG. 4. miR302-367 promotes cardiomyocyte proliferation through regulation of Hippo pathway kinases. (A) Expression of Mob1b, Lats2, and Mst1 in Nkx2.5$^{cre}$:R26R-miR302-367$^{Tg/+}$ mutant hearts at E18.5 and Nkx2.5$^{cre}$:R26R-miR302-367$^{flox/flox}$ null mutant hearts at E12.5 by qRT-PCR. (B) Luciferase reporter assays showing that miR302-367 can repress Mst1, Lats2, and Mob1b expression through their respective 3'UTRs. This repression can be reversed by mutations of the miR302-367 binding sites. (C) Confocal fluorescence microscopy of phospho-Yap and nuclear staining of Yap, with or without DAPI, in ventricular cardiomyocytes of Nkx2.5$^{cre}$:R26R-miR302-367$^{Tg/+}$ mouse hearts at E18.5. Cytoplasmic and nuclear ratio for total Yap protein was quantified using Fiji software. (A to C) *P<0.05, P<0.01 versus Nkx2.5cre control hearts (Student's t test). (D) Overexpression of miR302-367 in primary mouse neonatal cardiomyocytes. Cardiomyocyte proliferation was quantified using Ki67 immunostaining. P<0.01 versus Yap shRNA control. Scale bars, 100 mm. (E) Proposed model of miR302-367 promoting cardiomyocyte proliferation through regulation of Hippo pathway kinases. (A to D) Data are means±SEM (n=3 for A, C, and D; n=5 for B).

Figure 5:
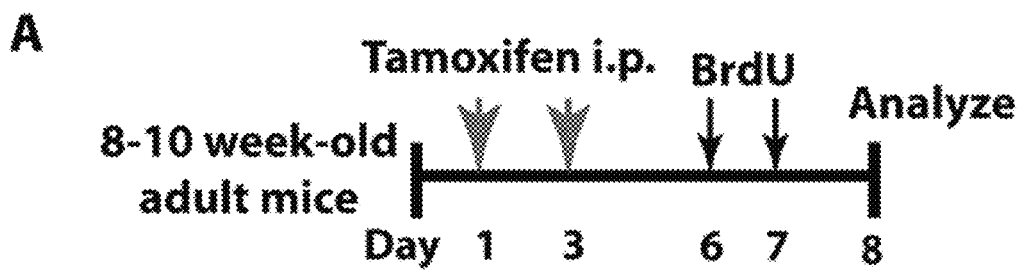
Figure 5:
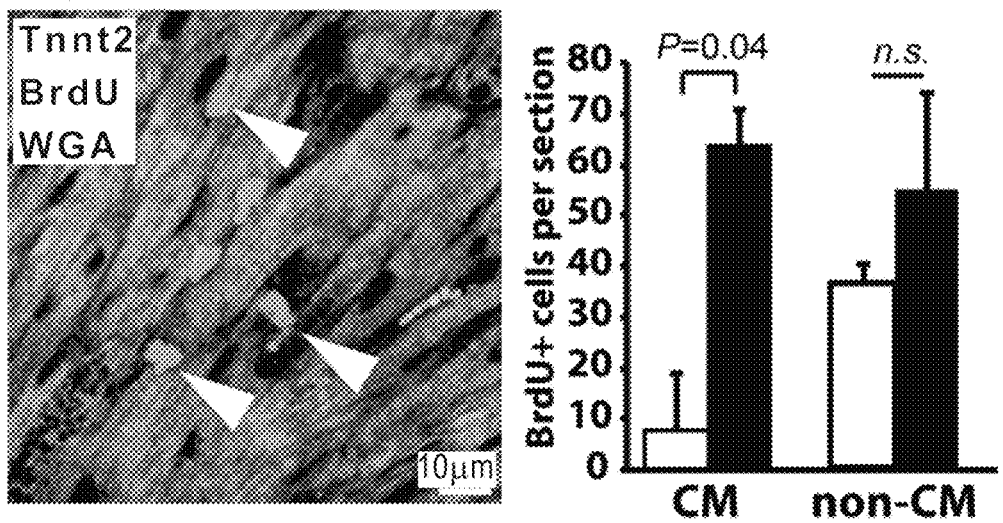
Figure 5:
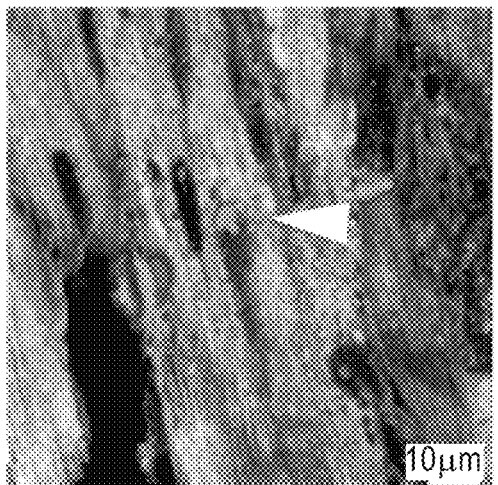
Figure 5:
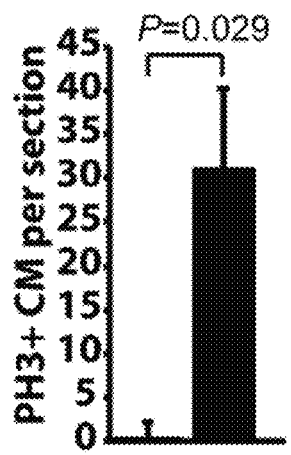
Figure 5:
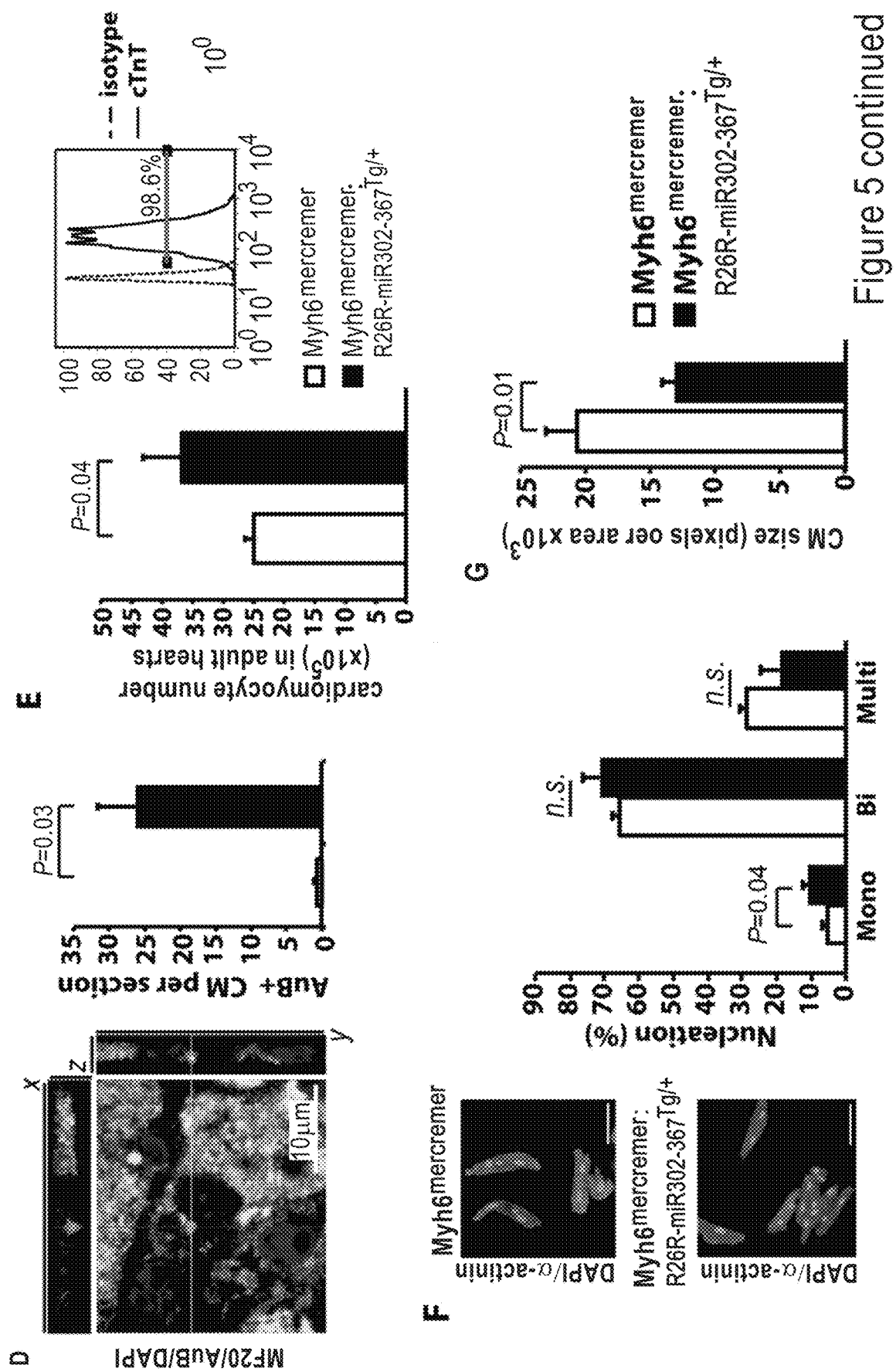

FIG. 5. miR302-367 can promote cardiomyocyte proliferation in the adult heart. (A) Schematic of inducible miR302-367 over-expression in adult heart using Myh6$^{mercremer}$ mice. (B to D) Confocal images with z-stacking and quantification showing the number of cells reentering the cell cycle [5-bromo-2'-deoxyuridine (BrdU)+] (B), undergoing mitosis (PH3+) (C), or undergoing cytokinesis [Aurora B (AuB)+] (D) 7 days after induction of miR302-367 expression in the adult heart. (E) Number of cardiomyocytes in Myh6$^{mercremer}$ and Myh6$^{mercremer}$:R26R-miR302-367$^{Tg/+}$ animals. Inset: Fluorescence-activated cell sorting (FACS) plot shows that 98.6% of the isolated cells counted in the adult hearts are cTnT+ cardiomyocytes. (F) Number of nuclei in control and Myh6$^{mercremer}$:R26R-miR302-367$^{Tg/+}$ cardiomyocytes. Scale bars, 100 mm. mono, mononucleated; bi, binucleated; multi, multinucleated About 1×103 cardiomyocytes were counted per sample. (G) Cell sizes of the isolated cardiomyocytes. Data are means±SEM (n=3). P values determined with Student's t test. n.s., no significant change.

Figure 6:
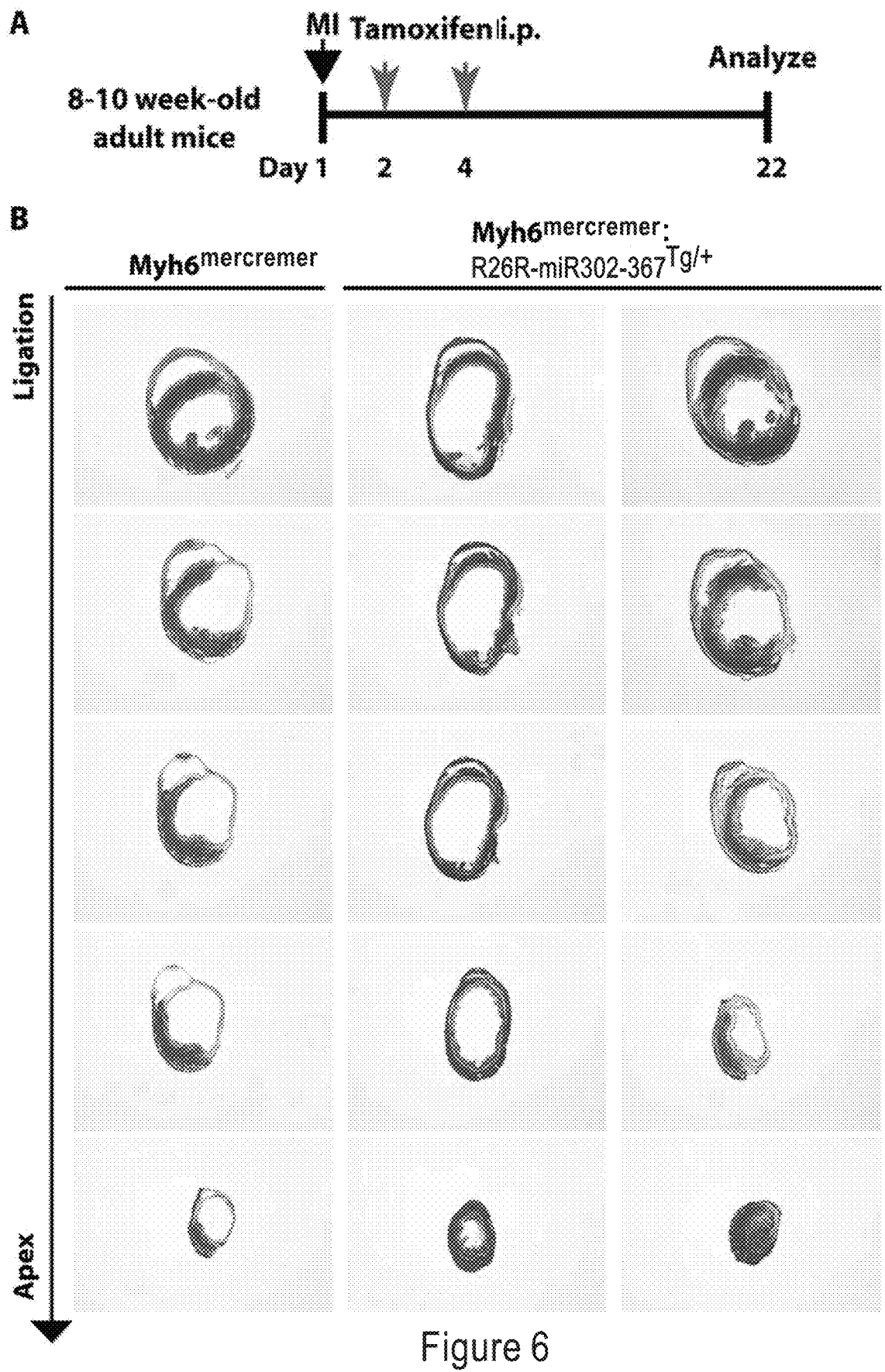
Figure 6:
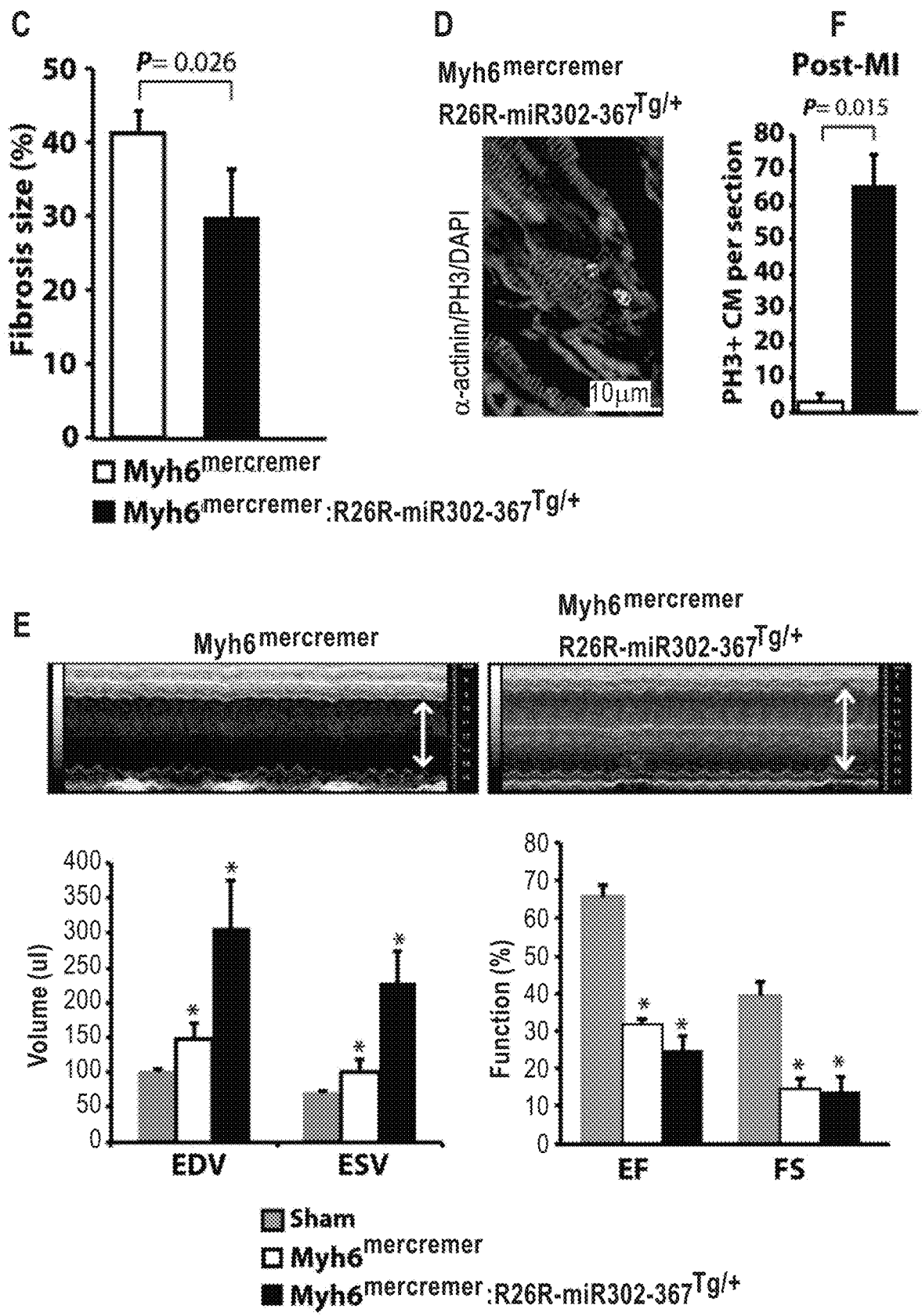

FIG. 6. Prolonged miR302-367 overexpression in the adult heart reduces fibrotic scar size but compromises cardiac function after myocardial infarction (MI). (A) Study design of miR302-367 overexpression by tamoxifen intraperitoneal injection after MI by ligation of the left anterior descending (LAD) coronary artery. (B) Masson's trichrome-stained heart sections from the site of ligation toward the apex of control and Myh6$^{mercremer}$:R26R-miR302-367$^{Tg/+}$ mice at 21 days after MI. Serial sections were cut at 500-mm intervals from the site of the ligature toward the apex. One representative Myh6$^{mercremer}$ and two Myh6$^{mercremer}$:R26RmiR302-367$^{Tg/+}$ hearts are shown (n=6 per group). (C) Quantification of the fibrotic regions in heart sections in (B). (D) Immunostaining and quantification of PH3+/α-actinin+ cells in Myh6$^{mercremer}$ and Myh6$^{mercremer}$:R26R-miR302-367$^{Tg/+}$ hearts at 21 days after MI. (E) Cardiac function in mice subjected to LAD ligation, evaluated by echocardiography (n=7 per group). EF, ejection fraction; FS, fractional shortening; EDV, end-diastolic volume; ESV, end-systolic volume. Data are means±SEM (n=6 to 7). (C and D) P values determined with Student's t test. (E) *P<0.05 versus sham, by one-way analysis of variance (ANOVA).

Figure 7:
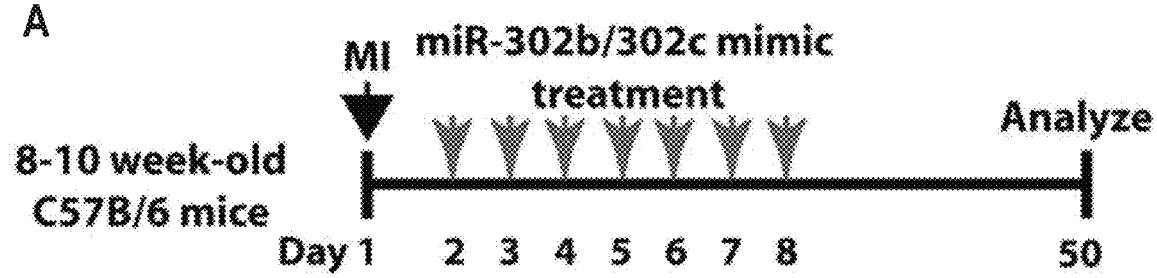
Figure 7:
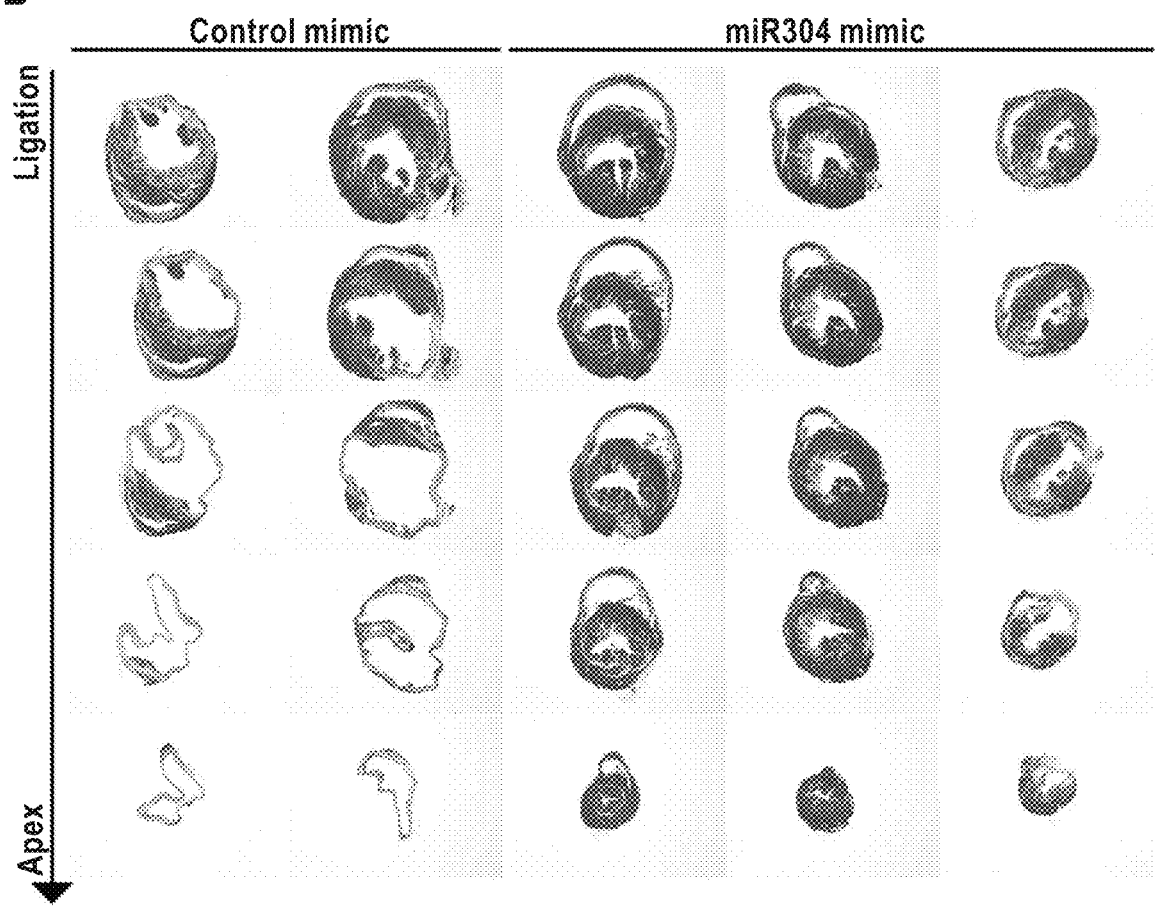
Figure 7:
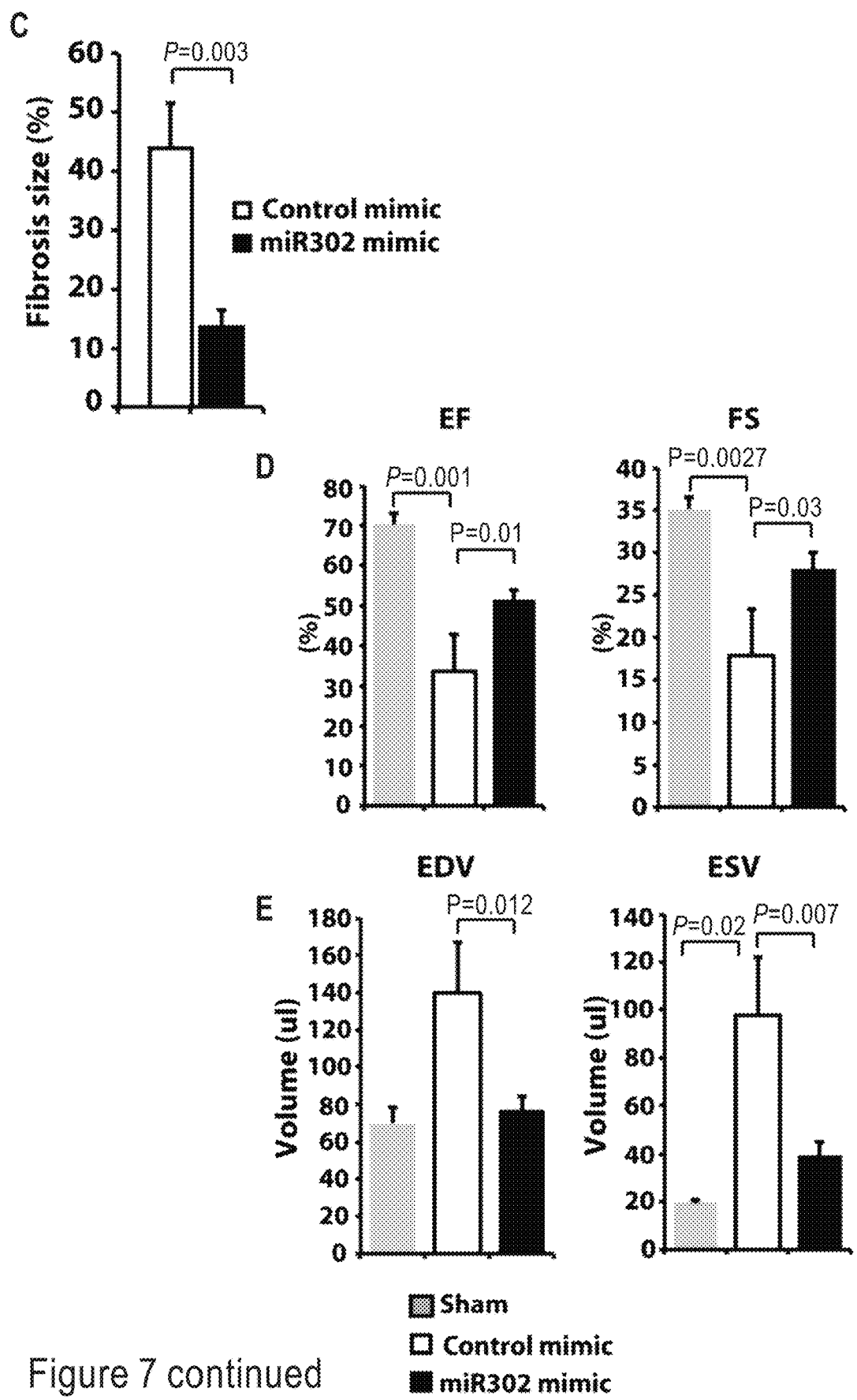

FIG. 7. Transient miR302 mimic therapy promotes cardiac regeneration and improves function of injured hearts. (A) Schematic of 7-day miR302 mimic treatment after MI (n=3 sham; n=8 control; n=18 miR302). (B) Masson's trichrome staining of heart sections 50 days after MI and 42 days after final treatment with control or miR302 mimic. Serial sections were cut at 500-mm intervals from the site of the ligature toward the apex. Two representative control and three miR302 mimic-treated hearts are shown. (C) Quantification of the fibrotic areas in heart sections. Data are means±SEM. (D and E) Cardiac function of mice subjected to LAD ligation was evaluated by echocardiography. Data are means±SEM. P values determined by one-way ANOVA.

Figure 8:
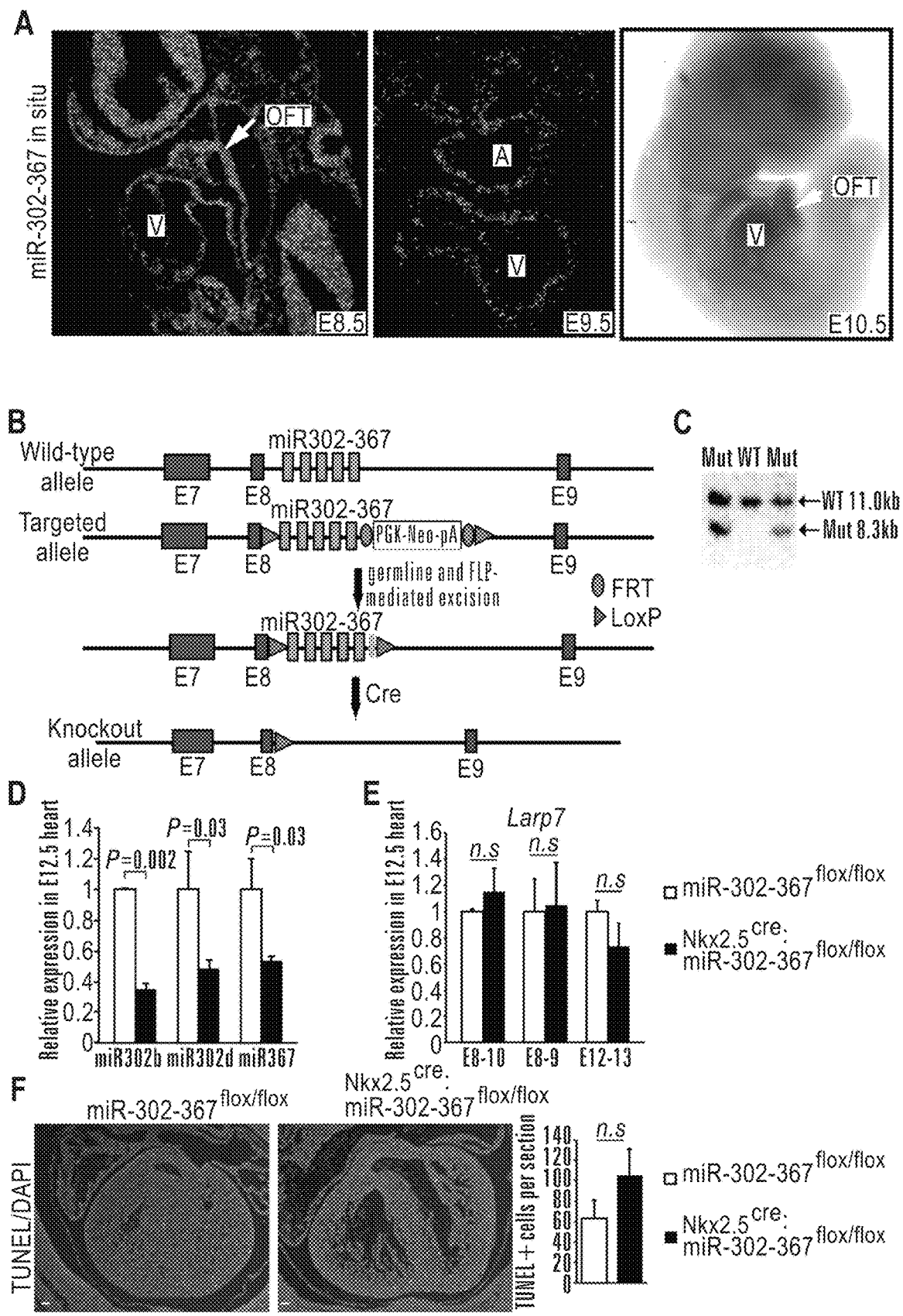

FIG. 8. Generation of mice with a conditional deletion of the miR302-367 cluster. (A) In situ hybridization showing the miR302-367 cluster expressed in the developing mouse myocardium at E8.5, E9.5, and E10.5. Arrowheads indicate the miR302-367 cluster in the outflow tract (OFT) of the developing heart. A, atrium; V, ventricle. (B) Schematic representation of the mouse miR302-367 locus and the targeting strategy for deletion of miR302-367. (C) Southern blot analysis of crosses of Nkx2.5$^{cre}$:miR302-367$^{flox/+}$ and wild-type mice. (D) Expression of members of the miR302-367 cluster in Nkx2.5$^{cre}$:miR302-367$^{flox/flox}$ null mutant hearts at E12.5. (E) The expression of host gene Larp7 in Nkx2.5$^{cre}$:miR302-367$^{flox/flox}$ null mutant hearts at E12.5. qRT-PCR used primers spanning exons 8 and 9 and exons 8 and 10 of Larp7, showing normal splicing across the targeted region. Primers targeted at the 3' region of the mRNA locus (exons 12 and 13) showed intact transcription of Larp7. (F) Apoptosis analysis by TUNEL staining of hearts at E14.5. DAPI indicates cell nuclei. Scale bars, 100 μm. Data in (E and F) are means±s.e.m. (n=3). P values determined by Student's t test. n.s., not significant.

Figure 9:
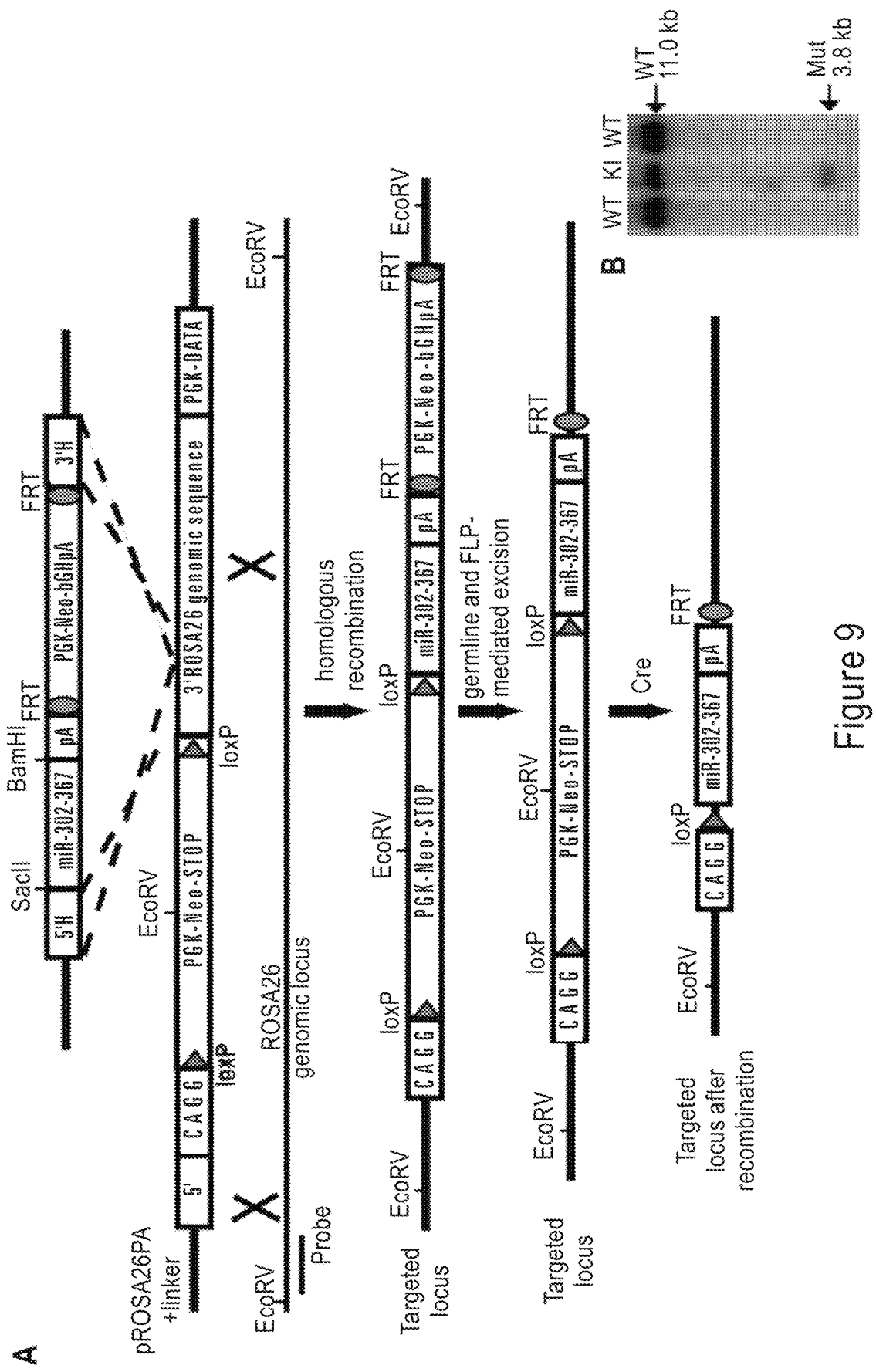
Figure 9:
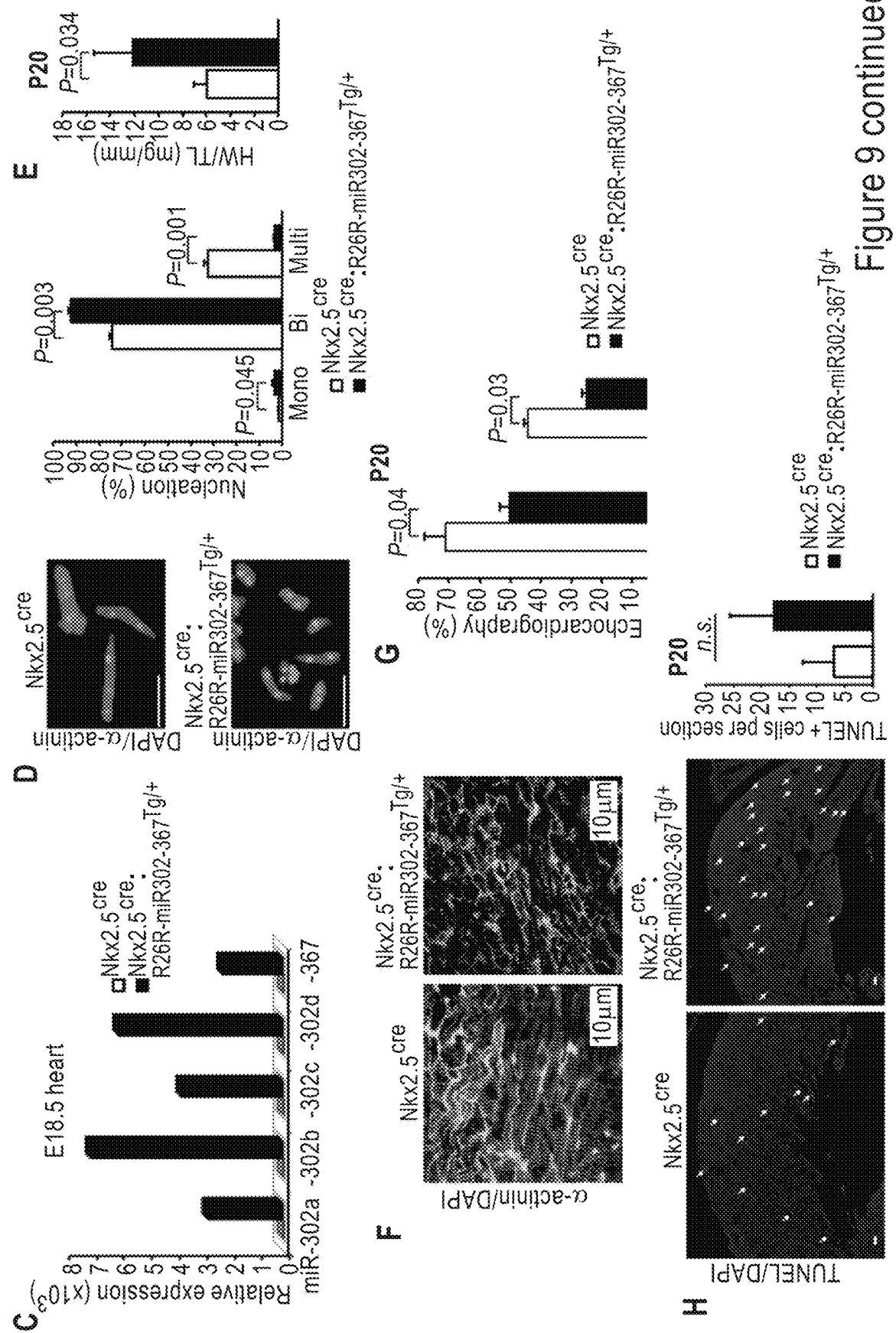

FIG. 9. Generation of mice with conditional over-expression of the miR302-367 cluster. (A) Schematic of the floxed miR302-367 knock-in allele and the targeting strategy for Cre-activated over-expression of miR302-367. (B) Southern blot analysis of wild-type (11 kb) and R26R-miR302-367 knock-in (3.8 kb) mice after digestion of genomic DNA with EcoRV. (C) qRT-PCR showing specific over-expression of all members of miR302-367 family in Nkx2.5$^{cre}$:R26R-miR302-367$^{Tg/+}$ hearts at E18.5. (D) Quantification of the number of nuclei in Nkx2.5$^{cre}$ and Nkx2.5$^{cre}$:R26R-miR302-367$^{Tg/+}$ heart at P17. (E) Heart weight-to-tibia length (HW/TL) ratios at P20. (F) Immunostaining of cardiomyocytes with α-actinin shows sarcomeric structures at P20. (G) Cardiac function P20 was evaluated by echocardiography. EF, ejection fraction; FS, fractional shortening. (H) Immunostaining for TUNEL and DAPI on hearts at P20. Data are means±s.e.m. P values determined by Student's t test. Scale bars in (D and H), 100 μm.

Figure 10:
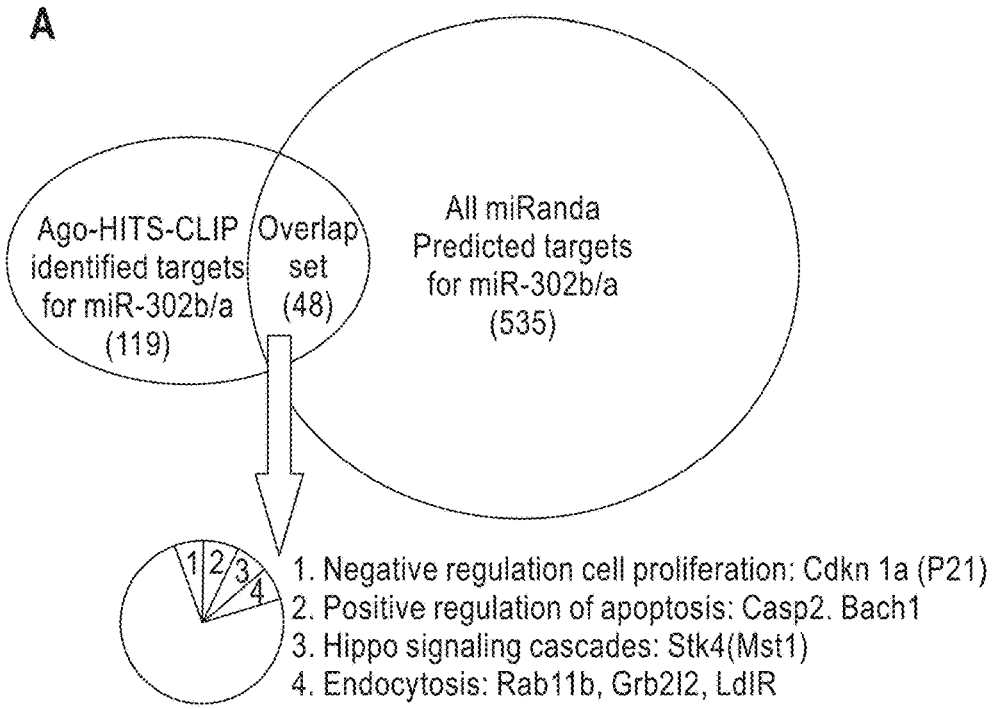
Figure 10:
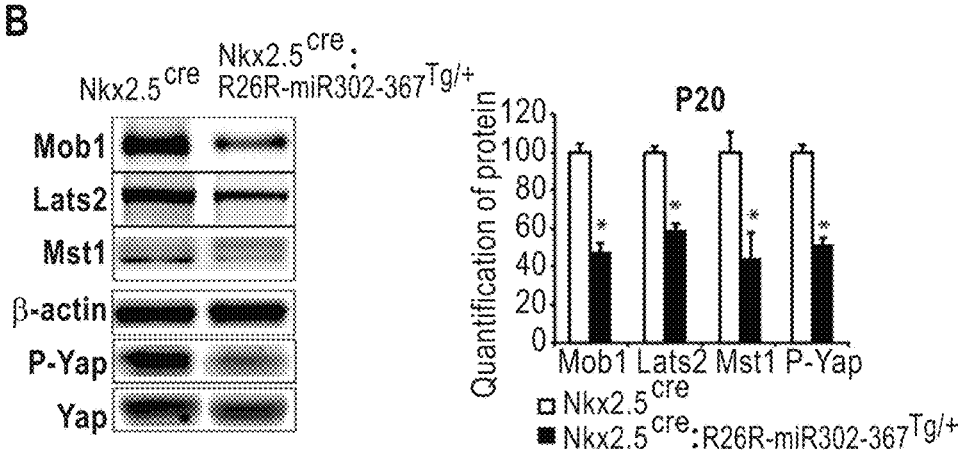
Figure 10:
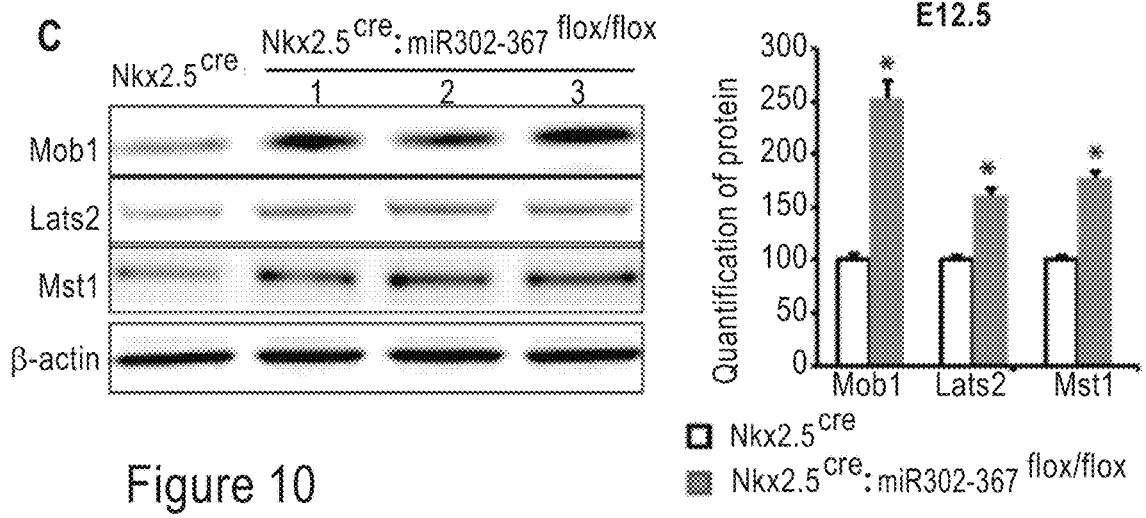
Figure 10:
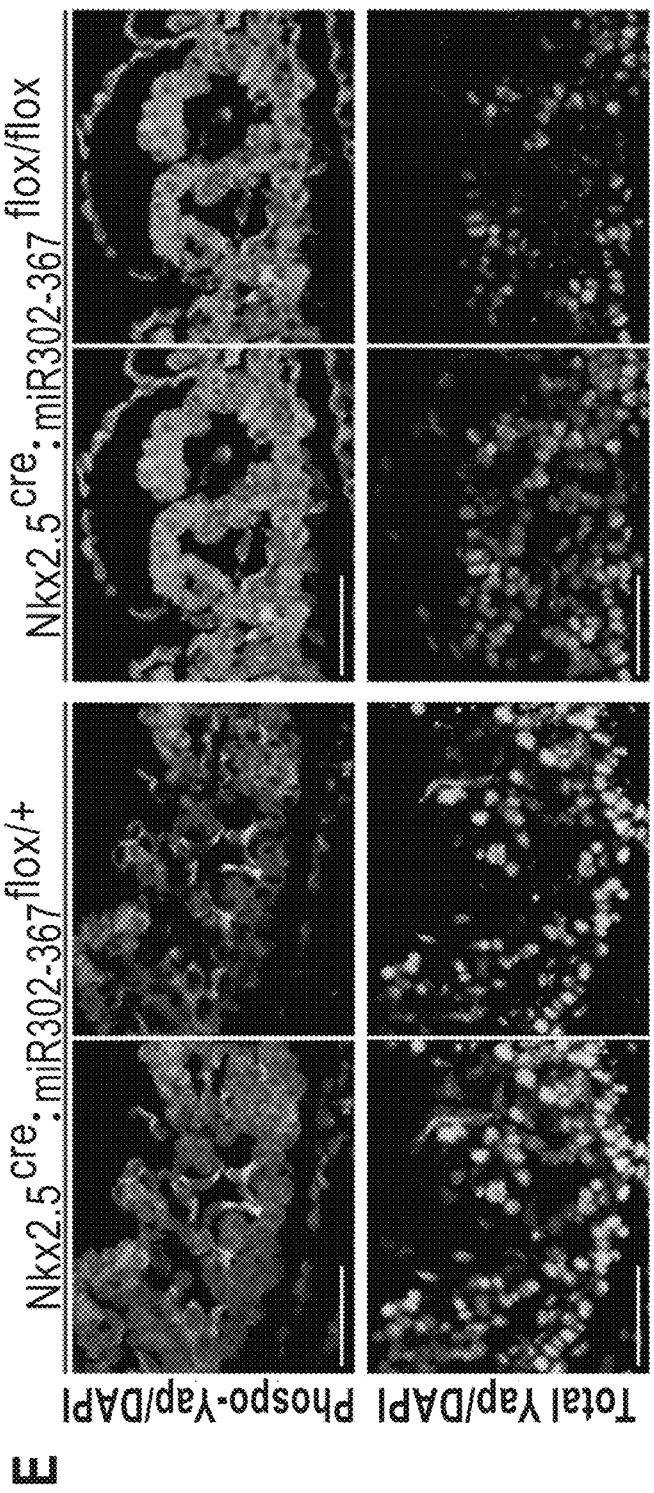
Figure 10:
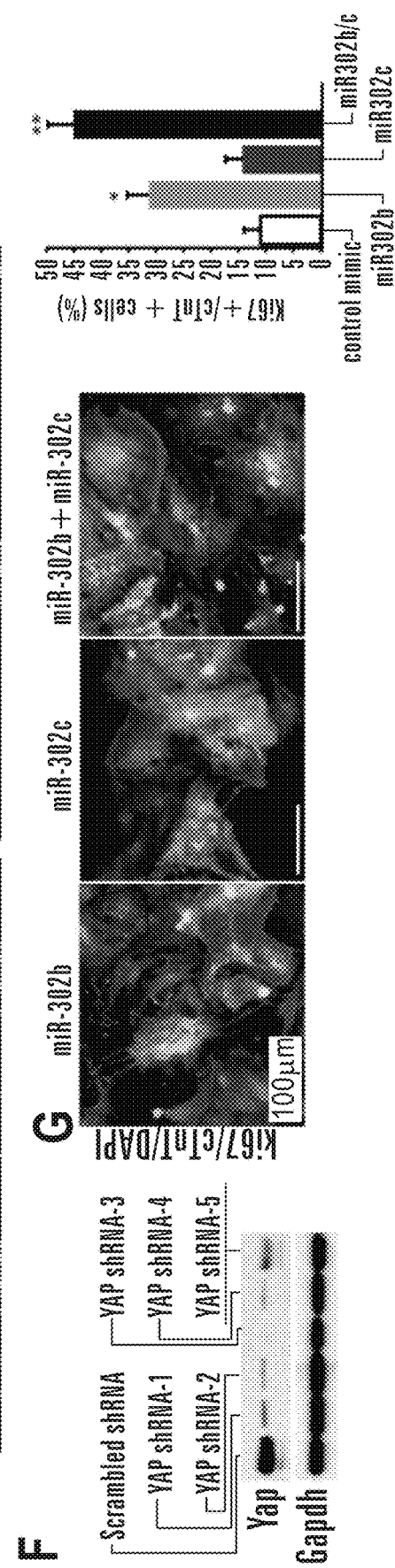

FIG. 10. miR302-367 regulates cardiomyocyte proliferation through Hippo pathway. (A) Multiple targets of miR302 were identified by comparing Ago-HITS-CLIP and miRanda predicted targets. (B) Western blot analysis of Mob1, Lats2, Mst1 and P-Yap protein level in Nkx2.5$^{cre}$:R26R-miR302-367$^{Tg/+}$ hearts at P20. (C) Western blot analysis of Mob1, Lats2, and Mst1 in Nkx2.5$^{cre}$:R26R-miR302-367$^{flox/flox}$ hearts at E12.5. Data in (B and C) are means±s.e.m. (n=3). *p<0.05 versus Nkx2.5$^{cre}$, by Student's t test. (D) 3'UTR sequence information of Mst1 (SEQ ID NO: 80), Mst1-mut (SEQ ID NO: 81), Lats2 (partial; SEQ ID NO: 82), Lats2-mut1 (SEQ ID NO: 83), Lats2 (partial; SEQ ID NO: 86), Lats2-mut2 (SEQ ID NO: 84), Mob1b (SEQ ID NO: 85), Mob1b-mut (SEQ ID NO: 87) and miR binding site mutations (miR-302a—SEQ ID NO: 79, miR-302-b SEQ ID NO: 78, miR-302-c SEQ ID NO: 77, miR-302-d SEQ ID NO: 76). (E) Immunostaining of phospho-Yap and nuclear Yap, with or without DAPI, in the cardiomyocytes of Nkx2.5$^{cre}$:R26R-miR302-367$^{flox/flox}$ hearts at E10.5. Scale bars, 100 μm. (F) Western blot analysis of Yap protein in neonatal cardiomyocytes 48 h after Yap shRNA lentivirus treatment. Yap shRNA-3 was used in subsequent experiments. (G) Over-expression of individual miRNAs in primary mouse neonatal cardiomyocytes using miRNA mimics. Proliferation was quantified by Ki67 immunostaining. Data are means±s.e.m. (n=3). *P<0.05, **P<0.01, versus control mimic, by one-way ANOVA.

Figure 11:
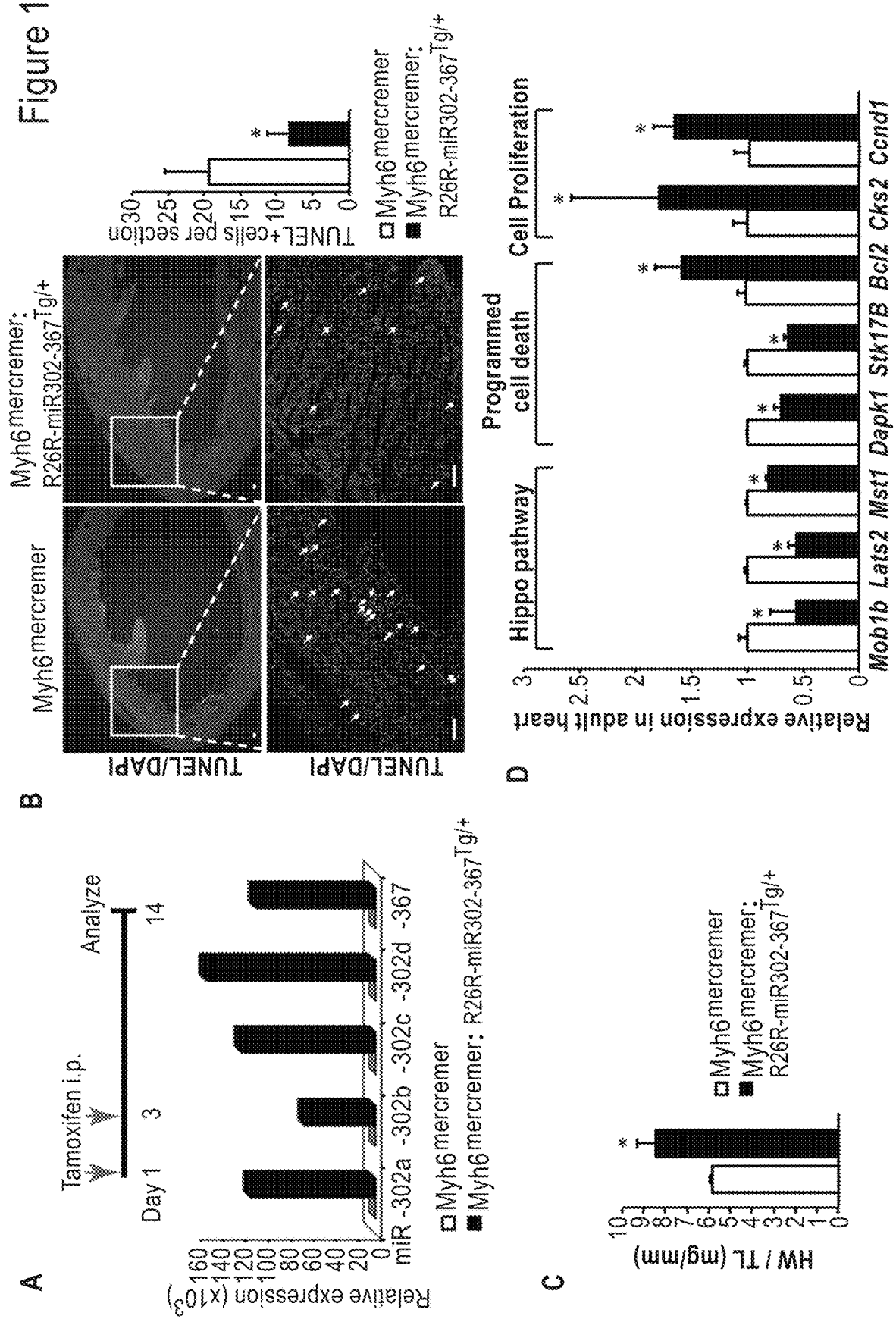

FIG. 11. Gene expression profiles in adult hearts following inducible over-expression of miR302-367. (A) Schematic of induced miR302-367 over-expression in adult heart using Myh6$^{mercremer}$ mice, and expression levels of all members of the miR302-367 cluster in Myh6$^{mercremer}$:R26R-miR302-367$^{Tg/+}$ adult hearts by qRT-PCR two weeks after Cre induction with tamoxifen. (B) Immunostaining and quantification of TUNEL and DAPI in adult hearts two weeks after Cre induction with tamoxifen. Scale bars, 100 μm. (C) Heart weight-to-tibia length (HW/TL) ratios 2 weeks after tamoxifen administration. (D) Differential gene expression in Myh6$^{mercremer}$:R26R-miR302-367$^{Tg/+}$ hearts two weeks after Cre induction. Data in (B to D) are means±s.e.m. (n=3). *p<0.05 versus Myh6$^{mercremer}$ control, by Student's t test.

Figure 12:
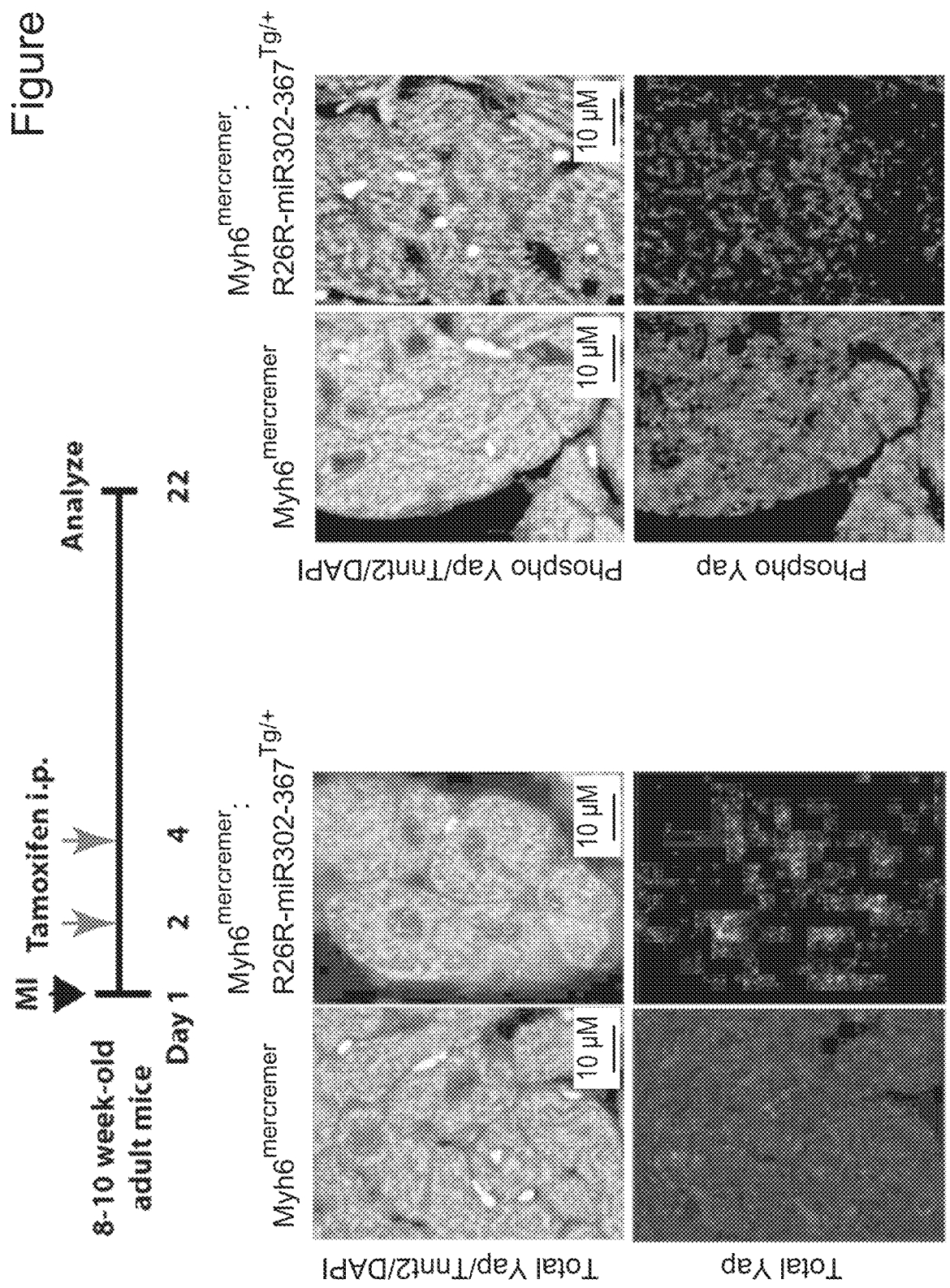
Figure 12:
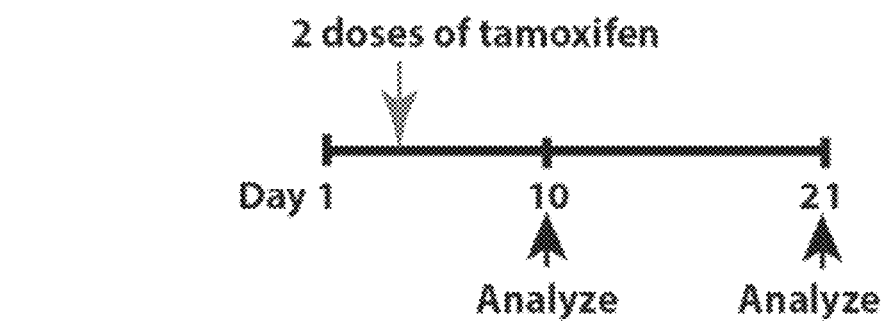
Figure 12:
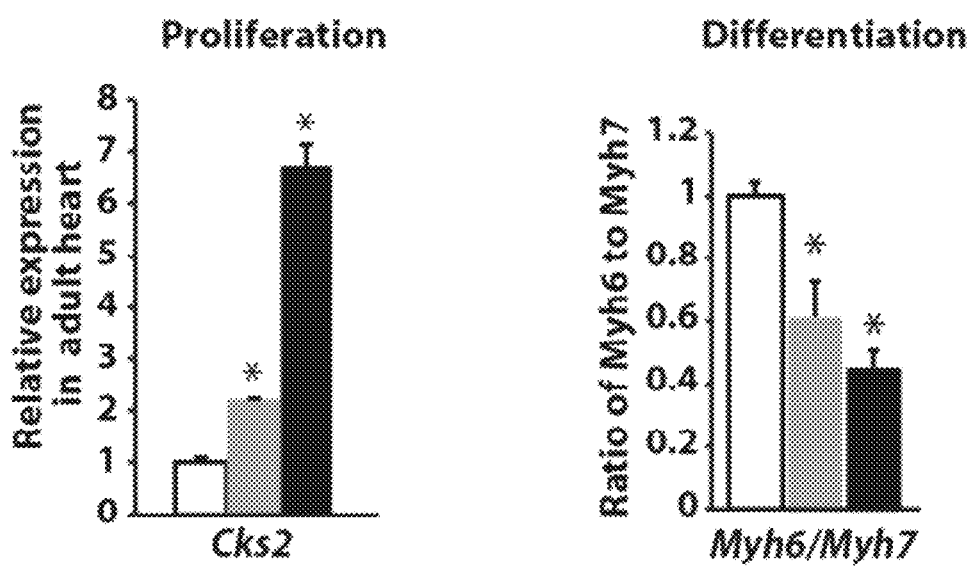
Figure 12:
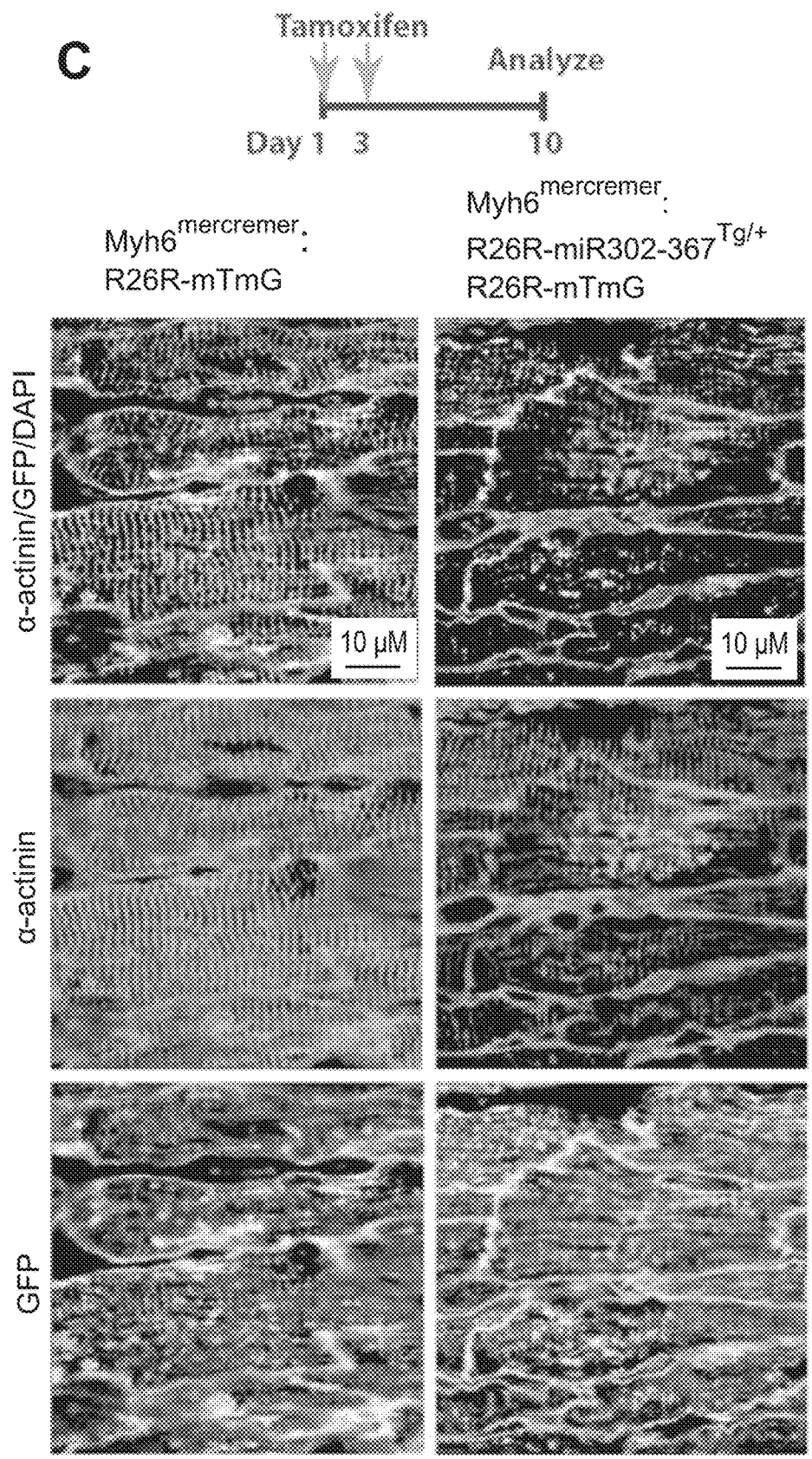

FIG. 12. Hippo signaling activity and myocardial features in adult heart following inducible over-expression of miR302-367. (A) Nuclear and phospho-Yap staining in ventricular cardiomyocytes after MI. (B) Differential expression of genes related to cell proliferation (Cks2) and maturation and dysfunction (ratio of Myh6 to Myh7) at early (day 10) and later (day 21) time points after Cre induction in Myh6$^{mercremer}$:R26R-miR302-367$^{Tg/+}$ hearts. Data are means±s.e.m. (n=6). *P<0.05 versus Myh6$^{mercremer}$ control, by one-way ANOVA. (C) α-Actinin staining reveals reduced sarcomeric protein expression and disorganized sarcomeric structure in the myocardial lineage positive cells (GFP+) in the Myh6$^{mercremer}$:R26R-miR302-367$^{Tg/+}$ line.

Figure 13:
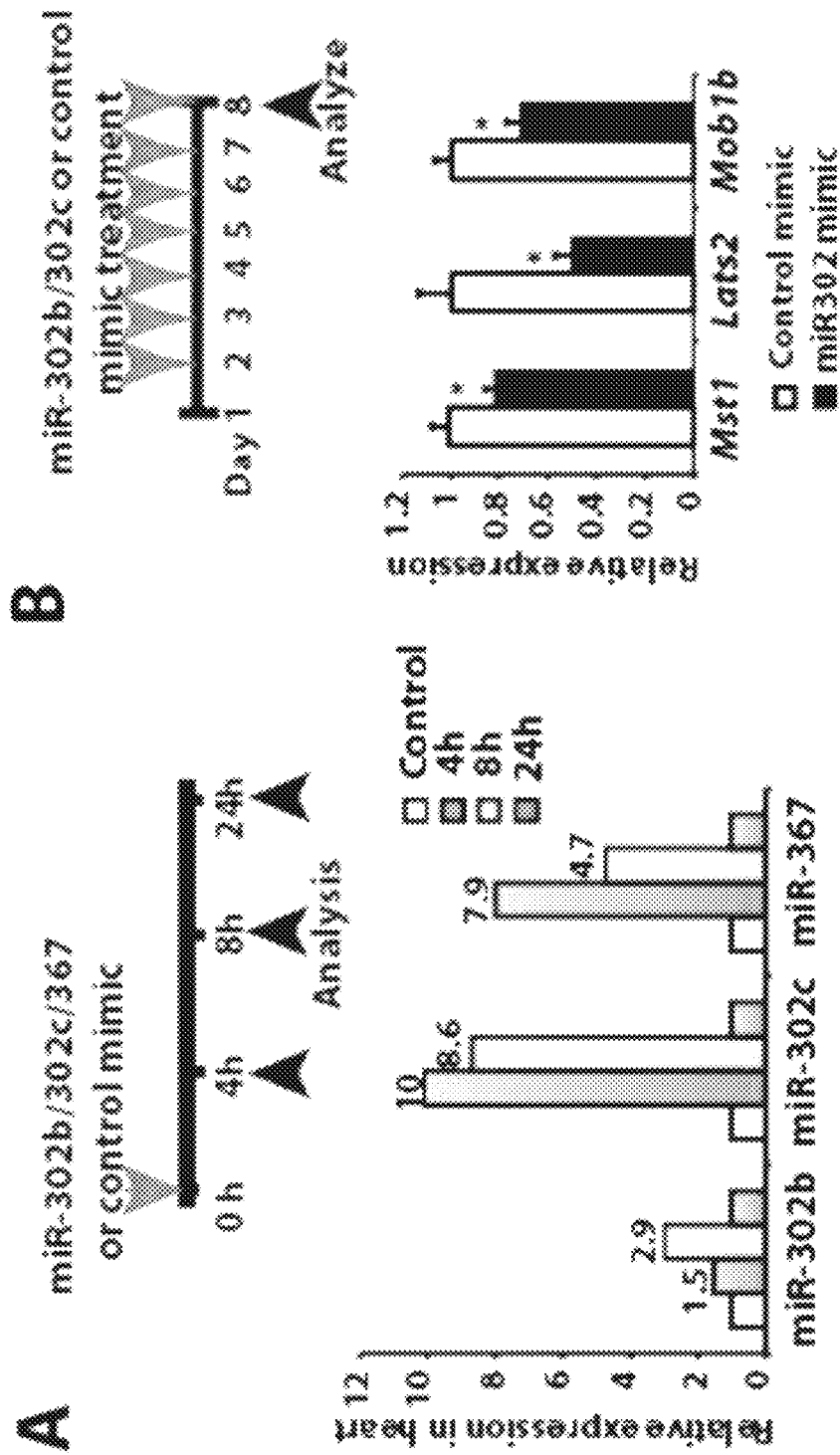
Figure 13:
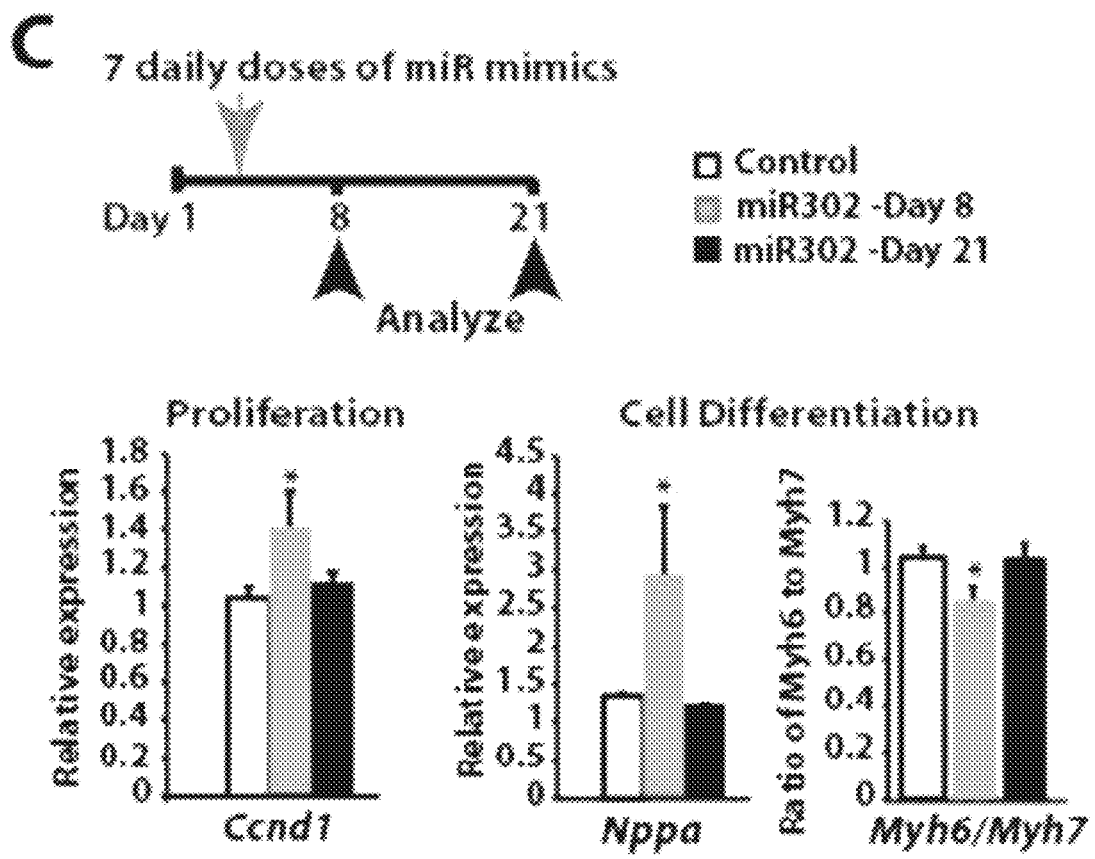
Figure 13:
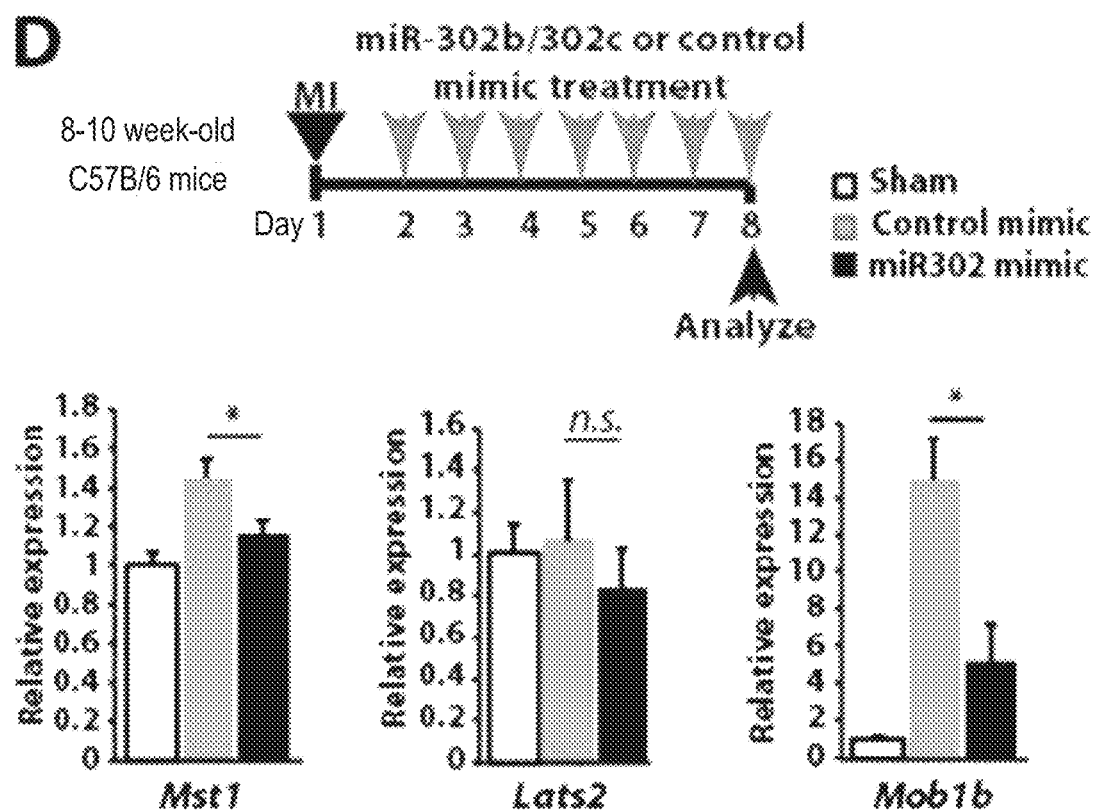
Figure 13:
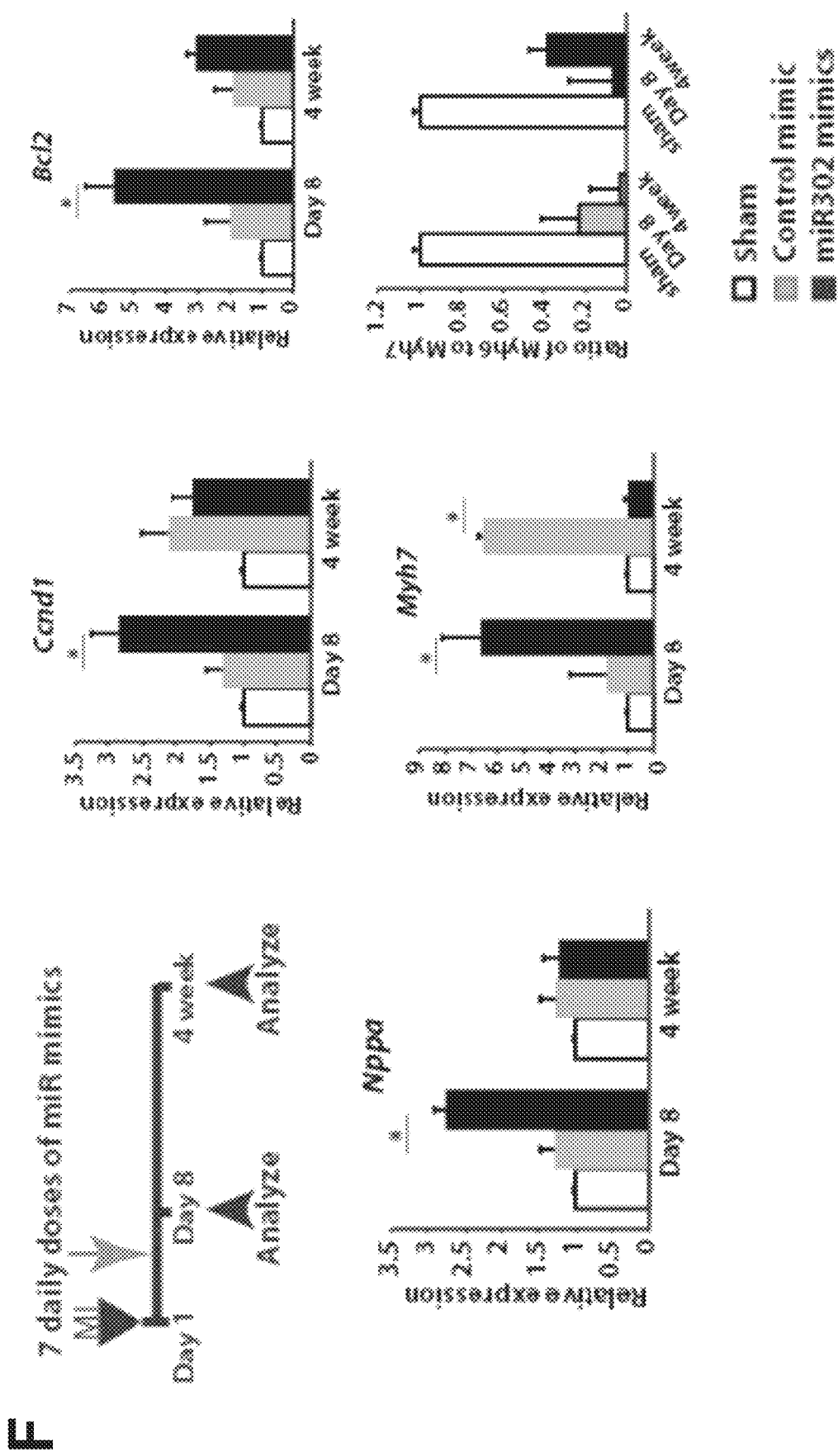
Figure 13:
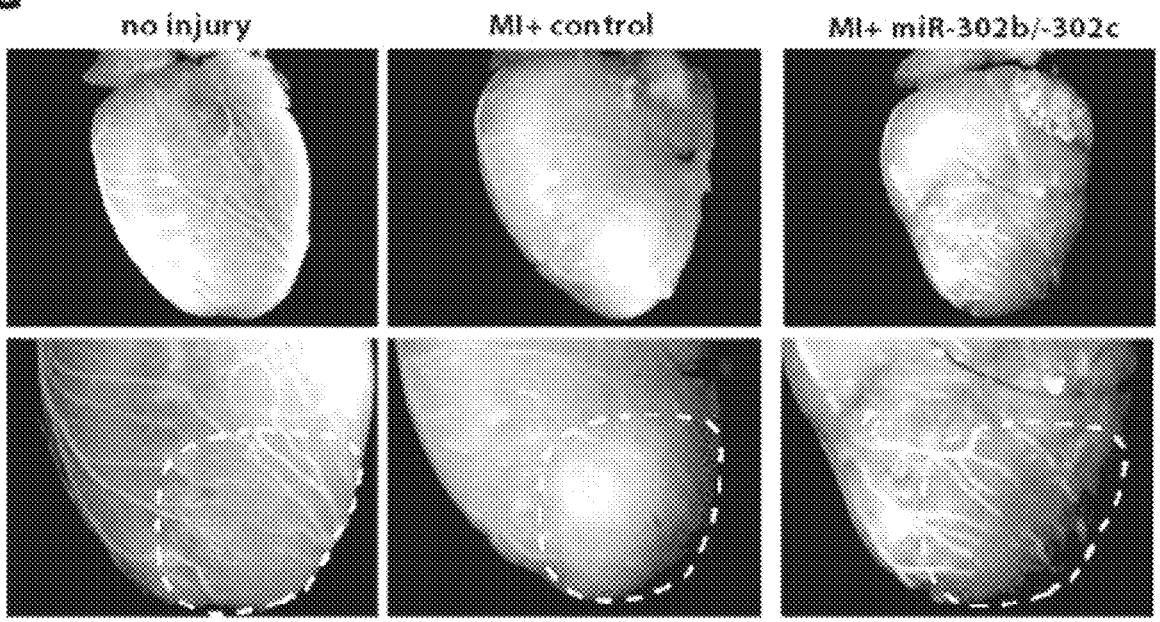
Figure 13:
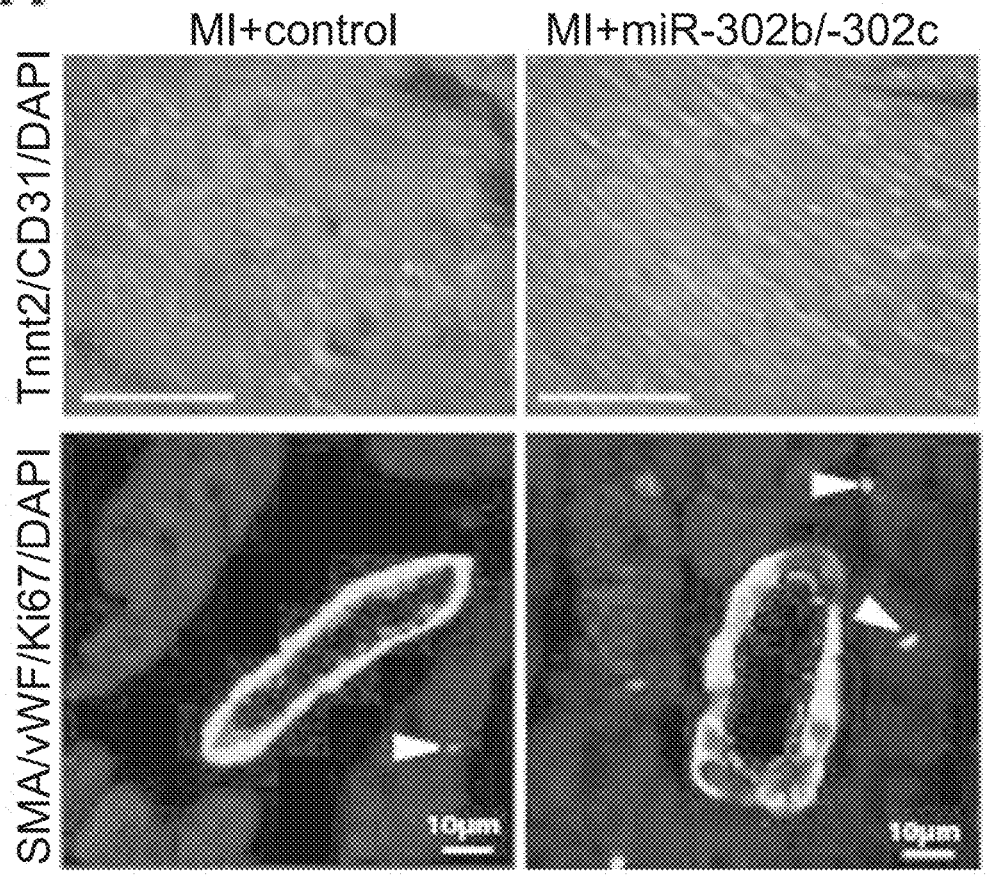

FIG. 13. Half-life of miR302-367 mimic treatment and the effects on cardiomyocyte proliferation, apoptosis, and vascular perfusion (A) miR302b/c/367 expression in the adult heart at various time points post-miRNA mimic treatment. Numbers on bars indicate the relative expression level of miRNA by qRT-PCR. (B) Schematic of mimic treatment experiment and expression of Mst1. Lats2, and Mob1b in the heart on the final day of miR mimic treatment. Daily mimic treatment was chosen due to the relative short half-life of miRNA mimics in vivo (see A). (C) Schematic of mimic treatment experiment and qRT-PCR showing relative expression of genes associated with cell proliferation and fetal gene program. (D) Schematic of myocardial infarction (MI) and mimic treatment experiment and qRT-PCR of Hippo signaling components at day 7 post-MI. (E) Immunostaining images and quantification for PH$_3$, Tnnt2, and TUNEL at day 7 post-MI. (F) qRT-PCR analysis showing the transient activation of genes related with cell proliferation, survival, and fetal gene program in miR mimic treated-hearts post-MI. (G) The vascular plexus was highlighted by Microfil at 9 days post-MI and after 7 days of miR302b/c mimic treatment. (Bottom row) images at higher magnification. (H) Immunostaining for CD31 and Tnnt2, markers of vasculature, in control-miR302 mimic-treated hearts. Scale bars, 100 μm. (I) Immunostaining for SMA, vWF, and Ki67 showing no increase in the proliferation of smooth muscle cells and endothelial cells in miR302 mimic treated hearts 7 days post-ML Data in (A to F) are means±s.e.m. (n=6). *p<0.05, versus control mimic, by Student's t test.

Figure 14:
Figure 14:
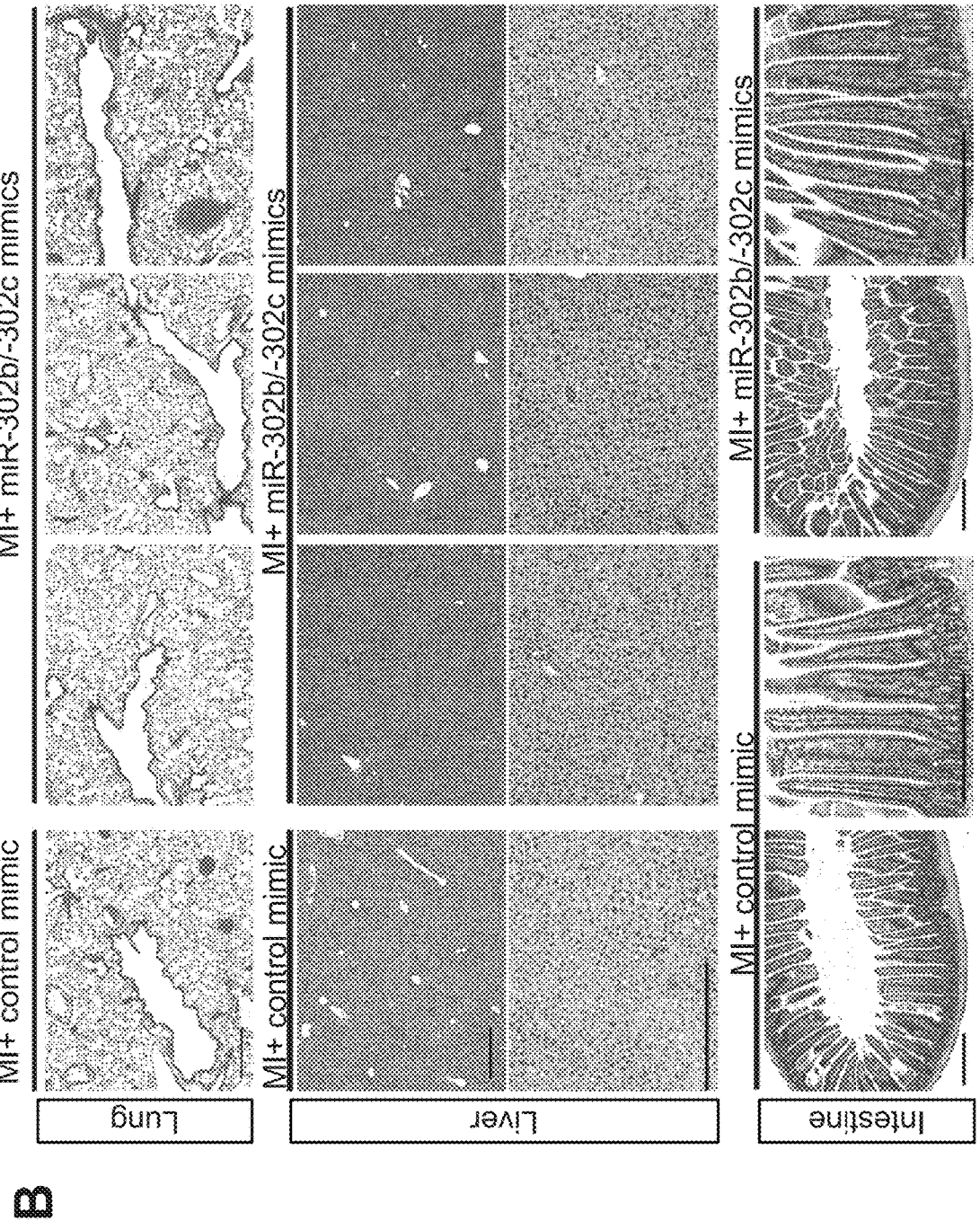

FIG. 14. Expression of miR302 mimics in the lung and organ histology after systemic treatment with mimics. (A) qRT-PCR. showing miR302b/c/367 levels in the lung at various time points after miRNA-mimics treatment. Numbers on bars indicate the relative expression level of miRNA. (B) Histology analysis showing the normal morphology in the lung, liver, and intestine in the mice at 6 weeks after miR mimic treatment. Scale bars, 100 μm. Images are representative of n=6 animals.

DETAILED DESCRIPTION OF THE INVENTION

The invention relates to compostions and methods for promoting cellular proliferation and de-differentiation of cells into stem cells to foster tissue regeneration. Specifically, the invention relates to transiently administering a microRNA (miR) or its mimic for promoting cardiomyocyte proliferation and cardiac regeneration.

Inventors of this application have surprisingly and unexpectedly found that miR302-367 is expressed in early cardiac development and is important for cardiomyocyte proliferation during embryonic development. Increased miR302-367 expression leads to high level and persistent cardiomyocyte proliferation and ultimately cardiomegaly. miR302-367 functions, in part, by targeting several components of the Hippo signal transduction pathway including Mst1, Lats2, and Mob1b.

Inventors of this application have also surprisingly and unexpectedly found that persistent re-expression of miR302-367 in the postnatal heart reactivates the cardiomyocyte cell cycle and increases cardiomyocyte regeneration but leads to de-differentiation of cardiomyocytes and heart failure. However, temporary application of miR302-367 or its mimics promotes cardiac regeneration without the unwanted affects on cardiac function. These studies show therapeutic approach of using miR or its mimics to promote cardiac regeneration and also indicate that such approaches should be transient to avoid cardiomyocyte de-differentiation and dysfunction.

The terms, "transient" or "temporary application," as used herein, may refer to application or administration of an miR molecule or its mimic sufficient to transiently activate cardiomyocyte proliferation, but not to reactivate the cell cycle of postnatal cardiomyocytes. For example, transient or temporary application may comprise one time single administration of the composition.

A composition of the invention may include a microRNA (miR) 302-367 cluster, a miR 302-367 cluster mimic, or a combination thereof.

The term "miR cluster," as used herein refers to a genetic region or locus that contains a plurality of microRNAs. The miR cluster may include a group of adjacent or related genes, which in one embodiment, are co-transcribed in a polycistronic manner. The miR genes in a cluster can be transcribed under the control of a single promoter or a plurality of promoters. In one embodiment, a miR 302-367 cluster includes a single sequence having multiple miRs, all corresponding to the 302-367 locus.

In some embodiments, a microRNA (miR) 302-367 cluster comprises a plurality of miRNAs, including, but not limited to, miR-302a, miR-302a*, miR-302b, miR-302b*, miR-302c, miR-302c*, miR-302d, miR-367 and miR-367*.

The nucleic acid sequences of miR-302b, miR-302b*, miR-302c, miR-302c*, miR-302a, miR-302a*, miR-302d, miR-367, and miR-367* are known in the art and described in US2013/0035374 and WO2011/133288, which are incorporated by reference herein in their entirety. For example, the nucleic acid sequence of miR-302b is: UAAGUGCUUCCAUGUUUUAGUAG (SEQ ID NO: 1) (miRBase Accession No: MI0000772; ENTREZGENE: 442894); the nucleic acid sequence of miR-302b* is: ACUUUAACAUGGAAGUGCUUUCU (SEQ ID NO: 2) (miRBase Accession No: MIMAT0000714); the nucleic acid sequence of miR-302c is: UAAGUGCUUCCAUGUUUCAGUGG (SEQ ID NO: 3) (miRBase Accession No: MI0000773; ENTREZGENE: 442895); the nucleic acid sequence of miR-302c* is: UUUAACAUGGGGGUACCUGCUG (SEQ ID NO: 4) (miRBase Accession No: MIMAT0000716); the nucleic acid sequence of miR-302a is: UAAGUGGUUCCAUGUUUUGGUGA (SEQ ID NO: 5) (miRBase Accession No: MI0000738; ENTREZGENE: 407028); the nucleic acid sequence of miR-302a* is: UAAACGUGGAUGUACUUGCUUU (SEQ ID NO: 6) (miRBase Accession No: MIMAT0000683); the nucleic acid sequence of miR-302d is: UAAGUGCUUCCAUGUUUGAGUGU (SEQ ID NO: 7) (miRBase Accession No: MI0000774; ENTREZGENE: 442896); the nucleic acid sequence of miR-367 is: AAUUGCACUUUAGCAAUGGUGA (SEQ ID NO: 8) (miRBase Accession No: MIMAT0004686; ENTREZGENE: 442912); and the nucleic acid sequence of miR-367* is: ACUGUUGCUAAUAUGCAACUCU (SEQ ID NO: 9) (miRBase Accession No: MI0000772).

The nucleic acid sequences described herein may include homologous, variant, and functional fragment sequences. Such sequences are known in the art and described in US2013/0035374, WO2011/133288 and WO2009/091659, which are incorporated by reference herein in their entirety.

Nucleic acids described herein may be replaced by functionally equivalent fragments or homologs, which in one embodiment, have at least 50%, 60%, 70%, 80%, 90%, 95%, or 98% sequence homology. In particular, for example, mir-302a, mir-302b, mir-302c, and mir-302d genes and RNAs described herein may be replaced with other genes and RNAs with similar functions such as, for example, mir-302a* mir-302b*, mir-302c*, mir-367, mir-93, mir-371, mir-372, mir-373, mir-520, and the like.

In one embodiment, the miR302-367 cluster for use in the compositions and methods of the present invention is the entire miR302-367 locus. In another embodiment, the miR302-367 cluster for use in the compositions and methods of the present invention is the miR302-367 gene cluster intron. In another embodiment, the miR302-367 cluster for use in the compositions and methods of the present invention is the first 1234 nucleotides of the miR302-367 gene cluster. In another embodiment, the miR302-367 cluster for use in the compositions and methods of the present invention is a recombinant gene comprising one or more of miR302b, miR302c, miR302a, miR302d and miR367 linked so as to be transcribed as a single unit. In another embodiment, the miR302-367 cluster for use in the compositions and methods of the present invention is a recombinant gene comprising one or more of miR302b, miR302c, and miR367 linked so as to be transcribed as a single unit. In one embodiment, only the genes encoding the miRs are included in the miR 302-367 cluster, while in another embodiment, intronic sequences between and adjacent to the genes encoding the miRs are included in the miR 302-367 cluster. In another embodiment, the miR302-367 cluster is a 644 bp fragment of the human miR302-367 region or a 690 bp fragment of the mouse miR302-367 region. In another embodiment, the miR302-367 cluster is the intronic region between exons 8 and 9 of the Larp7 gene as denoted on the Ensembl database.

In one embodiment, the mir-302 members share an identical (100%) sequence in their 5' first seventeen (17) nucleotides, including the entire seed motif, and an overall 83%-96% homology in their 23-nucleotide mature miRNA sequences. The seed motif is located in the first 5' eight nucleotides of a mature miRNA sequence, which determines the binding specificity and efficiency between the miRNA and its target genes. Based on the prediction of "TARGETSCAN" (http://www.targetscan.org/) and "PICTAR-VERT" (http://pictar.bio.nyu.edu/cgi-bin/PicTar_vertebrate.cgi?) programs linked to the Sanger miRBase:: Sequences website (http://microrna.sanger.ac.uk/), they are directed against almost the same cellular genes, including over 445 conserved genes in human and mouse. Most of these target genes are developmental signals and transcriptional factors involved in initiation and/or facilitation of lineage-specific cell differentiation during early embryogenesis (Lin et al., (2008) *RNA* 14:2115-2124). Many of these target genes are also well-known oncogenes. For example, the mir-302/367 cluster targets, inter alia, eighteen members of the IGF receptor (IGFR)-Ras/PI3K signaling pathways where insulin-like growth factors (IGF) are potent developmental signals for the differentiation of neuron-specific cell lineage via either the Ras/Raf/mitogen-activated protein kinase (MAPK) or the phosphatidylinositol 3-kinase (PI3K)/Akt signal transduction pathway, which is the same signaling pathways involved in many tumor/cancer transformations, such as brain tumor, breast cancer, lung cancer, prostate cancer, and skin melanoma. Thus, in one embodiment, the compositions and methods of the present invention may be used to suppress tumors or tumor formation.

The methods described here may also be used with miRNA families other than miR-302-367. In one embodiment, the miRNA family is miR290/295 cluster on chromosome 7 in mouse. In another embodiment, the miRNA family is hsa-miR-372 (MI0000780), hsa-miR-373 (MI0000781), or hsa-miR-373/373*; hsa-miR-371-373 cluster; hsa-miR-520c (MI0003158), or hsa-miR-520c-5p/520c-3p; mmu-miR-290 (MI0000388), mmu-miR-291a (MI0000389), or mmu-miR-291a-5p/291a-3p; mmu-miR-294 (MI0000392), or mmu-miR-294/294*; and mmu-miR-295 (MI0000393), or mmu-miR-295/295* or others described in Suh et al. (2004) *Dev. Biol.* 270:488-498, incorporated herein by reference in its entirety, or otherwise known in the art. In one embodiment, a combination of the above-referenced miRs may be used in the compositions and methods described here. This list is not to be construed as limiting, and other miRNA families highly and specifically expressed in embryonic stem cells may be used in the methods described here.

In one embodiment, the following miRNAs may be used in the compositions and methods described here, either instead of or in addition to miR-302-367: miR106, miR20a/b, miR93, miR17-92 cluster, or a combination thereof.

In another aspect, a microRNA mimic is used in the compositions and methods described here. The miRNA mimic may include a double-stranded oligonucleotide designed to mimic the function of endogenous mature miRNA. In some embodiments, the miRNA mimic may include one or more chemical modifications that enhances the stability and/or functionality of the duplex. In one embodiment, the modification may include 2'-O-methyl modification of some or all of the nucleotides of the sense strand and/or minimizes the nuclease sensitivity of the strand and/or enhance the entry of the antisense strand into the RNA interference silencing complex (RISC). The mimic can be chemically enhanced to preferentially program RNA-Induced Silencing Complex (RISC) with the active miRNA strand.

The miRNA mimic may also comprise one or more chemical modifications as described in US2007/0269889, incorporated herein by reference in its entirety. Commercially available mimics, for example, from Dharmacon or Qiagen, can also be used.

In one example, the mimic is a cholesterol-modified mimic. In one embodiment, the mimic enables non-viral mediated miRNA expression. In one embodiment, the mimic is a small and active version of a microRNA. In another embodiment, the mimic is a non-natural double-stranded miRNA-like RNA fragment, which in one embodiment is designed to have its 5' end bearing a partially complementary motif to the selected sequence in the 3' UTR unique to the target gene. In one embodiment, this RNA fragment can specifically bind its target gene in a gene-specific fashion. In one embodiment, the mimic is a multi-miRNA mimic, which is able to silence multiple genes. In one embodiment, the mimic is a multi-miRNA mimic, as described in Wang, 2009 (Multi-miRNA Hairpins and Multi-miRNA Mimics Technologies in MicroRNA Interference Technologies, Springer Berlin Heidelberg).

One or more pre-miRNA precursors can be used in the compositions and methods described here. The pre-mRNA precursor may act to gain function for the miRNA. Any suitable form of a pre-mRNA precursor can be used.

In some embodiments, when a mimic or pre-miRNA precursor is used, one or more mimics or pre-miRNA precursors can be used instead of all in the cluster.

In one embodiment, the miRNA of the compositions and methods described here may be mature miRNA. Alternatively, the miRNA may be an miRNA precursor. In one embodiment, an miRNA precursor is a pre-miRNA, which is subject to cleavage by an RNAse III type double stranded endonuclease called Dicer, resulting in an imperfect miRNA:miRNA* duplex that is around 20-25 nucleotides in size. This duplex contains the mature miRNA strand and its opposite complementary miRNA* strand.

In another aspect, the present invention provides a composition comprising a) an isolated nucleic acid comprising a microRNA (miR) 302-367 cluster or its mimic and b) a histone deacetylase (HDAC) inhibitor. Preferably, the HDAC inhibitor is valproic acid. Other suitable HDAC inhibitors are known in the art and can be used. An HDAC inhibitor interferes with the function of histone deacetylase to remove acetyl groups from lysine residues leading to the formation of condensed and transcriptionally silenced chromatin.

In another aspect, also provided herein are expression vectors. An expression vector having an miRNA can be delivered to cells of a subject. The nucleic acid molecules are delivered to the cells of a subject in a form in which they can be taken up and are advantageously expressed so that therapeutically effective levels can be achieved.

Methods for delivery of polynucleotides to a cell include using a delivery system, such as liposomes, polymers, microspheres, gene therapy vectors, and naked DNA vectors.

Transducing viral (e.g., retroviral, adenoviral, lentiviral and adeno-associated viral) vectors can be used for somatic cell gene therapy, especially because of their high efficiency of infection and stable integration and expression (see, e.g., Cayouette et al., *Human Gene Therapy* 8:423-430, 1997; Kido et al., *Current Eye Research* 15:833-844, 1996; Bloomer et al., *Journal of Virology* 71:6641-6649, 1997; Naldini et al., *Science* 272:263-267, 1996; and Miyoshi et al., *Proc. Natl. Acad. Sci. U.S.A.* 94:10319, 1997). For example, a polynucleotide encoding an miRNA molecule is cloned into a retroviral vector and expression is driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, *Human Gene Therapy* 15-14, 1990; Friedman, *Science* 244:1275-1281, 1989; Eglitis et al., *BioTechniques* 6:608-614, 1988; Tolstoshev et al., *Current Opinion in Biotechnology* 1:55-61, 1990; Sharp, *Lancet* 337:1277-1278, 1991; Cornetta et al., *Nucleic Acid Research and Molecular Biology* 36:311-322, 1987; Anderson, *Science* 226:401-409, 1984; Moen, *Blood Cells* 17:407-416, 1991; Miller et al., *Biotechnology* 7:980-990, 1989; Le Gal La Salle et al., *Science* 259:988-990, 1993; and Johnson, *Chest* 107:77S-83S, 1995). Retroviral vectors are particularly well developed and have been used in clinical settings (Rosenberg et al., *N. Engl. J. Med* 323:370, 1990; Anderson et al., U.S. Pat. No. 5,399,346). Non-viral approaches can also be employed for the introduction of an miRNA therapeutic to a cell of a subject. For example, an miRNA can be introduced into a cell by administering the nucleic acid in the presence of lipofection (Feigner et al., *Proc. Natl. Acad. Sci. U.S.A.* 84:7413, 1987; Ono et al., *Neuroscience Letters* 17:259, 1990; Brigham et al., *Am. J. Med. Sci.* 298:278, 1989; Staubinger et al., *Methods in Enzymology* 101:512, 1983), asialoorosomucoid-polylysine conjugation (Wu et al., *Journal of Biological Chemistry* 263:14621, 1988; Wu et al., *Journal of Biological Chemistry* 264:16985, 1989), or by micro-injection under surgical conditions (Wolff et al., *Science* 247:1465, 1990). Preferably the microRNA molecules are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Micro RNA expression for use in polynucleotide therapy methods can be directed from any suitable promoter (e.g., the human cytomegalovirus (CMV), simian virus 40 (SV40), or metallothionein promoters), and regulated by an appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers. For a particular subject, the specific dosage regimes should be adjusted over time according to the individual need and the professional judgment of the person administering or supervising the administration of the compositions.

In another embodiment, therapeutic compositions are provided that increase the expression of a microRNAs described herein for treatment. In another embodiment, the pharmaceutical compositions are provided comprising an agent that enhances the expression of an miRNA described here. Polynucleotides described here may be administered as part of a pharmaceutical composition. The composition is preferably sterile and contains a therapeutically effective amount of a polynucleotide molecule in a unit of weight or volume suitable for administration to a subject.

The therapeutic polynucleotide molecule described here may be administered with a pharmaceutically-acceptable carrier, in unit dosage form. Conventional pharmaceutical practice may be employed to provide suitable formulations or compositions to administer the compounds to patients.

Carrier as used herein includes pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt forming counterions such as sodium; and/or nonionic surfactants such as TWEEN, polyethylene glycol (PEG), and PLURONICS.

The active ingredients may also be entrapped in microcapsules prepared, for example, by interfacial polymerization, for example, hydroxymethylcellulose or gelatin-microcapsules and poly(methylmethacylate) microcapsules, respectively, in colloidal drug delivery systems (for example, liposomes, albumin microspheres, microemulsions, nano-particles, and nanocapsules) or in macroemulsions. The formulations to be used for in vivo administration must be sterile. This is readily accomplished by filtration through sterile filtration membranes. Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The compositions described here may be administered in combination with one or more other prophylactic or therapeutic agents, including, for example, but not limited to cytotoxic agents, chemotherapeutic agents, cytokines, growth inhibitory agents, anti-hormonal agents, kinase inhibitors, anti-angiogenic agents, cardioprotectants, immunostimulatory agents, immunosuppressive agents, agents that promote proliferation of hematological cells, angiogenesis inhibitors, protein tyrosine kinase (PTK) inhibitors, additional antibodies, or other therapeutic agents. In one embodiment, the compositions of the invention are administered in conjunction with radiotherapy, chemotherapy, photodynamic therapy, surgery or other immunotherapy, to a patient who has a hyperproliferative disorder, such as cancer or a tumor.

Administration may begin before the patient is symptomatic. Any appropriate route of administration may be employed, for example, administration may be parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

In some embodiments, compositions described here are administered systemically. Preferably, the systemic administration includes parenteral administration, e.g., intravenous, intradermal, subcutaneous, oral (e.g., inhalation), transdermal (topical), transmucosal, and rectal administration. In one embodiment, it is advantageous to formulate oral or parenteral compositions in dosage unit form for ease of administration and uniformity of dosage. "Dosage unit form" refers to physically discrete units suited as unitary dosages for the subject to be treated, each unit containing a predetermined quantity of an active compound calculated to produce the desired therapeutic effect in association with the required pharmaceutical carrier.

Methods well known in the art for making formulations can be found, for example, in "Remington: The Science and Practice of Pharmacy" Ed. A. R. Gennaro, Lippincourt Williams & Wilkins, Philadelphia, Pa., 2000. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for inhibitory nucleic acid molecules include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The dosage to treat a subject may depend on the choice of the route of administration, the nature of the formulation, the nature of the subject's illness, the subject's size, weight, surface area, age, and sex, other drugs being administered, and the judgment of the attending physician.

In another aspect, kits are provided comprising: an isolated nucleic acid comprising a microRNA (miR) 302-367 cluster or a miR 302-367 cluster mimic and instructions. In some embodiments, the kits may include a histone deacetylase (HDAC) inhibitor.

The term "about," as used herein, may refer to quantitative terms plus or minus 5%, or plus or minus 10%, or plus or minus 15%, or plus or minus 20%.

The term "subject," as used herein refers to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects. A subject to be treated may be identified in the judgment of the subject or a health care professional, which can be subjective or objective.

The term "treatment," as used herein, may refer to administration of a substance to a subject with the purpose to cure, alleviate, relieve, remedy, prevent, suppress, inhibit, or ameliorate a disorder, symptoms of the disorder, a disease state secondary to the disorder, or predisposition toward the disorder. "Treating" may refer to therapeutic treatment or prophylactic or preventative measures, wherein the object is to prevent or lessen the targeted pathologic condition or disorder as described hereinabove, or "treating" may refer only to therapeutic treatment. Thus, "treating" may include directly affecting or curing, suppressing, inhibiting, preventing, reducing the severity of, delaying the onset of, reducing symptoms associated with the disease, disorder or condition, or a combination thereof. Additionally, "treating" refers inter alia to delaying progression, expediting remission, inducing remission, augmenting remission, speeding recovery, increasing efficacy of or decreasing resistance to alternative therapeutics, or a combination thereof. Furthermore, "preventing" refers, inter alia, to delaying the onset of symptoms, preventing relapse to a disease, decreasing the number or frequency of relapse episodes, increasing latency between symptomatic episodes, or a combination thereof. In addition, "suppressing", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, prolonging patient survival, or a combination thereof.

The terms "effective amount," as used herein, refers to an amount of a compound that is capable of producing a medically desirable result in a treated subject. The medically desirable result may be objective (i.e., measurable by some test or marker) or subjective (i.e., subject gives an indication of or feels an effect).

All references mentioned herein are to be construed as being incorporated by reference in their entirety.

The following examples are presented in order to more fully illustrate the preferred embodiments of the invention. They should in no way be construed, however, as limiting the broad scope of the invention. Methods for performing the experiments are well known to those skilled in the art.

EXAMPLES

Example 1

A microRNA-Hippo Pathway that Promotes Cardiomyocyte Proliferation and Cardiac Regeneration in Mice In contrast to lower vertebrates, the mammalian heart has limited capacity to regenerate after injury in part due to ineffective reactivation of cardiomyocyte proliferation. While evidence exists for a low level of cardiomyocyte proliferation in the adult heart, it remains unclear whether increasing this rate could be used to therapeutically promote cardiac regeneration. In this Example, the microRNA cluster miR302-367 is shown to be important for cardiomyocyte proliferation during development and is sufficient to induce cardiomyocyte proliferation in the adult and promote cardiac regeneration. Loss of miR302-367 leads to decreased cardiomyocyte proliferation during development. In contrast, increased miR302-367 expression leads to a profound increase in cardiomyocyte proliferation, in part through repression of the Hippo signal transduction pathway. Postnatal expression of miR302-367 leads to reactivation of the cell cycle in cardiomyocytes resulting in reduced scar formation after infarction. However, long-term expression of miR302-367 leads to cardiomyocyte de-differentiation and dysfunction, suggesting that persistent reactivation of the cell cycle in postnatal cardiomyocytes is not desirable. Importantly, this limitation can be overcome by transient systemic application of miR302-367 mimics, leading to increased cardiomyocyte proliferation and mass, decreased fibrosis, and improved function after injury. Our data demonstrate the ability of microRNA based therapeutic approaches to promote cardiac repair and regeneration through the transient activation of cardiomyocyte proliferation.

Materials and Methods

Mouse Alleles

The miR302-367flox/flox allele was generated by flanking all five of the miRNAs in this cluster with loxP sites using standard homologous recombination in ES cells. The R26R-miR302-367Tg/+ allele was generated using previously described vectors to insert a DNA sequence containing all five members of the miR302-367 cluster into the CAG-R26R locus using standard homologous recombination in ES cells. Genotyping primers for these two new alleles are listed in Table 5. Generation and genotyping of the Nkx2.5cre and Myh6mercremer lines has been described previously. Mice were kept on a mixed C57BL/6:129SVJ background. All animal procedures were performed in accordance with the Institutional Animal Care and Use Committee at the University of Pennsylvania.

Histology

Tissues were fixed in 4% paraformaldehyde, embedded in paraffin, and sectioned at 6-μm intervals. Immunohistochemical staining and other histological procedures were performed using previously described protocols. Primary antibodies were: MF20 (1:20; Hybridoma Bank-University of Iowa), Ki67 (1:50; Abcam, ab16667), α-actinin (1:100; Sigma, A7811), Phospho-Histone H3 (PH3, 1:200; Cell Signaling Technology; 9706L), phospho-Yap (1:200; Cell Signaling Technology, 4911), Yap (1:100; Cell Signaling Technology, 4912S), cardiac Troponin T (cTnT, 1:100; Thermo Scientific, MS-295-P1), Troponin T-C (Tnnt2, 1:100; Santa Cruz Biotechnology, sc-8121), AuB (1:100; Abcam, ab2254), BrdU (1:50; Hybridoma Bank at University of Iowa). Cell size was quantified using ImageJ software from three independent hearts per group, and 6 histological sections per heart. Whole-mount in situ hybridization was performed using a pri-miR302-367 probe and protocols obtained from Exiqon. Cytoplasmic and nuclear ratio for total Yap protein was quantified using immunofluorescence imaging and Fiji imaging software.

Neonatal Cardiomyocyte Isolation and Culture

Neonatal mouse cardiomyocytes were prepared by the Cardiac Myocyte Core Laboratory at the University of Pennsylvania. Briefly, mouse cardiomyocytes were isolated by enzymatic disassociation of 1-day-old neonate hearts (P1). Cells were plated differentially for 2 hours to remove fibroblasts. Cardiomyocytes were plated on laminin-coated glass coverslips (10 mg/cm$^2$) in 12-well plates at 2.5×10$^5$ cells per well. On the following day, culture medium was replaced with fresh medium, and the cells were transduced with miR-302-367 lentivirus and Yap shRNA lentivirus (pLKO.1-Yap shRNA) (Thermo Scientific Open Biosystems, RMM4534), using polybrene (5 mg/mL; American Bioanalytical). After 48 hours, cardiomyocytes were fixed and processed for immunostaining with the indicated antibodies.

Lentivirus Expression in Cardiomyocytes

Human embryonic kidney (HEK) 293T cells (American Type Culture Collection) were cultured on 100-mm plates at 70% confluence. Lentiviral vectors were packaged in 293T cells using X-tremeGENE9 (Roche) to deliver 5 mg of the lentiviral plasmid, 2.5 mg of psPAX2, and 2.5 mg of pMD2.G (Addgene plasmid 12259). Viral supernatant was collected at 48 hours after transfection, concentrated, and applied to cardiomyocytes.

Gene Expression and Microarray Analysis

Quantitative PCR analysis was performed using Trizol isolated RNA and used to generate cDNA using random hexamer primers and SuperScript II RT (Invitrogen). qRT-PCR primer sequences are listed in Table 5. TaqMan MicroRNA Assays were used for detection of miRNA expression. For microarray analysis, total RNA was extracted from three Nkx2.5cre and three Nkx2.5cre:R26R-miR302-367Tg/+ hearts at P14, converted to cDNA and used on Affymetrix Mouse Gene 2.0 ST Arrays. Data was analyzed using Affymetrix Microarray Suite 5.0, Significance Analysis of Microarray (SAM), and the Empirical Bayes Analyses of Microarrays (EBAM). Genes with 1.5-fold or greater changes over that of the experimental mean with p<0.01 (ANOVA) were considered significant. Complete microarray dataset has been deposited in the GEO database (Accession # GSE54988).

Adult Cardiomyocyte Isolation and FACS Analysis

Adult hearts (8 to 10 weeks old) were dissected. Ventricular myocytes were isolated using a modified method of a previously described protocol. Briefly, excised hearts were mounted on a Langendorf apparatus and perfused with Ca$^{2+}$-free Tyrode's solution for 6 min at 3.0 to 3.5 mL/min at a temperature of 37° C., followed by 12 to 15 min of perfusion with Ca$^{2+}$-free Tyrode's solution containing collagenase B (0.35 mg/mL), collagenase D (0.25 mg/mL; Roche Chemical Co.), and protease type XIV (0.05 mg/mL; Sigma Chemical Co.). The ventricles were teased into small pieces with forceps, and sections of ventricular tissue were gently triturated with a Pasteur pipette to dissociate individual myocytes. Noncardiomyocytes were depleted by centrifugation. Cardiomyocyte suspension was rinsed with phosphate-buffered saline (PBS) and then fixed in intracellular fixation buffer (eBioscience). For FACS analyses of cardiomyocyte purity, cells were first permeabilized in 1× permeabilization buffer (eBioscience) and then incubated with cardiac troponin T (1:100; Thermo Scientific, MS-295-P1) for 2 hours at room temperature, followed by incubation with secondary antibody (Alexa Fluor 647, Life Technologies) for 1 hour at room temperature. Samples were analyzed on a BD FACSCanto II (BD Biosciences).

Experimental Myocardial Infarction (MI) Model

Adult mice (12-15 weeks old, 30-35 gram, and mixed gender) of the indicated genotype and background were used. For the miR mimic study, adult mice (10-12 weeks old, 25-30 gram, male) of the C57BL/6J background were used. After an adequate depth of anesthesia was attained by intraperitoneal injection of Avertin (200-300 mg/kg, IP) and/or inhalation of isoflurane (1-3%), the regions of surgical areas (neck and chest) were shaved and antiseptic agents (betadine and 70% ethanol) were then applied. The mouse was fixed in a supine position with tape. The tongue was retracted and held with forceps, and a 20-G IV catheter was inserted orally into the trachea. The catheter was then attached to a Minivent (type 845, Harvard Apparatus) via the Y-shaped connector. Ventilation was performed with a tidal volume of 0.25-0.35 mL (10 mL/kg) and a respiratory rate of 80-110/min. Pure (100%) oxygen was provided to the inflow of the ventilator.

A thoracotomy was performed by separating the fourth or fifth intercostal space to expose the heart. The pericardium was opened and the heart was visualized by gentle retraction on the rib cage. An 8-0 silk ligature, entering the heart on the left margin of the pulmonary cone and exiting near the insertion of the left auricular appendage was gently tied onto the LAD coronary artery to induce permanent MI. The chest and skin incision were closed by layer with 4-0 or 5-0 sutures. The mouse was removed from the ventilator at 10-30 minutes post-MI and placed in external warm cages for about 15-45 minutes until full recovery. The sham procedure was performed in an identical manner, with the exception that the occluding ligature was not tied.

Systemic Delivery of miRNA Mimics Using a Neutral Lipid Emulsion

Synthetic miR302b/c mimics and miRNA mimic control (Dharmacon) were formulated with Neutral Lipid Emulsion (NLE, MaxSuppressor in vivo RNALancerII, BIOO Scientific) according to the manufacturer's instructions. Adult mice (10 weeks) were given a single dose of 10-mg NLE-formulated miRNA mimics by intravenous tail-vein injection. A single dose per day was chosen on the basis of studies showing that the half-life of the mimics in cardiac tissue was between 8 and 24 hours (FIG. 13A). Hearts were perfused with PBS to remove circulating blood and snap-frozen in liquid nitrogen at the indicated time points after miRNA mimic treatment. For qRT-PCR of mimic concentration in tissue, RNA was isolated from the heart tissues following the mirVana miRNA Isolation Kit procedure (Ambion). To determine the effect of miRNA mimics on cardiovascular outcome after MI, miR-302b/c mimics or miRNA mimic control (10 mg per mouse systemically) was administered daily for 7 days after MI.

Echocardiography

Mice were anesthetized with inhalation of isoflurane induction 3%, followed by maintenance at 2% using a nose cone. The mouse was placed on a warm platform in the supine position to keep the body temperature around 37° C. The chest hair was removed using hair removal gel cream (Nair). The limbs are taped onto the metal EKG leads. Echo was performed using VisualSonic Vevo 2100 system with a 40 MHz transducer for cardiac imaging. In brief, by placing the transducer along the long-axis of LV, and directing to the right side of the neck of the mouse, two-dimensional LV long-axis is obtained. Then the transducer is rotated clockwise by 90 degree, and the LV short-axis view is visualized. 2D-guided LV M-mode at the papillary muscle level is recorded from either the short-axis view and/or the long-axis view. Trans-mitral inflow Doppler spectra are recorded in an apical 4-chamber view by placing the sample volume at the tip of the mitral valves. Echo images are downloaded and analyzed offline using images analyzing software (Vevo 2100, 1.6, VisualSonic). At least three beats of imaging were measured and averaged for the interpretation of any given measurement. End-diastolic and end-systolic left ventricular internal diameters (LVIDd, LVIDs) were measured from the left ventricular short axis view with 2D orientated M-mode imaging. Left ventricular systolic function was estimated by fractional shortening (FS, %) according to the following formula: FS (%)=[(LVIDd−LVIDs)/LVIDd]×100. Ejection fraction (EF) was calculated using the end-systolic and end-diastolic volumes as described.

Retrograde Perfusion and Filling of Mouse Heart with Microfil for Visualization of Coronary Vasculature The visualization of mouse coronary artery was performed by adopting a technique for in vivo filling mouse coronary vessels. Briefly, mouse was euthanized with exsanguination under deep anesthesia, and heart was flushed out of blood with cold saline via inferior vena cava. The main branches of vessels except ascending aorta and pulmonary artery were ligated to prevent leakage. A 26-gauge angiocatheter was introduced into proximal aorta, and heart was perfused with cold saline (1-2 mL), 0.1M KCl solution (1 mL), then with fixative (2% PFA, 1 mL) for about 2 minutes. Yellow Microfil (Flow Tech, Inc.) was injected into aorta until good filling of coronary vessels (both arteries and veins) was evident with the visualization under microscope. After the filling was complete, the root of ascending aorta and pulmonary artery were quickly tied to keep Microfil inside of heart vessels for imaging. The heart was removed and fixed in 4% PFA overnight at 4° C. before imaging. The gross pictures of coronary vasculature were taken using digital camera under microscopy.

Western Blot Analysis

Proteins were isolated and solubilized after TRIzol extraction of RNA and DNA from cultured cells as previously described. Briefly, neonatal mouse cardiomyocytes were homogenized in TRIzol reagent, followed by the addition of chloroform. The RNA in the upper, aqueous phase was separated with the DNA and proteins in the lower, organic phase. The DNA was precipitated by the addition of ethanol. The protein in the phenol-ethanol supernatant was precipitated with acetone. The protein pellet was then washed with 0.3 M guanidine hydrochloride/95% ethanol and dissolved in 1% SDS at 50° C. Protein concentrations were determined using the BCA Protein Assay Reagent kit (Bio-Rad Laboratories). Proteins extracts were analyzed on polyacrylamide gels (10% NuPAGE bis-tris gel, Invitrogen) and transferred onto nitrocellulose membranes (Bio-Rad Laboratories). Rabbit anti-Yap (1:500; Cell Signaling Technology) and mouse anti-glyceraldehyde-3-phosphate dehydrogenase (1:1000; Sigma) were used as the primary antibodies. The blots were detected with SuperSignal West Pico Chemiluminescent Substrate (Thermo Scientific).

High-Throughput Sequencing of RNA Isolated by Cross-Linking Immunoprecipitation (HITS-CLIP)

HITS-CLIP was performed as published using the monoclonal Argonaute antibody 2A8.3×10E6 mouse embryonic stem cells were plated and, 48 hours later, cross-linked once with 400 mJ/cm² and an additional 200 mJ/cm² on ice. The Illumina library was sequenced on an Illumina GA-IIx at University of Pennsylvania Functional Genomics Core. Reads were aligned to the mouse genome (mm9), RefSeqs, and pre-miRNA (mirBase 13.0) using ELAND and allowing up to two mismatches. Significant CLIP tag cluster peaks located in the 3'UTR of mRNAs were identified, and potential miRNA regulators were identified as previously described.

Luciferase Reporter Assays

The firefly luciferase gene was derived from pGL3-basic vector (Promega) and cloned in to pcDNA3.1(−) vector. The DNA fragment containing full-length 3' UTR for putative miR-302-367 targets were inserted into pcDNA3.1(−) downstream of the luciferase cDNA. NIH-3T3 cells were transfected using Fugene 6 reagent according to the manufacturer's instructions with both the luciferase reporter and an expression plasmid for miR302-367 (pcDNA3.1-miR-302-367). Forty-eight hours after transfection, cell extracts were assayed for luciferase expression using a commercially available kit (Promega). Relative reporter activities are expressed as luminescence units normalized for β-galactosidase expression in the cell extracts.

Statistics

Data are reported as means±SEM of at least three independent assays unless otherwise noted. Unpaired Student's t test was used to for single comparisons, and one-way ANOVA for multiple comparisons. Statistical significance is displayed as *P<0.05 or **P<0.01 unless indicated otherwise.

Results miR302-367 Cluster is Required for Cardiomyocyte Proliferation During Development Expression of miR302-367 during early lung development in mice suggests that this miRNA cluster may be expressed in other tissues during development. To determine whether the miR302-367 cluster was expressed during cardiac development, quantitative real-time PCR (qRT-PCR) was performed on RNA isolated from mouse embryonic hearts at multiple developmental stages. All five members of the miR302-367 cluster were expressed at embryonic day (E) 9.5, but their expression decreased significantly after E11.5 (FIG. 1A). In situ hybridization indicated that the miR302-367 cluster is expressed in the myocardium of the embryonic mouse heart as early as E8.5 (FIG. 8A). At postnatal and adult stages, the expression of these miRNAs was not detectable by qRT-PCR (FIG. 1A).

Figure 1:
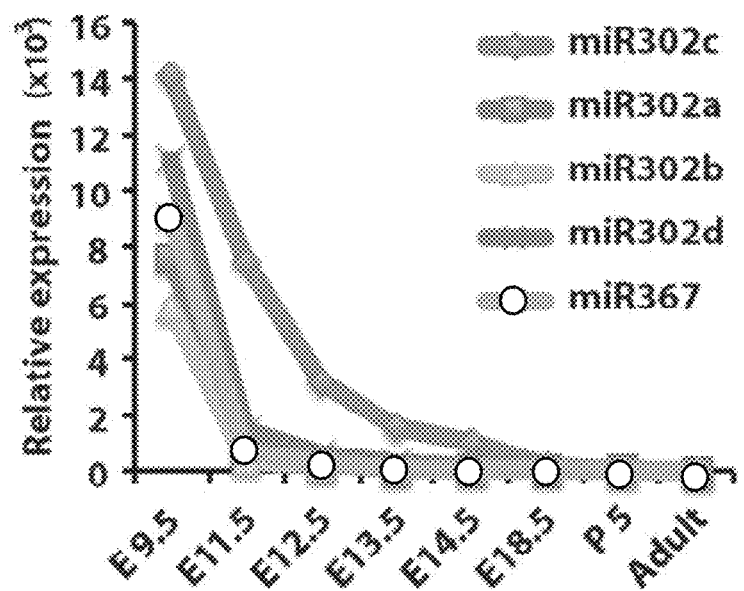
FIG. 1. miR302-367 is expressed in the early heart and is important for cardiomyocyte proliferation. (A) Relative expression of miR302-367 cluster members during heart development as determined by qRT-PCR. (B) Hematoxylin and eosin (H&E)-stained and immunostained sections of control E14.5 hearts showing thinning of ventricular wall, hypoplastic ventricular septum, and reduced cardiomyocyte proliferation in Nkx2.5$^{cre}$:miR302-367$^{flox/flox}$ mutants compared with miR302-367$^{flox/flox}$ mice. RV, right ventricle; LV, left ventricle; VS, ventricular septum; RA, right atrium. (C) Quantification of Ki67 (proliferation) from images in (B). (D) Gene expression changes associated with cardiomyocyte proliferation and differentiation in Nkx2.5$^{cre}$:miR302-367$^{flox/flox}$ null mutants versus controls at E14.5. (C and D) Data are means±SEM (n=3). P values determined by Student's t test.
Figure 1:
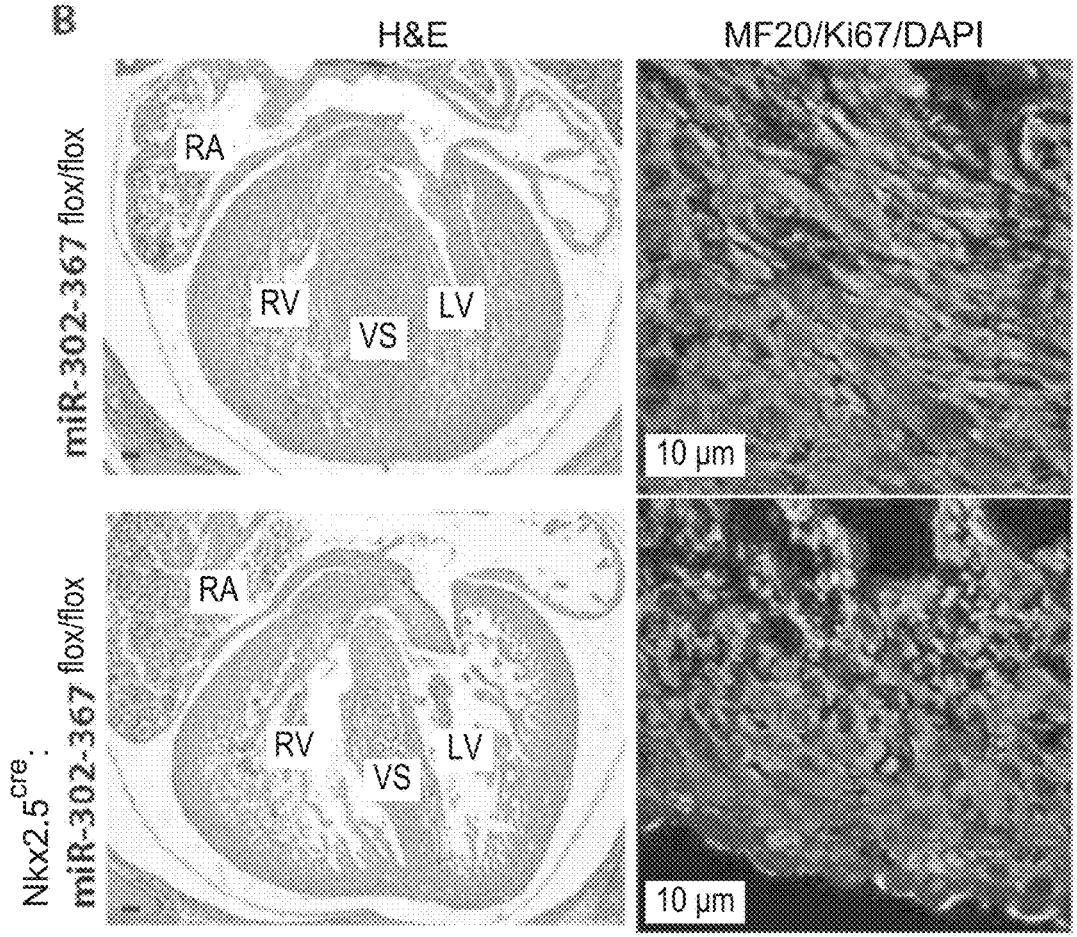
Figure 1:
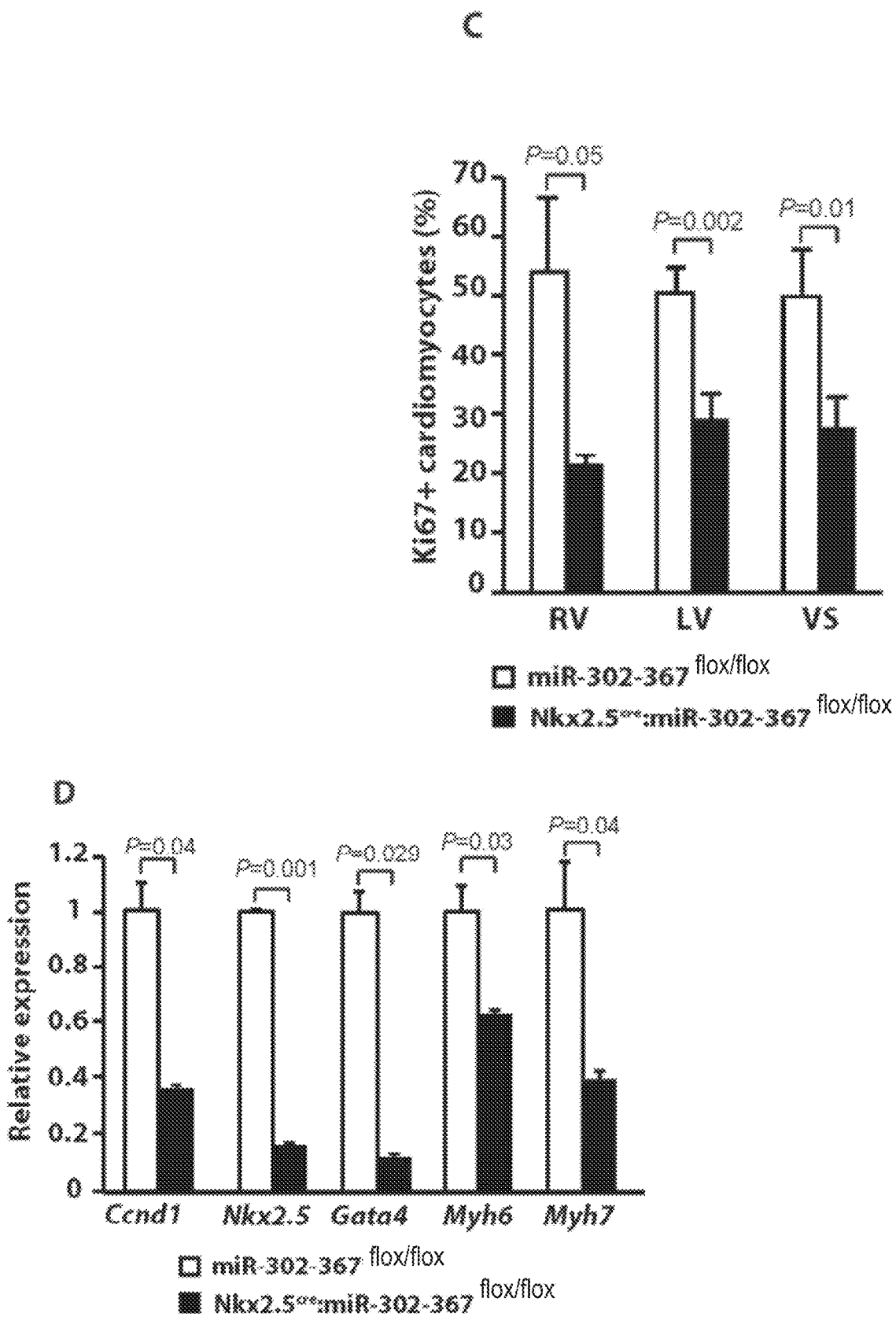

To investigate the role of the miR302-367 cluster in heart development, we generated a miR302-367$^{flox/flox}$ mouse line and used the Nkx2.5$^{cre}$ line to delete the entire cluster during cardiogenesis (FIG. 8, B and C). Decreased expression of members of the miR302-367 cluster was observed in Nkx2.5$^{cre}$:miR302-367$^{flox/flox}$ hearts by qRT-PCR (FIG. 8D). The miR302-367 cluster is located in intron 8 of the Larp7 gene. However, the expression of Larp7 was unaffected by genetic deletion of the miR302-367 locus. Nkx2.5$^{cre}$: miR302-367$^{flox/flox}$ hearts exhibited thinner ventricular walls and decreased proliferation compared with control littermates (FIGS. 1, B and C).

Decreased expression of the cell cycle proliferation gene Ccnd1 (cyclin D1) was consistent with decreased cell proliferation in Nkx2.5$^{cre}$:miR302-367$^{flox/flox}$ mutant hearts (FIG. 1D). Moreover, Nkx2.5$^{cre}$:miR302-367$^{flox/flox}$ mutant hearts showed decreased expression of Gata4, Nkx2.5, Myh6, and Myh7, indicating defects in cardiomyocyte differentiation at E14.5 (FIG. 1D). However, we did not observe a significant change in programmed cell death or loss in viability in Nkx2.5$^{cre}$:miR302-367$^{flox/flox}$ mutants (FIG. 8F), suggesting compensation by other miRNAs or pathways later in development.

Figure 2:
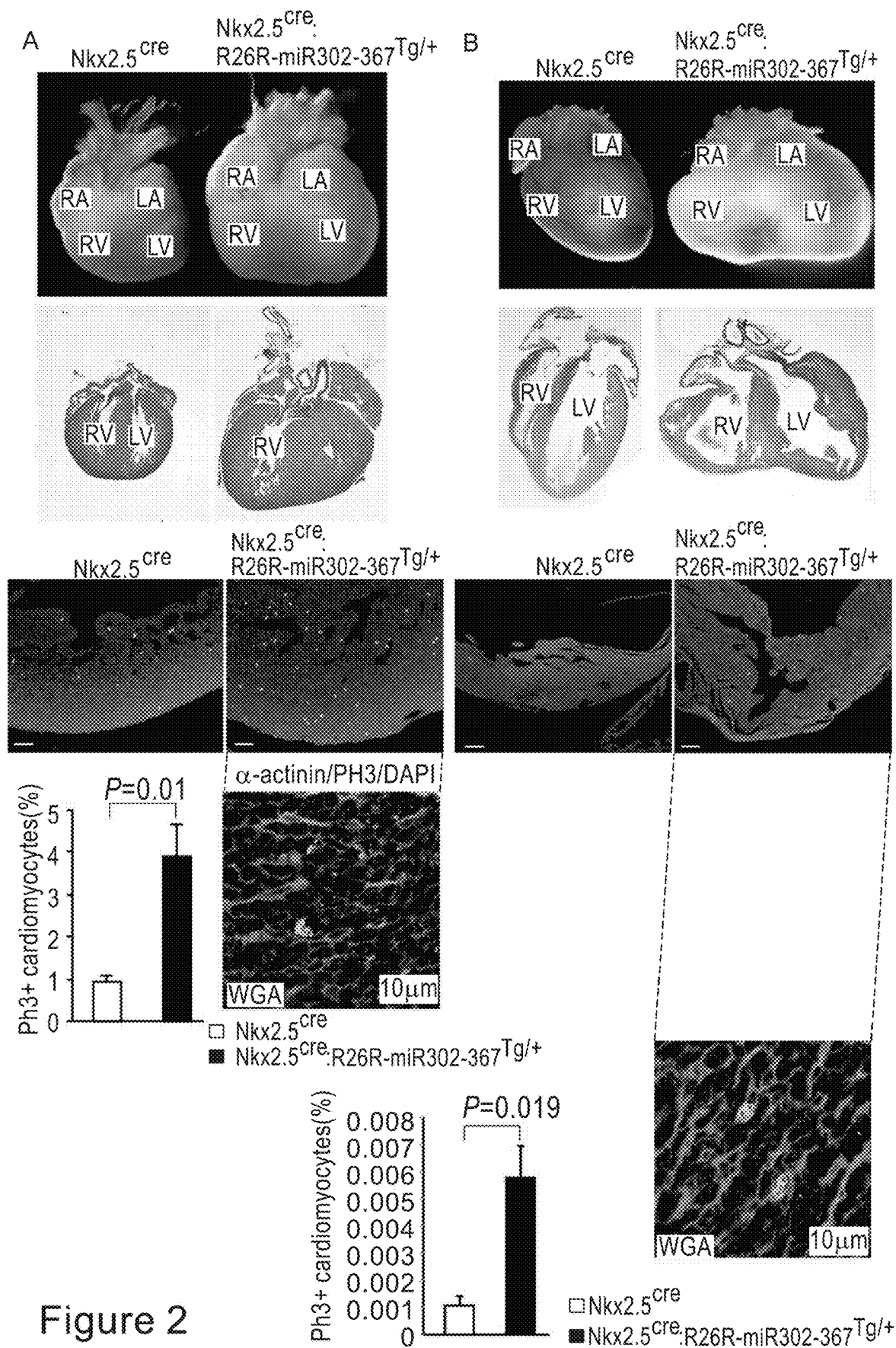
FIG. 2. Over-expression of miR302-367 cluster in developing heart results in increased cardiomyocyte proliferation and cardiomegaly. (A) Nkx2.5$^{cre}$: R26R-miR302-367$^{Tg/+}$ mutants have an enlarged heart with thickened ventricular myocardium and ventricular septal defects compared to Nkx2.5$^{cre}$ controls (B) Cardiomegaly and increased cardiomyocyte proliferation in Nkx2.5$^{cre}$:R26R-miR302-367$^{Tg/+}$ mutant hearts at P20. (A and B) Immunostainings for PH3 and α-actinin and wheat germ agglutinin (WGA) show the number of mitotic cardiomyocytes. Scale bars, 100 mm.

Over-Expression of miR302-367 Promotes Cardiomyocyte Proliferation in Embryonic and Postnatal Hearts A conditional mouse line was generated to perform miR302-367 gain-of-function experiments in vivo (R26R-miR302-367$^{Tg/+}$)(FIGS. 9, A and B). Activating this allele using the Nkx2.5$^{cre}$ line resulted in high-level expression of all members of the miR302-367 cluster (FIG. 9C) and a marked increase in cardiomyocyte proliferation at E18.5 (FIG. 2A). Nkx2.5$^{cre}$:R26R-miR302-367$^{Tg/+}$ mutants died by P28. At P20, Nkx2.5$^{cre}$:R26R-miR302-367$^{Tg/+}$ mutants exhibited profound cardiac enlargement, or cardiomegaly, accompanied by extensive cardiomyocyte proliferation (FIG. 2B). This is in contrast to control littermates, which did not exhibit noticeable cardiomyocyte proliferation at P20, consistent with previous observations.

Cardiomyocytes from P17 hearts were isolated and found to have a significant increase in the percentage of mononucleated and binucleated cardiomyocytes and a decrease in the percentage of multinucleated cardiomyocytes (FIG. 9D), suggesting that miR302-367 overexpression affects both cell cycle activity and nucleation of cardiomyocytes when expressed from the beginning of cardiac development. Although heart weight-to-tibia length ratios were significantly higher for Nkx2.5$^{cre}$:R26R-miR302-367$^{Tg/+}$ mutants at P20 (FIG. 9E), cardiomyocytes in these mutants were smaller and exhibited disorganized sarcomeric structure compared to control cardiomyocytes, suggesting increased cardiomyocyte number and a less mature phenotype (FIG. 3A and FIG. 9F). Nkx2.5$^{cre}$:R26R-miR302-367$^{Tg/+}$ mutant hearts had poor cardiac function with reduced ejection fraction and fractional shortening (FIG. 9G). Cardiomyocyte apoptosis was increased in Nkx2.5$^{cre}$:R26R-miR302-367$^{Tg/+}$ hearts at P20 compared with littermate control Nkx2.5$^{cre}$ hearts, but this may have been due to the overall defects in cardiomyocyte maturation, which led to compromised cardiac function and failure (FIG. 9H).

To better understand the effects that overexpression of miR302-367 has on the cardiomyocyte transcriptome, microarray analysis was performed on ventricles from Nkx2.5$^{cre}$:R26R-miR302-367$^{Tg/+}$ P14 mutant and control hearts. Gene ontology analysis revealed that the most differentially modulated genes in Nkx2.5$^{cre}$:R26R-miR302-367$^{Tg/+}$ hearts belonged to pathways involved in the control of cell proliferation and negative regulation of cell differentiation (FIG. 3B). qRT-PCR confirmed increased expression of a variety of cell proliferation-associated genes, including Brca2, RacGap1, Nusap1, Myh10, and Cks2, compared with Nkx2.5$^{cre}$ hearts (FIG. 3C), in addition to increased expression of Bcl2, which is a repressor of apoptosis, and several markers associated with negative regulation of cardiomyocyte differentiation, including Myh7, c-Kit, and Nppa (FIGS. 3, D and E). Expression of Myh6 was unaffected by miR302-367 over-expression (FIG. 3E). Overexpression of miR302-367 in developing cardiomyocytes therefore led to a highly proliferative, immature dedifferentiated phenotype in cardiomyocytes.

In contrast, miR302-367 overexpression resulted in down-regulation of programmed cell death (FIG. 3D). miR302-367 overexpression was also observed to result in down-regulation of fatty acid metabolism genes including PparA, PparD, and Acox1, suggesting cardiomyocyte dysfunction (FIG. 3F). Together, these data demonstrate increased proliferation and inhibition of maturation of cardiomyocytes in Nkx2.5$^{cre}$:R26R:miR302-367$^{Tg/+}$ mutants, indicating that persistent overexpression of miR302-367 leads to a de-differentiated cardiomyocyte phenotype and compromised cardiac function.

miR302-367 Inhibits Hippo Pathway to Promote Cardiomyocyte Proliferation

To further identify miR302-367 target genes, high-throughput sequencing of RNA isolated by cross-linking immunoprecipitation (HITS-CLIP) was performed with argonaute-2/miRNA:mRNA complexes. Mouse ES cells were used given the high level of miR302-367 expression in these cells. Using a stringent cutoff of 100 reads per million (RPM), 51 miRNAs including members of miR302-367 were detected (Table 1). The identified mRNA targets from HITS-CLIP were compared with all possible predictions of miRNA/mRNA targeting relationships obtained from miRanda. The overlap set contained 48 genes, many of which were associated with the regulation of cell cycle and apoptosis (FIG. 10A and Table 2).

In the HITS-CLIP data, miR-302 targeted sequences in the 3' untranslated region (3'UTR) of Mst1 (Stk4), a core component of Hippo signaling kinase cascade (Table 3). Moreover, miRanda predicted that Lats2 and Mob1b, essential kinases in the Hippo pathway, were potential targets of miR302. The Hippo signal transduction pathway regulates organ size and cell proliferation, and loss of Mst1/2 and Lats kinases in the developing mouse heart causes increased proliferation in cardiomyocytes. Thus, miR302-367 was hypothesized to regulate cardiomyocyte proliferation through the inhibition of Hippo signaling.

To verify changes in expression of Hippo components mediated by loss and gain of miR302-367 function, qRT-PCR and Western blots were performed on Nkx2.5$^{cre}$:miR302-367$^{flox/flox}$ and Nkx2.5$^{cre}$:R26RmiR302-367$^{Tg/+}$ hearts. These data revealed that overexpression of miR302-367 led to decreased expression of Mst1, Lats2, and Mob1b, whereas loss of miR302-367 expression led to increased expression of these genes (FIG. 4A and FIGS. 10, B and C). Expression of miR302-367 also led to decreased activity of luciferase reporters for the 3'UTRs of Mst1, Lats2, and Mob1b, and mutation of the miR302-367 binding sites abrogated this repression (FIG. 4B and FIG. 10D). These findings suggest that miR302-367 inhibits Hippo pathway activity through repression of the kinases Mst1, Lats2, and Mob1b.

Yes activated protein (Yap) is the downstream transcriptional effector of Hippo signaling. Phosphorylated Yap (phospho-Yap) normally resides in the cytoplasm and is transcriptionally inactive. Upon loss of Hippo signaling, Yap is translocated to the nucleus where it binds to members of the TEAD transcription factor family and activates gene expression, including pathways that promote proliferation and survival. Overexpression of a transcriptionally active form of Yap (YapS127A) in the mouse heart promotes cardiomyocyte proliferation and cardiac regeneration. To determine whether overexpression of miR302-367 affected Yap phosphorylation and activity, the expression of Yap and phospho-Yap was examined in Nkx2.5$^{cre}$:R26R-miR302-367$^{Tg/+}$ hearts. Cardiomyocytes of control hearts at E18.5 exhibited diffuse cytoplasmic location of phospho-Yap (FIG. 4C). Nkx2.5$^{cre}$:R26R-miR302-367$^{Tg/+}$ hearts showed reduced phospho-Yap expression. By contrast, immunostaining for total Yap revealed an increase in nuclear Yap in Nkx2.5$^{cre}$:R26R-miR302-367$^{Tg/+}$ hearts (FIG. 4C). Loss of miR302-367 expression also led to enhanced Yap phosphorylation, but decreased nuclear Yap expression, in the developing myocardium of Nkx2.5$^{cre}$:miR302-367$^{flox/flox}$ hearts at E10.5 (FIG. 10E).

To investigate whether miR302-367 regulation of Hippo signaling was responsible, at least in part, for the increased proliferation observed in cardiomyocytes of Nkx2.5$^{cre}$:R26R-miR302-367$^{Tg/+}$ hearts, Yap expression was inhibited using short hairpin RNAs (shRNAs) in the presence of miR302-367 expression in isolated neonatal mouse cardiomyocytes. Lentiviral overexpression of miR302-367 resulted in increased neonatal cardiomyocyte proliferation (FIG. 4D). shRNA-mediated inhibition of Yap resulted in decreased proliferation caused by miR302-367 overexpression (FIG. 4D and FIG. 10F).

The effects of individual miR-302 family members on cardiomyocyte proliferation was also examined. Treatment of mouse neonatal cardiomyocytes with a miR302b mimic led to an increased number of Ki67$^+$/cardiac Troponin T (cTnT)+ cardiomyocytes, whereas miR302c mimics did not induce a similar significant increase in proliferation (FIG. 3G). The use of both miR302b and miR302c mimics led to an additive increase in cardiomyocyte proliferation, greater than that with either mimic alone (FIG. 10G). Together, these data demonstrate that miR302-367 targets multiple components of the Hippo signal transduction pathway to promote cardiomyocyte proliferation, as illustrated in the schematic in FIG. 4E.

miR302-367 Promotes Adult Cardiac Regeneration after Myocardial Infarction Through Increased Cardiomyocyte Proliferation Whether conditional overexpression of miR302-367 in the adult heart could reactivate cardiomyocyte proliferation was then examined. $Myh6^{mercremer}$:R26R-miR302-367$^{Tg/+}$ animals were generated to specifically overexpress miR302-367 in cardiomyocytes in the adult heart. qRT-PCR confirmed high-level expression of all members of the miR302-367 cluster after tamoxifen administration (FIG. 11A and Table 4). Eight days after the start of tamoxifen treatment, the cardiomyocytes in $Myh6^{mercremer}$:R26R-miR302-367$^{Tg/+}$ hearts reentered the cell cycle (FIGS. 5, A and B). The number of cardiomyocytes undergoing mitosis (PH3+) and cytokinesis (Aurora B kinase+) was also increased in $Myh6^{mercremer}$:R26R-miR302-367$^{Tg/+}$ hearts (FIGS. 5, C and D), paralleled by a reduction in apoptosis (FIG. 11B).

The heart weight-to-tibia length ratio increased in $Myh6^{mercremer}$:R26R-miR302-367$^{Tg/+}$ animals 2 weeks after initiation of miR302-367 overexpression (FIG. 11C). The total number of cardiomyocytes as well as the percentage of mononucleated cardiomyocytes increased after 2 weeks (FIGS. 5, E and F). The size of cardiomyocytes in $Myh6^{mercremer}$:R26R-miR302-367$^{Tg/+}$ heart was also smaller compared to control cardiomyocytes (FIG. 5G). The expression of genes associated with cell proliferation, including Cks2 and Ccnd1, increased in $Myh6^{mercremer}$:R26R-miR302-367$^{Tg/+}$ hearts (FIG. 11D). In contrast, the expression of genes associated with Hippo signaling components and programmed cell death decreased in $Myh6^{mercremer}$:R26R-miR302-367$^{Tg/+}$ mutants (FIG. 11D). miR302-367 overexpression in the adult heart therefore resulted in cardiomyocyte cell cycle reactivation.

To determine whether ectopic expression of miR302-367 can promote cardiac regeneration in adult mice, LAD ligation-inducing a myocardial infarction (MI) was performed on $Myh6^{mercremer}$:R26RmiR302-367$^{Tg/+}$ and control $Myh6^{mercremer}$ mice (FIG. 6A). Three weeks after injury, $Myh6^{mercremer}$ hearts exhibited extensive fibrotic scarring and loss of myocardial tissue, whereas $Myh6^{mercremer}$:R26R-miR302-367$^{Tg/+}$ hearts had significantly reduced fibrotic scarring with an increase in myocardial tissue (FIGS. 6, B and C). Immunostaining showed reduced expression of phospho-Yap, but enhanced expression of nuclear Yap, in $Myh6^{mercremer}$:R26R-miR302-367$^{Tg/+}$ hearts compared to $Myh6^{mercremer}$ hearts (FIG. 12A). Moreover, the number of PH3+ cardiomyocytes was significantly higher in $Myh6^{mercremer}$:R26R-miR302-367$^{Tg/+}$ hearts than in $Myh6^{mercremer}$ controls 3 weeks after injury (FIG. 6D). These data indicate that expression of miR302-367 in the adult heart can promote cardiomyocyte proliferation, which contributes to reduced post-injury fibrotic scarring.

Despite these intriguing findings, $Myh6^{mercremer}$:R26R-miR302-367$^{Tg/+}$ hearts exhibited ventricular dilation and a reduction in fractional shortening and ejection fraction 3 weeks after injury (FIG. 6E). Sustained cardiomyocyte proliferation in the adult heart was hypothesized to be caused by prolonged miR302-367 overexpression compromised cardiac function, possibly by inducing a persistent dedifferentiated and highly proliferative phenotype. The expression of genes associated with cardiomyocyte proliferation and differentiation was examined at days 10 and 21 after miR302-367 overexpression. There was a persistent up-regulation of Cks2, a marker for cell proliferation, at both time points in $Myh6^{mercremer}$:R26R-miR302-367$^{Tg/+}$ hearts (FIG. 12B). In contrast, we observed the persistent down-regulation in the ratio of Myh6 (a-myosin heavy chain) to Myh7 (b-myosin heavy chain), a marker for fetal gene activation in the rodent hearts that is associated with cardiac dysfunction and failure, in $Myh6^{mercremer}$:R26R-miR302-367$^{Tg/+}$ hearts (FIG. 12B).

To determine whether the myocardial lineage had undergone de-differentiation and sarcomeric disassembly by miR302-367 overexpression, we lineage-traced the $Myh6^{mercremer}$:R26R-miR302-367$^{Tg/+}$ line and observed disorganized sarcomeres and reduced sarcomeric gene expression in the Myh6 myocardial lineage positive cells (FIG. 12C). Together, these findings demonstrate that persistent expression of miR302-367 in the adult heart reactivates the cardiomyocyte cell cycle and increases cardiomyocyte regeneration. However, such a persistent stimulus leads to induction of a dedifferentiated phenotype and organ-wide dysfunction leading to heart failure.

Transient miR302 Mimic Therapy Promotes Cardiac Regeneration and Improves Function after Injury To examine whether transient miR302-367 expression could overcome the adverse effects of persistent expression on the heart, adult mice were treated with miRNA miR302-367 mimics. Whether tail-vein injection of miR302b/c/367 mimics led to accumulation of these miRNAs in the heart was evaluated. miR302b/c/367 mimic levels peaked between 4 and 8 hours after injection and returned to baseline 24 hours after injection (FIG. 13A). Similar transient expression of miR302b/c/367 was observed in other organs, including the lung (FIG. 14A). For subsequent experiments, only miR302b/c mimics were used, because these miRNAs target Hippo signaling components here (FIG. 10G and Table 3) and in a previous study.

miR302b/c mimics or a negative control mimic were administered daily for 7 days by tail-vein injections. The expression of miR302-targeted genes related to the Hippo pathway, including Mst1, Lats2, and Mob1b, were decreased in the hearts of miR302b/c mimic-treated mice (FIG. 13B). Expression of genes associated with cardiomyocyte differentiation and proliferation were examined at an early time point (day 8) and late time point (day 21) after mimic treatment. The expression of the proliferation-associated gene Ccnd1 increased at day 8, but returned to basal levels at day 21 (FIG. 13C). The expression of Nppa and the ratio of Myh6 to Myh7 expression were also altered at day 8, but returned to normal levels at day 21 (FIG. 13C).

Next, adult mice were treated with miR302b/c mimics or a negative control miRNA mimic, using daily tail-vein injections starting 1 day after MI and continuing daily for 7 days. The expression of the Hippo signaling components Mst1 and Mob1b was significantly decreased in miR302b/c mimic-treated hearts after MI compared to the controls (FIG. 13D). Forty-eight hours after the final treatment, increased cardiomyocyte proliferation and decreased apoptosis was observed in the hearts of miR302b/c mimic-treated mice (FIG. 13E). On the final treatment day (day 8 after MI), there was a significant increase in the expression of genes associated with cell proliferation (Ccnd1), antiapoptosis (Bcl2), and fetal gene program (Nppa, Myh7) in miR302b/c mimic-treated hearts; however, expression returned to basal levels 4 weeks after surgery (FIG. 13F). This ratio of Myh6 to Myh7 expression, which was decreased at 8 days, was increased at 4 weeks (FIG. 13F), suggesting transient de-differentiation of cardiomyocytes in miR302b/c mimic-treated hearts.

Analysis of miR302b/c mimic-treated hearts 50 days after injury showed that they also had significantly less fibrotic scarring than the control mimic-treated hearts (FIG. 7, A to C). Functional assessment of miR302b/c mimic-treated animals showed that they exhibited significantly increased fractional shortening and ejection fraction after injury compared with the control mimic-treated animals but did not reach the ejection fraction and fractional shortening of sham animals (FIG. 7D). miR302b/c mimic-treated mice displayed reduced cardiac remodeling, as gauged by end-diastolic volume and end-systolic volume measurements (FIG. 7E). Moreover, miR302b/c mimics increased the density of new blood vessels in the peri-infarct zone but did not affect vascular cell proliferation (FIG. 13, G to I). Abnormalities were not observed in other organs, including the lung, liver, and intestine, in miR302b/c mimic-treated mice at 50 days after MI (6 weeks after final treatment), suggesting no adverse effects (FIG. 14B). Together, these data indicate that transient expression of miR302 mimics resulted in improved cardiac repair and regeneration after MI.

TABLE 1

HITS-CLIPS DATA

| SeqID | Score |
| --- | --- |
| mmu-miR-293 | 465744 |
| mmu-miR-294 | 124328.5 |
| mmu-miR-2134-3 | 119289 |
| mmu-miR-19b-2 | 51813 |
| mmu-miR-19b-1 | 51813 |
| mmu-miR-19a | 45137.99 |
| mmu-miR-27a | 39680.33 |
| mmu-miR-92a-1 | 38676.06 |
| mmu-miR-291a-3p | 30613.46 |
| mmu-miR-30e | 24779 |
| mmu-miR-25 | 22700.27 |
| mmu-miR-18b | 20369.99 |
| mmu-miR-106a | 18738.99 |
| mmu-miR-669f-5p | 18383.15 |
| mmu-miR-2132 | 15172 |
| mmu-miR-302b | 12211.98 |
| mmu-miR-292-3p | 11321 |
| mmu-miR-2144 | 9943 |
| mmu-miR-669c-3p | 9460 |
| mmu-miR-23b | 9357.999 |
| mmu-miR-714 | 8907 |
| mmu-miR-2133-2-3p | 8877.997 |
| mmu-miR-543 | 8845 |
| mmu-miR-363 | 8686 |
| mmu-miR-433 | 8470 |
| mmu-miR-425 | 8345 |
| mmu-miR-154 | 8100 |
| mmu-miR-191 | 8069 |
| mmu-miR-1944-5p | 7115 |
| mmu-miR-302a | 6828.022 |
| mmu-miR-429 | 6541 |
| mmu-miR-467a | 6458 |
| mmu-miR-467d | 6458 |
| mmu-miR-466i-5p | 5741.412 |
| mmu-miR-149 | 5438 |
| mmu-miR-96 | 5031 |
| mmu-miR-698-5p | 4990 |
| mmu-miR-467d | 4966.998 |
| mmu-miR-335-3p | 4945 |
| mmu-miR-20a | 4870.999 |
| mmu-miR-484 | 4683 |
| mmu-miR-295 | 4121 |
| mmu-miR-2143-1 | 4059.5 |
| mmu-miR-2134-4 | 2738 |
| mmu-miR-2134-2 | 2738 |
| mmu-miR-466k | 956 |
| mmu-miR-2143-3 | 675.75 |
| mmu-miR-2143-2 | 675.75 |
| mmu-miR-210 | 565 |
| mmu-miR-615-5p | 235.9958 |
| mmu-miR-714-3p | 105.6667 |

TABLE 2

OVERLAPPING GENES BETWEEN HITS-CLIP AND PREDICTED MIR302 TARGETS.

| GENBANK_ACCESSION | Name | Species |
| --- | --- | --- |
| NM_175550 | adaptor-related protein complex AP-4, epsilon 1 | Mus musculus |
| NM_173755 | ubiquitin-conjugating enzyme E2O | Mus musculus |
| NM_008489 | lipopolysaccharide binding protein | Mus musculus |
| NM_010178 | predicted gene 5446; similar to FUS interacting protein (serine-arginine rich) 1; FUS interacting protein (serine-arginine rich) 1 | Mus musculus |
| NM_001079883 | B-cell leukemia/lymphoma 11B | Mus musculus |
| NM_026205 | ring finger protein 151 | Mus musculus |
| NM_183417 | cyclin-dependent kinase 2 | Mus musculus |
| NM_134163 | muscleblind-like 3 (Drosophila) | Mus musculus |
| NM_009212 | immunoglobulin mu binding protein 2 | Mus musculus |
| NM_144812 | trinucleotide repeat containing 6b | Mus musculus |
| NM_144810 | kelch domain containing 8A | Mus musculus |
| NM_023755 | transcription factor CP2-like 1 | Mus musculus |
| NM_012042 | cullin 1 | Mus musculus |
| NM_011717 | widely-interspaced zinc finger motifs | Mus musculus |
| NM_008379 | karyopherin (importin) beta 1 | Mus musculus |
| NM_008997 | RAB11B, member RAS oncogene family | Mus musculus |
| NM_011212 | protein tyrosine phosphatase, receptor type, E | Mus musculus |
| NM_027514 | poliovirus receptor | Mus musculus |
| NM_026186 | coiled-coil domain containing 49 | Mus musculus |
| NM_011390 | solute carrier family 12, member 7 | Mus musculus |
| NM_198022 | trinucleotide repeat containing 6C | Mus musculus |

TABLE 2-continued

OVERLAPPING GENES BETWEEN HITS-CLIP AND PREDICTED MIR302 TARGETS.

| GENBANK_ACCESSION | Name | Species |
|---|---|---|
| NM_001081176 | polymerase (RNA) III (DNA directed) polypeptide G | Mus musculus |
| NM_001039059 | kelch-like 15 (Drosophila) | Mus musculus |
| NM_133715 | Rho GTPase activating protein 27; SH3 domain containing 20 | Mus musculus |
| NM_026145 | potassium channel tetramerisation domain containing 10 | Mus musculus |
| NM_001031772 | lin-28 homolog B (C. elegans) | Mus musculus |
| NM_172516 | dual serine/threonine and tyrosine protein kinase | Mus musculus |
| NM_054097 | phosphatidylinositol-5-phosphate 4-kinase, type II gamma | Mus musculus |
| NM_021559 | zinc finger protein 191 | Mus musculus |
| NM_009723 | ATPase, Ca++ transporting, plasma membrane 2 | Mus musculus |
| NM_019535 | SH3-domain GRB2-like 2 | Mus musculus |
| NM_009274 | serine/arginine-rich protein specific kinase 2 | Mus musculus |
| NM_001111099 | cyclin-dependent kinase inhibitor 1A (P21) | Mus musculus |
| NM_177239 | similar to mKIAA1915 protein; myb-like, SWIRM and MPN domains 1 | Mus musculus |
| NM_207682 | kinesin family member 1B | Mus musculus |
| NM_001012330 | zinc finger protein 238 | Mus musculus |
| NM_007798 | cathepsin B | Mus musculus |
| NM_001013380 | dynein, cytoplasmic 1 light intermediate chain 2 | Mus musculus |
| NM_007520 | BTB and CNC homology 1 | Mus musculus |
| NM_021420 | serine/threonine kinase 4 | Mus musculus |
| NM_133352 | transmembrane 9 superfamily member 3 | Mus musculus |
| NM_007610 | caspase 2 | Mus musculus |
| NM_001081196 | heterogeneous nuclear ribonucleoprotein U-like 2 | Mus musculus |
| NM_011358 | splicing factor, arginine/serine-rich 2 (SC-35) | Mus musculus |
| NM_010880 | nucleolin | Mus musculus |
| NM_013876 | ring finger protein 11 | Mus musculus |
| NM_010700 | low density lipoprotein receptor | Mus musculus |
| NM_031408 | GRB10 interacting GYF protein 1 | Mus musculus |

TABLE 3

MIR302 TARGETS IDENTIFIED FROM HITS-CLIP.

| mmu-miR-302b-AGCACTT | | mmu-miR-302a-AGCACTT | |
|---|---|---|---|
| Fusip1 | NM_010178 | Fusip1 | NM_010178 |
| Zfp426 | NM_001110309 | Zfp426 | NM_001110309 |
| Casc4 | NM_199038 | Casc4 | NM_199038 |
| Zfp426 | NM_146221 | Zfp426 | NM_146221 |
| Tnrc6c | NM_198022 | Tnrc6c | NM_198022 |
| Bach1 | NM_007520 | Bach1 | NM_007520 |
| Wiz | NM_011717 | Wiz | NM_011717 |
| Lbp | NM_008489 | Lbp | NM_008489 |
| Snx8 | NM_172277 | Snx8 | NM_172277 |
| Casc4 | NM_177054 | Casc4 | NM_177054 |
| Rbbp7 | NM_009031 | Rbbp7 | NM_009031 |
| Ube2b | NM_009458 | Ube2b | NM_009458 |
| 4632434I11Rik | NM_001080995 | 4632434I11Rik | NM_001080995 |
| Bcl11b | NM_001079883 | Bcl11b | NM_001079883 |
| Glrx3 | NM_023140 | Glrx3 | NM_023140 |
| Wiz | NM_212438 | Wiz | NM_212438 |
| LOC100041128 | XM_001475846 | LOC100041128 | XM_001475846 |
| Kctd10 | NM_026145 | Kctd10 | NM_026145 |
| Bcl11b | NM_021399 | Bcl11b | NM_021399 |
| Rab22a | NM_024436 | Rab22a | NM_024436 |
| Mbnl3 | NM_134163 | Mbnl3 | NM_134163 |
| Tnrc6b | NM_144812 | Tnrc6b | NM_144812 |
| Eif2s1 | NM_026114 | Eif2s1 | NM_026114 |
| Lpcat3 | NM_145130 | Lpcat3 | NM_145130 |
| Pvr | NM_027514 | Pvr | NM_027514 |
| Thex1 | NM_026067 | Thex1 | NM_026067 |
| Pom121 | NM_148932 | Pom121 | NM_148932 |
| Klhl15 | NM_153165 | Klhl15 | NM_153165 |
| Arhgap27 | NM_133715 | Arhgap27 | NM_133715 |
| Svop | NM_026805 | Svop | NM_026805 |
| Lman1 | NM_027400 | Lman1 | NM_027400 |
| Dennd2d | NM_028110 | Dennd2d | NM_028110 |
| Zbtb4 | NM_029348 | Zbtb4 | NM_029348 |
| Gigyf1 | NM_031408 | Gigyf1 | NM_031408 |
| Mfap1a | NM_026220 | Mfap1a | NM_026220 |

TABLE 3-continued

MIR302 TARGETS IDENTIFIED FROM HITS-CLIP.

| mmu-miR-302b-AGCACTT | | mmu-miR-302a-AGCACTT | |
|---|---|---|---|
| Rnf151 | NM_026205 | Rnf151 | NM_026205 |
| Ccdc49 | NM_026186 | Ccdc49 | NM_026186 |
| Pip4k2c | NM_054097 | Pip4k2c | NM_054097 |
| Tm9sf3 | NM_133352 | Tm9sf3 | NM_133352 |
| Cd81 | NM_133655 | Cd81 | NM_133655 |
| Papd1 | NM_026157 | Papd1 | NM_026157 |
| Klhdc8a | NM_144810 | Klhdc8a | NM_144810 |
| Bclaf1 | NM_153787 | Bclaf1 | NM_153787 |
| Ripk5 | NM_172516 | Ripk5 | NM_172516 |
| Dsp | XM_896350 | Dsp | XM_896350 |
| LOC677060 | XM_001000215 | LOC677060 | XM_001000215 |
| LOC100045782 | XM_001475154 | LOC100045782 | XM_001475154 |
| LOC100046594 | XM_001477687 | LOC100046594 | XM_001477687 |
| LOC100042306 | XM_001478003 | LOC100042306 | XM_001478003 |
| LOC100047941 | XM_001479195 | LOC100047941 | XM_001479195 |
| LOC100047941 | XM_001479195 | LOC100047941 | XM_001479195 |
| LOC100048076 | XM_001479683 | LOC100048076 | XM_001479683 |
| LOC100048076 | XM_001479685 | LOC100048076 | XM_001479685 |
| LOC100048559 | XM_001480897 | LOC100048559 | XM_001480897 |
| Dsp | XM_001481272 | Dsp | XM_001481272 |
| BC051076 | XM_144407 | BC051076 | XM_144407 |
| Fbxo3 | NM_212433 | Fbxo3 | NM_212433 |
| Kif1b | NM_207682 | Kif1b | NM_207682 |
| Sfrs1 | NM_173374 | Sfrs1 | NM_173374 |
| Ube2o | NM_173755 | Ube2o | NM_173755 |
| Ap4e1 | NM_175550 | Ap4e1 | NM_175550 |
| Tnrc6b | NM_177124 | Tnrc6b | NM_177124 |
| Mysm1 | NM_177239 | Mysm1 | NM_177239 |
| Mysm1 | NM_177239 | Mysm1 | NM_177239 |
| Pik3ip1 | NM_178149 | Pik3ip1 | NM_178149 |
| Elmod2 | NM_178736 | Elmod2 | NM_178736 |
| Hisppd2a | NM_178795 | Hisppd2a | NM_178795 |
| Cdk2 | NM_183417 | Cdk2 | NM_183417 |
| Prosapip1 | NM_197945 | Prosapip1 | NM_197945 |
| Lrrc47 | NM_201226 | Lrrc47 | NM_201226 |
| Dsp | XM_621314 | Dsp | XM_621314 |
| Zfp238 | NM_001012330 | Zfp238 | NM_001012330 |
| Ppp1r3d | NM_001085501 | Ppp1r3d | NM_001085501 |
| Ppp1r3d | NM_001085501 | Ppp1r3d | NM_001085501 |
| Dennd2d | NM_001093754 | Dennd2d | NM_001093754 |
| Cdyl | NM_001123386 | Cdyl | NM_001123386 |
| Car8 | NM_007592 | Car8 | NM_007592 |
| Casp2 | NM_007610 | Casp2 | NM_007610 |
| Ctsb | NM_007798 | Ctsb | NM_007798 |
| Kpnb1 | NM_008379 | Kpnb1 | NM_008379 |
| Mycn | NM_008709 | Mycn | NM_008709 |
| Ntrk2 | NM_008745 | Ntrk2 | NM_008745 |
| Ptbp1 | NM_008956 | Ptbp1 | NM_008956 |
| Ptbp1 | NM_008956 | Ptbp1 | NM_008956 |
| Ptafr | NM_001081211 | Ptafr | NM_001081211 |
| Hnrnpul2 | NM_001081196 | Hnrnpul2 | NM_001081196 |
| Polr3g | NM_001081176 | Polr3g | NM_001081176 |
| Dync1li2 | NM_001013380 | Dync1li2 | NM_001013380 |
| Bclaf1 | NM_001025392 | Bclaf1 | NM_001025392 |
| Bclaf1 | NM_001025393 | Bclaf1 | NM_001025393 |
| Mex3a | NM_001029890 | Mex3a | NM_001029890 |
| Lin28b | NM_001031772 | Lin28b | NM_001031772 |
| Gm410 | NM_001033349 | Gm410 | NM_001033349 |
| Atp2b2 | NM_001036684 | Atp2b2 | NM_001036684 |
| Klhl15 | NM_001039059 | Klhl15 | NM_001039059 |
| Klhl15 | NM_001039060 | Klhl15 | NM_001039060 |
| Ptbp1 | NM_001077363 | Ptbp1 | NM_001077363 |
| Ptbp1 | NM_001077363 | Ptbp1 | NM_001077363 |
| Sfrs1 | NM_001078167 | Sfrs1 | NM_001078167 |
| Rab11b | NM_008997 | Rab11b | NM_008997 |
| Ighmbp2 | NM_009212 | Ighmbp2 | NM_009212 |
| Srpk2 | NM_009274 | Srpk2 | NM_009274 |
| Rnf11 | NM_013876 | Rnf11 | NM_013876 |
| Zfp238 | NM_013915 | Zfp238 | NM_013915 |
| Abce1 | NM_015751 | Abce1 | NM_015751 |
| Cdk2 | NM_016756 | Cdk2 | NM_016756 |
| Sh3gl2 | NM_019535 | Sh3gl2 | NM_019535 |
| Cdgap | NM_020260 | Cdgap | NM_020260 |
| Stk4 | NM_021420 | Stk4 | NM_021420 |
| Stk4 | NM_021420 | Stk4 | NM_021420 |
| Zfp191 | NM_021559 | Zfp191 | NM_021559 |

TABLE 3-continued

MIR302 TARGETS IDENTIFIED FROM HITS-CLIP.

| mmu-miR-302b-AGCACTT | | mmu-miR-302a-AGCACTT | |
|---|---|---|---|
| Moap1 | NM_022323 | Moap1 | NM_022323 |
| Tcfcp2l1 | NM_023755 | Tcfcp2l1 | NM_023755 |
| Dsp | NM_023842 | Dsp | NM_023842 |
| Aoah | NM_012054 | Aoah | NM_012054 |
| Cul1 | NM_012042 | Cul1 | NM_012042 |
| Sept3 | NM_011889 | Sept3 | NM_011889 |
| Atp2b2 | NM_009723 | Atp2b2 | NM_009723 |
| Cdyl | NM_009881 | Cdyl | NM_009881 |
| Cd47 | NM_010581 | Cd47 | NM_010581 |
| Ldlr | NM_010700 | Ldlr | NM_010700 |
| Ncl | NM_010880 | Ncl | NM_010880 |
| Neurod1 | NM_010894 | Neurod1 | NM_010894 |
| Pax8 | NM_011040 | Pax8 | NM_011040 |
| Pkm2 | NM_011099 | Pkm2 | NM_011099 |
| Ptpre | NM_011212 | Ptpre | NM_011212 |
| Sfrs2 | NM_011358 | Sfrs2 | NM_011358 |
| Slc12a7 | NM_011390 | Slc12a7 | NM_011390 |
| Slc12a7 | NM_011390 | Slc12a7 | NM_011390 |
| Cyb5 | NM_025797 | Cyb5 | NM_025797 |
| Cdkn1a | NM_001111099 | Cdkn1a | NM_001111099 |

TABLE 4

MIRNA QRT-PCR ANALYSIS IN ADULT MOUSE HEART.
Ct value by Q-PCR analysis

| Mouse genotype and ID | miR-302a | miR-302c | miR-302b | miR-302d | miR-367 | sn-202 |
|---|---|---|---|---|---|---|
| Myh6-MerCreMer-1 (#2630) | 35.23037 | 36.587448 | 35.117035 | 34.552624 | 34.508602 | 19.487278 |
|  | 35.093464 | 36.953339 | 34.433346 | 34.427361 | 34.822618 | 19.123663 |
| Myh6-MerCreMer-2 (#884) | 35.928413 | 35.569115 | 34.951195 | 34.472588 | 34.922916 | 19.590122 |
|  | 35.207722 | 34.75927 | 34.99754 | 34.187965 | 35.226227 | 19.71003 |
| Myh6-MerCreMer-3 (#831) | 34.501678 | 36.279041 | 34.772966 | 34.370388 | 34.952389 | 18.705404 |
|  | 35.513676 | 36.732643 | 34.890965 | 34.416424 | 35.549946 | 18.965477 |
| Myh6-MerCreMer; R26R-miR302-367 Tg-1 (#2625) | 18.499952 | 20.837721 | 18.094967 | 17.800104 | 18.342041 | 19.420469 |
|  | 18.511406 | 21.029299 | 18.094952 | 17.000566 | 18.141062 | 19.318007 |
| Myh6-MerCreMer; R26R-miR302-367 Tg-2 (#2139) | 18.611528 | 20.643997 | 18.089294 | 17.950405 | 17.973259 | 19.098368 |
|  | 18.43906 | 20.782874 | 18.261478 | 16.922874 | 18.015085 | 19.148411 |
| Myh6-MerCreMer; R26R-miR302-367 Tg-3 (#2678) | 17.946672 | 19.898573 | 17.57185 | 17.44083 | 17.74843 | 19.098368 |
|  | 18.169876 | 19.9618 | 17.31517 | 17.404823 | 17.788476 | 19.148411 |
| Myh6-MerCreMer; R26R-miR302-367 Tg-4 (#6360) | 18.813637 | 20.547285 | 18.047836 | 17.263132 | 18.234688 | 19.181335 |
|  | 18.851551 | 20.520567 | 18.128296 | 17.116985 | 18.309748 | 19.277533 |

TABLE 5

PRIMERS FOR GENOTYPING, QRT-PCR, AND LUCIFERASE REPORTER ANALYSES.

Genotyping primers

| mouse alleles | Forward | Reverse |
|---|---|---|
| miR-302-367 floxed allele | CACAAGGAGAGACATAAGATGGGC (SEQ ID NO 10) | CACTTTAGCAATGGTGATGGACC (SEQ ID NO 11) |
| R26R-miR302-367 | AAAGTCGCTCTGAGTTGTTAT (SEQ ID NO 12) | TCCCTATTGGCGTTACTATG (SEQ ID NO 13) |
| Nkx2.5-Cre | CGTTTTCTGAGCATACCTGGA (SEQ ID NO 14) | ATTCTCCCACCGTCAGTACG (SEQ ID NO 15) |
| Myh6-MerCreMer | CGTTTTCTGAGCATACCTGGA (SEQ ID NO 16) | ATTCTCCCACCGTCAGTACG (SEQ ID NO 17) |

Q-PCR primers

| Gene name | Forward | Reverse |
|---|---|---|
| Ccnd1 | GATGTGAGGGAAGAGGTGAAGGT (SEQ ID NO 18) | CAATGAGAATCTGGTTCTGAACGT (SEQ ID NO 19) |
| Nkx2.5 | TGACCCAGCCAAAGACCCT (SEQ ID NO 20) | CCATCCGTCTCGGCTTTGT (SEQ ID NO 21) |
| Gata4 | CCGGGCTGTCATCTCACTATG (SEQ ID NO 22) | TTCAGAGCAGACAGCACTGGAT (SEQ ID NO 23) |
| Myh6 | CCACTTCTCCTTGGTCCACTATG (SEQ ID NO 24) | ACAAACCCACCACCGTCTCA (SEQ ID NO 25) |

TABLE 5-continued

PRIMERS FOR GENOTYPING, QRT-PCR, AND LUCIFERASE REPORTER ANALYSES.

| | | |
|---|---|---|
| Myh7 | TACCTCATGGGGCTGAACTC (SEQ ID NO 26) | CCCTTGGTGACGTACTCGTT (SEQ ID NO 27) |
| Mob1b | CTGTGATCCAGCTTCAGGAGGAA (SEQ ID NO 28) | TGCCAACTCTCGTCTGTCAA (SEQ ID NO 29) |
| Lats2 | TAAGGGTCCTGCTTCCTGTGTTCT (SEQ ID NO 30) | ACCTCTCATGTGAAAGAGGCCCAA (SEQ ID NO 31) |
| Mst1 | CAGGGCCTGCATAACATTTGCTGT (SEQ ID NO 32) | TTCCTTGTCTGGCAAAGCCCAAAG (SEQ ID NO 33) |
| Bcl2 | GTGGATGACTGAGTACCTGAAC (SEQ ID NO 34) | GAGACAGCCAGGAGAAATCAA (SEQ ID NO 35) |
| Brca2 | ATTTGAACGGCCCAGCAT (SEQ ID NO 36) | GGCTGGTAAACCTGGAGTAAAG (SEQ ID NO 37) |
| RacGap1 | CAGATCCAGTGACAATGTTCCA (SEQ ID NO 38) | TCCACCATCATGAACTGATTCC (SEQ ID NO 39) |
| Nusap1 | GAGGAGGAAGAAGCACAAGAC (SEQ ID NO 40) | CTACTATCAGTTCCTTTCATCTCCAA (SEQ ID NO 41) |
| Myh10 | GGAATTCGAGAGGCAGAACAA (SEQ ID NO 42) | AAGGCTCGCTTGGATTTCTC (SEQ ID NO 43) |
| Cks2 | CAGAGTCTAGGATGGGTTCATTAC (SEQ ID NO 44) | TCCCAGCTGCACTTCATTT (SEQ ID NO 45) |
| Dapk1 | GCTGAACATGGAGCTGACTT (SEQ ID NO 46) | CAAGGAGGGTCTTGATGACTTC (SEQ ID NO 47) |
| Stk17B | AATCTGCATGAGGTCTACGAAA (SEQ ID NO 48) | TCGGCTAACTCAGGTAAACAC (SEQ ID NO 49) |
| c-Kit | CTAGCCAGAGACATCAGGAATG (SEQ ID NO 50) | CTCCCAGAGGAAAATCCCATAG (SEQ ID NO 51) |
| Nppa | GGGTAGGATTGACAGGATTGG (SEQ ID NO 52) | CTCCTTGGCTGTTATCTTCGG (SEQ ID NO 53) |
| PparA | AGGGGGACTGCATAGTTTGTC (SEQ ID NO 54) | TTCTCGGCCATACACAAGGT (SEQ ID NO 55) |
| PparD | ATCTCTGTCTCTCCCTGCCC (SEQ ID NO 56) | CTGTGGCTGTTCCATGACTG (SEQ ID NO 57) |
| Acox1 | GAAATATGCCCAGGTGAAGC (SEQ ID NO 58) | CAGACTCTGAGCTGCACTTCC (SEQ ID NO 59) |
| Pdk4 | TGAACACGCTTCACCCACTA (SEQ ID NO 60) | CAGGCAGGATGTCAATCTCC (SEQ ID NO 61) |
| Larp7 E12-13 | GGATCATGAGCAGAGGTACTG (SEQ ID NO 62) | GACTGGCTTGCTGAGTCTTAG (SEQ ID NO 63) |
| Larp7 E8-9 | TCTCAAAGGTGAAGAGGAAGC (SEQ ID NO 64) | TCTTGGACAGCACTCTCAATG (SEQ ID NO 65) |
| Larp7 E89-10 | ATTGAGAGTGCTGTCCAAGAC (SEQ ID NO 66) | TCTCCGCTCACAATCTTCAC (SEQ ID NO 67) |
| GAPDH | TGCACCACCAACTGCTTAGC (SEQ ID NO 68) | GGCATGGACTGTGGTCATGAG (SEQ ID NO 69) |

Luciferase reporter assay cloning information

| Name | Primer sequence |
|---|---|
| Lats2 XhoI fwd | cctcgagg TTCTGGTAAATGGGCAACAG (SEQ ID NO 70) |
| Lats2 EcoRI rev | ggaattcc TTTACATTTGCCTCCCGAAG (SEQ ID NO 71) |
| Mst1 XhoI fwd | ccgctcgag CAACACCAGCCCAGC (SEQ ID NO 72) |
| Mst1 BamHI rev | cgcggatcc CCTAGCAGCCATTTATCATC (SEQ ID NO 73) |
| Mob1b XhoI fwd | ccgctcgag AGGTTTTGGGGCTTGCTTGG (SEQ ID NO 74) |
| Mob1b EcoRI rev | ccggaattc GGAGTCAGGATGCTTCAAACTGC (SEQ ID NO 75) |

Although various cell therapies have been proposed for cardiac regeneration or treatment of heart failure, several clinical trials have indicated limited efficacy for such strategies. An alternative approach is to promote endogenous cardiomyocyte proliferation to regenerate and repair the heart, both after injury and in chronic disease states. Although previous studies have detected a very low level of postnatal cardiomyocyte proliferation in the mouse and human heart, it is insufficient to promote cardiac repair and regeneration after injury in mammals. Pathways that can be harnessed to promote cardiomyocyte proliferation are ideal targets for new therapeutic approaches for cardiac regeneration in humans. miRNAs have emerged as important regulators of and possible therapeutic targets in cardiovascular disease.

Here, the miR302-367 cluster is demonstrated to promote embryonic and postnatal cardiomyocyte proliferation, in part through targeting multiple kinases in the Hippo signal transduction pathway. Transient treatment of mice with small-molecule miR302 mimics led to improved cardiac regeneration, increased cardiomyocyte proliferation and survival, and improved vessel formation in the peri-infarct region—all accompanied by decreased fibrosis. The reduced fibrotic scarring was likely due to the observed enhancement of myocardial regeneration. In support of this argument, zebrafish experiments have shown that cardiac injury induces a high level of cardiomyocyte proliferation with a concomitant decrease in fibrotic scarring. Additional studies have indicated that cardiomyocytes can inhibit cardiac fibrosis in a paracrine manner. These studies provide a framework to further explore miRNA mimic-based treatments to promote heart repair and regeneration in humans.

The Hippo pathway regulates proper organ size by regulating cell proliferation, as well as programmed cell death. Recent studies have shown that inhibition of Yap phosphorylation through loss of key components in the pathway, such as Salvador/WW45, or expression of a phosphorylation-resistant form of Yap can lead to a profound increase in adult mouse cardiomyocyte proliferation. Cardiac-specific loss of Yap leads to increased myocyte apoptosis and fibrosis. Here, miR302-367 targeted multiple components of the Hippo signaling kinase cascade to promote cardiomyocyte proliferation. Furthermore, overexpression of miR302-367 promoted cell proliferation while decreasing programmed cell death, consistent with inhibition of Hippo signaling. Moreover, loss of miR302-367 led to increased phospho-Yap, but decreased nuclear Yap, in $Nkx2.5^{cre}$: $miR302-367^{flox/flox}$ mouse hearts. However, these experiments did not lead to a complete loss of Yap or its function, which likely accounted for the milder phenotype in these mice in comparison to a total loss of Yap.

miR302-367 is expressed at high levels in both the developing mouse heart and lung, as well as in ES cells, where it plays an important role in promoting pluripotency. Other miRNAs have also been shown to promote murine cardiomyocyte proliferation, including miR590 and the miR17-92 family. miR17-92 is expressed in the developing mouse heart and lung, and can promote a highly proliferative and undifferentiated state in lung epithelium, similar to miR302-367. As such, certain miRNAs can maintain an undifferentiated state by promoting high levels of cell proliferation while inhibiting differentiation. miRNA mimic strategies have been shown here to promote cardiac regeneration in vivo in a transient manner that avoids the deleterious effects of persistent cardiomyocyte dedifferentiation.

Previous studies describing overexpression of miR17-92 or YapS127A in mice did not report decreased cardiac function. Several reasons could explain the difference between the data here and these reports, including a more potent level of overexpression here and additional functions for miR302-367 that were not shared by these other approaches. Regardless of the mechanism, maintaining a persistent high level of cardiomyocyte proliferation could lead to dedifferentiation, directly or indirectly, which could cause compromised contractility and heart failure. The data here also provide a cautionary note that such therapies should be transient in nature to avoid prolonged cardiac dysfunction from the induction of a dedifferentiated state in proliferating cardiomyocytes.

This Example advances a new approach where a transient proliferative stimulus to the injured heart using a simple methodology based on miRNA and miRNA mimics. This approach has distinct advantages over cellular therapy because it does not require engraftment of exogenous cells, which has been a significant hurdle in the field of cardiac regeneration. Moreover, this approach overcomes the potential for persistent cardiomyocyte dedifferentiation owing to its transient nature, which should lead to preserved cardiomyocyte function after ischemic injury.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method for promoting cardiac repair and regeneration in a subject, the method comprising: transiently administering locally to the heart of said subject a composition comprising a microRNA (miR) 302-367 cluster or a miR 302-367 cluster mimic, wherein said transient administration is sufficient to transiently activate cardiomyocyte proliferation, but not to persistently reactivate the cell cycle of postnatal cardiomyocytes.

2. The method of claim 1, wherein the transient administration comprises a single administration of the composition to the subject.

3. The method of claim 1, wherein the composition comprises valproic acid.

4. The method of claim 1, wherein said miR is operably linked to a regulatory sequence.

5. The method of claim 4, wherein said regulatory sequence is an inducible promoter.

6. The method of claim 5, wherein said inducible promoter is a doxycycline inducible promoter.

7. The method of claim 1, wherein said miR is encoded by a nucleic acid sequence present within a vector.

8. The method of claim 7, wherein the vector is a viral vector.

9. The method of claim 8, wherein the viral vector is a lentivirus vector.

10. The method of claim 7, wherein the vector is a plasmid vector.

11. A method for promoting cardiac repair and regeneration in a subject, the method comprising: transiently administering locally to the heart of said subject a composition comprising a microRNA (miR) cluster or its mimic, wherein said cluster comprises one or more of miR302b and miR302c or two or more of miR302b, miR302c, and miR367, and wherein said transient administration is sufficient to transiently activate cardiomyocyte proliferation, but not to persistently reactivate the cell cycle of postnatal cardiomyocytes.

12. A method for promoting cardiac repair and regeneration in a subject, the method comprising: transiently administering intravenously at least once daily for 7 days said subject a composition comprising a microRNA (miR) 302-367 cluster or a miR 302-367 cluster mimic, wherein said transient administration is sufficient to transiently activate cardiomyocyte proliferation, but not to persistently reactivate the cell cycle of postnatal cardiomyocytes.

13. A method for promoting cardiac repair and regeneration in a subject, the method comprising: transiently administering intravenously at least once daily for 7 days said subject a composition comprising a microRNA (miR) cluster or its mimic, wherein said cluster comprises one or more of miR302b and miR302c or two or more of miR302b, miR302c, and miR367, and wherein said transient administration is sufficient to transiently activate cardiomyocyte proliferation, but not to persistently reactivate the cell cycle of postnatal cardiomyocytes.

* * * * *